United States Patent
Savariar et al.

(10) Patent No.: US 10,029,017 B2
(45) Date of Patent: Jul. 24, 2018

(54) PRETARGETED ACTIVATABLE CELL PENETRATING PEPTIDE WITH INTRACELLULARLY RELEASABLE PRODRUG

(71) Applicant: The Regents of the University of California, Oakland, CA (US)

(72) Inventors: Elamprakash N. Savariar, San Diego, CA (US); Jessica Crisp, San Diego, CA (US); Roger Y. Tsien, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 169 days.

(21) Appl. No.: 14/764,132

(22) PCT Filed: Jan. 29, 2014

(86) PCT No.: PCT/US2014/013687
§ 371 (c)(1),
(2) Date: Jul. 28, 2015

(87) PCT Pub. No.: WO2014/120837
PCT Pub. Date: Aug. 7, 2014

(65) Prior Publication Data
US 2015/0359902 A1 Dec. 17, 2015

Related U.S. Application Data

(60) Provisional application No. 61/758,013, filed on Jan. 29, 2013.

(51) Int. Cl.
*A61K 51/00* (2006.01)
*A61M 36/14* (2006.01)
(Continued)

(52) U.S. Cl.
CPC ........ *A61K 47/48346* (2013.01); *A61K 38/06* (2013.01); *A61K 47/48215* (2013.01);
(Continued)

(58) Field of Classification Search
CPC .............. A61K 47/00; A61K 47/48346; A61K 47/48215; A61K 47/48338;
(Continued)

(56) References Cited

U.S. PATENT DOCUMENTS

| 4,466,919 A | 8/1984 | Weingarten |
| 4,507,389 A | 3/1985 | Weingarten |

(Continued)

FOREIGN PATENT DOCUMENTS

| EP | 2 399 939 A2 | 12/2011 |
| WO | WO 01/75067 A2 | 10/2001 |

(Continued)

OTHER PUBLICATIONS

Aguilera, T.A. et al., "Systemic in vivo distribution of activatable cell penetrating peptides is superior to that of cell penetrating peptides," *Integr. Biol.*, 2009 vol. 1, pp. 371-381.
(Continued)

*Primary Examiner* — D L Jones
(74) *Attorney, Agent, or Firm* — Morgan Lewis & Bockius LLP

(57) ABSTRACT

Disclosed herein, the invention pertains to methods and compositions that find use in treatment, diagnosis, prognosis and characterization of disease and disease samples based on the ability of a disease sample to cleave a MTS molecule of the present invention. The MTS molecules of the present invention have a formula as disclosed herein and wherein A is a peptide with a sequence comprising 5 to 9 consecutive acidic amino acids, wherein the amino acids are selected from: aspartates and glutamates; B is a peptide with a
(Continued)

sequence comprising 5 to 20 consecutive basic amino acids; X and Y are linkers; P is a pre-targeting moiety; M is a macromolecular carrier, C is a detectable moiety; and T is a compound for delivery to a target, including for example a therapeutic compound.

6 Claims, 12 Drawing Sheets

(51) Int. Cl.
    *A61K 47/48*    (2006.01)
    *B82Y 5/00*    (2011.01)
    *A61K 38/06*    (2006.01)
    *A61K 49/00*    (2006.01)

(52) U.S. Cl.
    CPC .. *A61K 47/48246* (2013.01); *A61K 47/48315* (2013.01); *A61K 47/48338* (2013.01); *A61K 49/0002* (2013.01); *B82Y 5/00* (2013.01)

(58) Field of Classification Search
    CPC ...... A61K 47/483315; A61K 47/48246; A61K 49/00; A61K 49/0002; A61K 38/00; A61K 38/06; A61K 47/48315; B82Y 5/00
    USPC .......... 424/1.11, 1.65, 1.69, 1.81, 1.85, 1.89, 424/9.1, 9.2, 9.3, 9.4, 9.5, 9.6; 514/1, 514/1.1, 21.1, 21.2, 21.3, 21.4, 21.5, 21.6, 514/21.7, 21.8; 530/300, 324, 325, 326, 530/327, 328, 329, 330, 331
    See application file for complete search history.

(56) References Cited

U.S. PATENT DOCUMENTS

| | | | |
|---|---|---|---|
| 5,434,073 | A | 7/1995 | Dawson et al. |
| 5,674,980 | A | 10/1997 | Frankel et al. |
| 5,747,641 | A | 5/1998 | Frankel et al. |
| 5,910,300 | A | 6/1999 | Tournie et al. |
| 6,083,486 | A | 7/2000 | Weissleder et al. |
| 6,306,993 | B1 | 10/2001 | Rothbard et al. |
| 6,348,185 | B1 | 2/2002 | Piwnica-Worms |
| 6,592,847 | B1 | 7/2003 | Weissleder et al. |
| 7,431,915 | B2 | 10/2008 | Jiang et al. |
| 7,985,401 | B2 | 7/2011 | Jiang et al. |
| 8,110,554 | B2 | 2/2012 | Jiang et al. |
| 8,642,561 | B2 | 2/2014 | Jiang et al. |
| 9,072,792 | B2 | 7/2015 | Jiang et al. |
| 9,682,151 | B2 | 6/2017 | Tsien |
| 9,695,251 | B2 * | 7/2017 | Tsien ..................... C07K 19/00 |
| 9,808,532 | B2 | 11/2017 | Tsien |
| 2001/0021763 | A1 | 9/2001 | Harris et al. |
| 2002/0009786 | A1 | 1/2002 | Tang et al. |
| 2003/0176335 | A1 | 9/2003 | Zhang et al. |
| 2004/0009122 | A1 | 1/2004 | Klaveness et al. |
| 2004/0241096 | A1 | 12/2004 | Bogdanov et al. |
| 2005/0069494 | A1 | 3/2005 | Li et al. |
| 2005/0042034 | A1 | 5/2005 | Jiang et al. |
| 2005/0107583 | A1 | 5/2005 | Jiang et al. |
| 2006/0041105 | A1 | 2/2006 | Jiang et al. |
| 2007/0041904 | A1 | 2/2007 | Jiang et al. |
| 2009/0004118 | A1 | 1/2009 | Nie et al. |
| 2011/0160147 | A1 | 6/2011 | Dal Pozzo et al. |
| 2012/0014873 | A1 | 1/2012 | Jiang et al. |
| 2012/0134922 | A1 | 5/2012 | Tsien et al. |
| 2012/0148610 | A1 | 6/2012 | Doronina et al. |
| 2013/0020537 | A1 | 1/2013 | Maruno et al. |
| 2013/0078188 | A1 | 3/2013 | Tsien et al. |
| 2013/0176335 | A1 | 7/2013 | Sugiyama et al. |
| 2015/0031852 | A1 | 1/2015 | Liu et al. |

FOREIGN PATENT DOCUMENTS

| | | |
|---|---|---|
| WO | WO 2005/042034 A1 | 5/2005 |
| WO | WO 2006/125134 A1 | 11/2006 |
| WO | WO 2011/008992 A2 | 1/2011 |
| WO | WO 2011/008996 A2 | 1/2011 |
| WO | WO 2013/019681 A2 | 2/2013 |
| WO | WO 2014/120837 A2 | 8/2014 |

OTHER PUBLICATIONS

Bartles, J.R. et al., "Identification and charactzerization of espin, an actin-binding protein localized to the F-actin0rich junctionla plaques of Sertoli cell ectoplasmic specializations," *Journal of Cell Science*, 1996, vol. 109, No. 6, pp. 1229-1239.

Bhorade, R. et al., "Macrocyclic Chelators with Paramagnetic Cations Are Internalized into Mammalian Cells via a HIV-Tat Derived Membrane Translocation Peptide," *Bioconjugate Chemistry*, May 1, 2000, vol. 11, No. 3, pp. 301-305.

Gallwitz, M. et al., "The Extended Cleavage Specificity of Human Thrombin," *PLoS One*, Feb. 2012, vol. 7, Issue 2, e31756, pp. 1-16.

Golub et al., *Science*, Oct. 15, 1999, pp. 531-537.

Jiang, T. et al., "Tumor imaging by means of proteolytic activation of cell-penetrating peptides," *PNAS*, Dec. 21, 2004, pp. 17867-17872, vol. 101, No. 51.

Maitz, M.F. et al., "Bio-responsive polymer hydrogels homeostatically regulate blood coagulation," *Nature Communications*, 2013, pp. 1-7.

Nguyen, Q.T. et al., "Surgery with molecular fluorescence imaging using activatable cell-penetrating peptides decreases residual cancer and improves survival," *PNAS*, Mar. 2, 2010, vol. 107, No. 9, pp. 4317-4322.

Olson, E.S., "Activatable cell penetrating peptides for imaging protease activity in vivo," *Electronic Theses and Dissertations UC San Diego*, 2008, 152 pages.

Olson, E.S. et al., "In vivo characterization of activatable cell penetrating peptides for targeting protease activity in cancer," *Integr. Biol.*, 2009, vol. 1, pp. 382-393.

Olson, E.S. et al., "Activatable cell penetrating peptides linked to nanoparticles as dual probes for in vivo fluorescence and MR imaging of proteases," *PNAS*, Mar. 2, 2010, vol. 107, No. 9, pp. 4311-4316.

Olson, E.S. et al., "In vivo fluorescence imaging of atherosclerotic plaques with activatable cell-penetrating peptides targeting thrombin activity," *Integr Biol (Camb)*, Jun. 2012, vol. 4, No. 6, pp. 595-605.

Proimmune, "think peptides ® the source for all peptides for your research," 2012, pp. 1-15.

Rothbard, J. B. et al., "Conjugation of arginine oligomers to cyclosporin A facilitates topical delivery and inhibition of inflammation," *Nature Medicine*, Nov. 2000, vol. 6, No. 11, pp. 1253-1257.

Rothbard, J.B. et al., "Arginine-Rich Molecular Transporters for Drug Delivery: Role of Backbone Spacing in Cellular Uptake," *J. Med. Chem.*, 2002, vol. 45, pp. 3612-3618.

Sperling, C. et al., "Thrombin-responsive hydrogels with varied cleavage kinetics," *Society for Biomaterials*, 2013, Abstract #208, 1 page.

Tung, C-H. et al., "Arginine containing peptides as delivery vectors," *Advanced Drug Delivery Reviews*, 2003, vol. 55, pp. 281-294.

Ullrich, K.J. et al., "Controluminal para-aminohippurate (PAH) transport in the proximal tubule of the rat kidney," *Pflügers Arch.*, 1989, vol. 415, pp. 342-350.

Wang, Y. et al., "Visualizing the mechanical activation of Src," *Nature*, Apr. 21, 2005, pp. 1040-1045, vol. 434.

Wender, P.A. et al., "The design, synthesis, and evaluation of molecules that enable or enhance cellular uptake: Peptoid molcular transporters," *PNAS*, Nov. 21, 2000, vol. 97, No. 24, pp. 13003-13008.

Whitney, M. et al., "Parallel in Vivo and in Vitro Selection Using Phage Display Identifies Protease-dependent Tumor-targeting Peptides," *The Journal of Biological Chemistry*, Jul. 16, 2010, vol. 285, No. 29, pp. 22532-22541.

(56) References Cited

OTHER PUBLICATIONS

Abdollahi, A. et al., "Inhibition of $\alpha_v\beta_3$ Integrin Survival Signaling Enhances Antiangiogenic and Antitumor Effects of Radiotherapy," Clin Cancer Res., Sep. 1, 2005, 11(17), pp. 6270-6279.
Adams, S.R. et al., "Anti-tubulin drugs conjugated to anti-ErbB antibodies selectively radiosensitize," Nature Communications, Oct. 4, 2016, 7:13019, pp. 1-11.
Advani, S.J. et al., "Increased oncolytic efficacy for high-grade gliomas by optimal integration of ionizing radiation into the replicative cycle of HSV-1," Gene Therapy, 2011, vol. 18, pp. 1098-1102.
Advani, S.J. et al., "Preferential Replication of Systemically Delivered Oncolytic Vaccinia Virus in Focally Irradiated Giloma Xenografts," Clin Cancer Res., 2012; 18(9), pp. 2579-2590.
Akashi, Y. et al., "The novel microtubule-interfering agent TZT-1027 enhances the anticancer effect of radiation in vitro and in vivo," British Journal of Cancer, 2007, vol. 96, pp. 1532-1539.
Arnold, D. et al., "Substrate specificity of cathepsins D and E determined by N-terminal and C-terminal sequencing of peptide pools," Eur. J. Biochem., 1997, vol. 249, pp. 171-179.
Bai, R. et al., "Dolastatin 10, a powerful cytostatic peptide derived from a marine animal. Inhibition of tubulin polymerization mediated through the vinca alkaloid binding domain," Biochem Pharmacol., 1990; 39:1941-49.
Blum, G. et al., "Noninvasive optical imaging of cysteine protease activity using fluorescently quenched activity-based probes," Nature Chemical Biology, Oct. 2007, vol. 3, No. 10, pp. 668-677.
Breij, E.C.W. et al., "An Antibody-Drug Conjugate That Targets Tissue Factor Exhibits Potent Therapeutic Activity against a Broad Range of Solid Tumors," Cancer Res., Feb. 15, 2014, 74(4):1214-1226.
Bremer, C. et al., "In vivo molecular target assessment of matrix metalloproteinase inhibition," Nature Medicine, Jun. 2001, vol. 7, No. 6, pp. 743-748.
Bremer, C. et al., "Optical Imaging of Matrix Metalloproteinase-2 Activity in Tumors: Feasibility Study in a Mouse Model," Radiology, 2001, vol. 221, pp. 523-529.
Bremer, C. et al., "Optical Imaging of Spontaneous Breast Tumors Using Protease Sensing 'Smart' Optical Probes," Invest Radiol., Jun. 6, 2005, 40(6):321-327.
Buckel, L. et al., "Tumor Radiosensitization by Monomethyl Auristatin E; Mechanism of Action and Trageted Delivery," Cancer Res., Apr. 1, 2015, 75(7), pp. 1376-1387.
Chaurand, P. et al., "Molecular imaging of thin mammalian tissue sections by mass spectrometry," Curr Opinion Biotechnol., 2006; 17(4):431-436.
Chen, B. et al., "Thrombin Activity Associated with Neuronal Damage during Acute Focal Ischemia," The Journal of Neuroscience, May 30, 2012, vol. 32, No. 22, pp. 7622-7631.
Chen, E.I. et al., "A Unique Substrate Recognition Profile for Matrix Metalloprotinase-2," The Journal of Biological Chemistry, Feb. 8, 2002, vol. 277, No. 6, pp. 4485-4491.
Chen, J. et al., "'Zipper' Molecular Beacons: A Generalized Strategy to Optimize the Performance of Activatable Protease Probes," Bioconjugate Chem., 2009, vol. 20, pp. 1836-1842.
Cooks, R.J. et al., "Ambient Mass Spectrometry," Science, 2006; 311 (5767):1566-1570.
Crisp, J.L. et al., "Dual Targeting of Integrin $\alpha_v\beta_3$ and Matrix Metalloproteinase-2 for Optical Imaging of Tumors and Chemotherapeutic Delivery," Mol Cancer Ther., Jun. 2014, 13:6, pp. 1514-1525.
Derossi et al., "Trojan peptides: the penetratin system for intracellular delivery," Trends in Cell Biology, 1998, 8:84-87.
Doronina, S.O. et al., "Development of potent monoclonal antibody auristatin conjugates for cancer therapy," Nat Biotechnol., 2003; 21:778-84.
Egami, T. et al., "Up-regulation of integrin β3 in radioresistant pancreatic cancer impairs adenovirus-mediated gene therapy," Cancer Science, Oct. 2009, vol. 100, No. 10, pp. 1902-1907.
Fujita, M. et al., "X-ray irradiation and Rho-kinase inhibitor additively induce invasiveness of the cells of the pancreatic cancer line, MIAPaCa-2, which exhibits mesenchymal and amoeboid motility," Cancer Sci., Apr. 2011, vol. 102, No. 4, pp. 792-798.
Futaki et al., "Stearylated Arginine-Rich Peptides: A New Class of Transfection Systems," Bioconj. Chem., 2001, 12:1005-1011.
Giustini, A.J. et al., "Ionizing radiation increases systemic nanoparticle tumor accumulation," Nanomedicine 2012;8:818-21.
Hallahan, D. et al., "Integrin-mediated targeting of drug delivery to irradiated tumor blood vessels," Cancer Cell, Jan. 2003, vol. 3, pp. 63-74.
Hallahan, D.E. et al., "Radiation-mediated control of drug delivery," Am J Clin Oncol., 2001; 24:473-80.
Hallahan, D.E. et al., et al., "Spatial and temporal control of gene therapy using ionizing radiation," Nat Med., 1995;1:786-91.
Hällbrink, M. et al., "Cargo delivery kinetics of cell-penetrating peptides," Biochimica et Biophysica Acta, 2001, vol. 1515, pp. 101-109.
Harir, G. et al., "Radiation-Guided Drug Delivery to Mouse Models of Lung Cancer," Clin Cancer Res., Oct. 15, 2010, 16(1); pp. 4968-4977.
Hutteman, M. et al., "Optimization of Near-Infrared Fluorescent Sentinel Lymph Node Mapping for Vulvar Cancer," Am J Obstet Gynecol., Jan. 2012, vol. 206, No. 1, pp. 89.e1-89.e5.
Ifa, D.R. et al., "Ambient Ionization Mass Spectrometry for Cancer Diagnosis and Surgical Margin Evaluation," Clinical Chemistry, 2016, 62:1, pp. 111-123.
Jaffer, F.A. et al., "In Vivo Imaging of Thrombin Activity in Experimental Thrombi With Thrombin-Sensitive Near-Infrared Molecular Probe," Arterioscler Thromb Vasc Biol., 2002, vol. 22, pp. 1929-1935.
Joh, D.Y. et al., "Selective Targeting of Brain Tumors with Gold Nanoparticle-Induced Radiosensitization," PLoS One, Apr. 2013, vol. 8, No. 4, e62425, pp. 1-10.
Kumar, A. et al., "Increased tyoe-IV collagenase (MMP-2 and MMP-9) activity following preoperative radiotherapy in rectal cancer," British Journal of Cancer, 2000, 82(4), pp. 960-965.
Lanekoff, I. et al., "Automated Platform for High-Resolution Tissue Imaging Using Nanospray Desorption Electrospray Ionization Mass Spectrometry," Anal Chem., 2012; 84(19):8351-8356.
Laskin, J. et al., "Ambient Mass Spectrometry Imaging Using Direct Liquid Extraction Techniques," Anal. Chem., 2016; 88(1):52-73.
Levenson, R. et al., "Review Article: Modern Trends in Imaging X: Spectral imaging in preclinical research and clinical pathology," Anal Cell Pathol, 2012, vol. 35, pp. 339-361.
Levi, J. et al., "Design, Synthesis and Imaging of an Activatable Photoacoustic Probe," J Am Chem Soc., Aug. 18, 2010, vol. 132, No. 32, pp. 11264-11269.
Li, C. et al., "Tumor Irradiation Enhances the Tumor-specific Distribution of Poly(L-glutamate acid)-conjugated Paclitaxel and Its Antitumor Efficacy," Clinical Cancer Research, Jul. 2000, vol. 6, pp. 2829-2834.
Liauw, S.L. et al., "New paradigms and future challenges in radiation oncology: an update of biological targets and technology," Sci Transl Med., 2013;5:173sr2.
Lin, S.H. et al., "Opportunities and Challenges in the Era of Molecularly Targeted Agents and Radiation Therapy," J Natl Cancer Inst., 2013, vol. 105, pp. 686-693.
Linder, K.E. et al., "Synthesis, in Vitro Evaluation, and In Vivo Metabolism of Fluor/Quencher Compounds Containing IRDye 800CW and Black Hole Quencher-3 (BHQ-3)," Bioconjugate Chemistry, 2011, vol. 22, pp. 1287-1297.
Liu, F-F. et al., "Lessons Learned from Radiation Oncology Clinical Trials," Clin Cancer Res., 2013, 19(22):6089-6100.
Ma, D. et al., "Potent Antitumor Activity of an Auristatin-Conjugated, Fully Human Monoclonal Antibody to Prostate-Specific Membrane Antigen," Clin Cancer Res., 2006, 12(8):2591-2596.
Miller, S.M. et al., "Nanomedicine in chemoradiation," Ther Deliv., 2013;4: 239-50.
Moding, E.J. et al., "Strategies for optimizing the response of cancer and normal tissues to radiation," Nat Rev Drug Discov., 2013; 12:526-42.
Mullard, A., "Maturing antibody-drug conjugate pipeline hits 30," Nat Rev Drug Discov., 2013;12:329-32.

(56) References Cited

OTHER PUBLICATIONS

Nguyen, Q.T. et al., "Fluorescence-guided surgery with live molecular navigation—a new cutting edge," *Nature Reviews Cancer*, Sep. 2013, vol. 13, pp. 653-662.

Passarella, R.J. et al., "Targeted Nanoparticles That Deliver a Sustained, Specific Release of Paclitaxel to Irradiated Tumors," *Cancer Res.*, Jun. 1, 2010, 70(11); pp. 4550-4559.

Pretz, J.L. et al., "Chemoradiationtherapy: localized esophageal, gastric, and pancreatic cancer," *Surg Oncol Clin N Am.*, 2013;22:511-24.

Raleigh, D.R. et al., "Molecular targets and mechanisms of radiosensitization using DNA damage response pathways," *Future Oncol.*, 2013; 9:219-223.

Rieken, S. et al., "Targeting $\alpha_v\beta_3$ and $\alpha_v\beta_5$ inhibits photon-induced hypermigration of malignant glioma cells," *Radiation Oncology*, 2011, 6(132):pp. 1-7.

Ryppa, C. et al., "In Vitro and in Vivo Evaluation of Doxorubicin Conjugates with the Divalent Peptide E-[c(RGDfK)$_2$] that Targets Integrin $\alpha_v\beta_3$," *Bioconjugate Chem.*, 2008, vol. 19, pp. 1414-1422.

Savariar, E.N. et al., "Real-time in Vivo Molecular Detection of Primary Tumors and Metastases with Ratiometric Activatable Cell-Penetrating Peptides," *Cancer Res.*, 2012, 73(2); pp. 855-864.

Scherer, R.L. et al., "Optical imaging of matrix metalloproteinase-7 activity in vivo using a proteolytic nanobeacon," *Mol Imaging*, 2008, vol. 7, No. 3, pp. 118-131.

Sievers, E.L. et al., "Antibody-drug conjugates in cancer therapy," *Annu Rev Med.*, 2013;64:15-29.

Speake, W.J. et al., "Radiation induced MMP expression from rectal cancer is short lived but contributes to in vitro invasion," *Eur J Surg Oncol.*, 2005;31:869-74.

Stary, H. et al., "A Definition of Advanced Type of Atherosclerotic Lesions and A Histologicial Classification of Atherosclerosis: A Report From the Committee on Vascular Lesions of the Council on Arteriosclerosis, American Heart Association," *Circulation*, Sep. 1995, vol. 92, No. 5, pp. 355-374.

Stone, G.W. et al., "A Prospective Natural-History Study of Coronary Atherosclerosis," *The New England Journal of Medicine*, Jan. 20, 2011, vol. 364, No. 3, pp. 226-235.

Tishler, R.B. et al., "Taxol: a novel radiation sensitizer," *Int J Radiat Oncol Biol Phys.*, 1992; 122:613-7.

Tseng, W.W. et al., "Development of an Orthotopic Model of Invasive Pancreatic Cancer in an Immunocompetent Murine Host," *Clinical Cancer Research*, Jul. 15, 2010, vol. 16, No. 14, pp. 3684-3695.

Tsien, R.Y. et al., "Practical design criteria for a dynamic ratio imaging system," *Cell Calcium*, 1990, vol. 11, pp. 93-109.

Tsien, R.Y., "Indicators Based on Fluorescence Resonance Energy Transfer (FRET)," *Imaging in Neuroscience and Development*, Jul. 2009, vol. 4, No. 7, pp. 1-7.

Tung, C-H. et al., "A Novel Near-Infrared Fluorescence Sensor for Detection of Thrombin Activation in Blood," *ChemBioChem*, 2002, vol. 3, pp. 207-211.

Van Berkel, S.S. et al., "Fluorogenic Peptide-Based Substrates for Monitoring Thrombin Acitivity," *ChemMedChem*, 2012, vol. 7, pp. 606-617.

Van Dam, G.M. et al., "Intraoperative tumor-specific fluorescence imaging in ovarian cancer by folate receptor-$\alpha$ targeting: first in-human results," *Nature Medicine*, 2011, vol. 17, pp. 1315-1319.

Van Duijnhoven, S.M.J. et al., "Tumor Targeting of MMP-2/9 Activatable Cell-Penetrating Imaging Probes Is Caused by Tumor-Independent Activation," *J Nucl Med*, 2011, vol. 52, pp. 279-286.

Van Vlerken, L.E. et al., "Poly(ethylene glycol)-modified Nanocarriers for Tumor-targeted and Intracellular Delivery," *Pharmaceutical Research*, Aug. 2007, vol. 24, No. 8, pp. 1404-1414.

Vartak, D.G. et al., "In vitro evaluation of functional interaction of integrin $\alpha v\beta 3$ and matrix metalloprotease-2," *Mol Pharm.*, 2009, vol. 6, No. 6, pp. 1856-1867.

Wadia et al., "Protein transduction technology," *Curr. Opinion. Biotech.*, 2002, 13:52-56.

Wang, Y. et al., "Efficacy and safety of dendrimer nanoparticles with coexpression of tumor necrosis factor-$\alpha$ and herpes simplex virus thymidine kinase in gene radiotherapy of the human uveal melanoma OCM-1 cell line," *International Journal of Nanomedicine*, 2013, vol. 8, pp. 3805-3816.

Werner, M.E. et al., "Preclinical evaluation of Genexol-PM, a nanoparticle formulation of paclitaxel, as a novel radiosensitizer for the treatment of non-small cell lung cancer," *Int J Radiat Oncol Biol Phys.*, 2013;86:463-8.

Xu, W. et al., "RGD-conjugated gold nanorods induce Radiosensitization in melanoma cancer cells by down regulating $\alpha_v\beta_3$ expression," *International Journal of Nanomedicine*, 2012, vol. 7, pp. 915-924.

Zhang, L. et al., "Preparation of functionally active cell-permeable peptides by single-step ligation of two peptide modules," *Proc. Natl. Acad. Sci. USA*, Aug. 1998, vol. 95, pp. 9184-9189.

Zhu, L. et al., "Dual-Functional, Receptor-Targeted Fluorogenic Probe for In Vivo Imaging of Extracellular Protease Expressions," *Bioconjugate Chemistry*, Jun. 15, 2011, vol. 22, No. 6, pp. 1001-1005.

Znati, C. et al., "Effect of Radiation on Interstitual Fluid Pressure and Oxygenation in a Human Tumor Xenograft," *Cancer Research*, Mar. 1, 1996, vol. 56, pp. 964-968.

\* cited by examiner

FIGURE 1

Solid phase peptide synthesis and HPLC purification
↓

NH$_2$-e$_9$-c(S-StBu)-(*Substrate*)-r$_9$-c-CONH$_2$ (I)

↓ Cy5-Mal, NMM, DMSO

NH$_2$-e$_9$-c(S-StBu)-(*Substrate*)-r$_9$-c(Cy5)-CONH$_2$ (II)

↓ Et$_3$P

NH$_2$-e$_9$-c(SH)-(*Substrate*)-r$_9$-c(Cy5)-CONH$_2$ (III)

↓ PySS-PEG-Ligand, NMM, DMSO

NH$_2$-e$_9$-c(S-S-PEG-Ligand)-(*Substrate*)-r$_9$-c(Cy5)-CONH$_2$ cRGD-MMP:
Substrate= o-PLGCmeAG, Ligand= Cyc(RGDfK)
cRAD-MMP:
Substrate= o-PLGCmeAG, Ligand = Cyc(RGDfK)
cRGD-PEG6
Substrate= PEG6, Ligand = Cyc(RGDfK)
cRAD-PEG6:
Substrate= PEG6, cRGD-MMP-MMAE: Ligand = Cyclic(RGDfC)
   Substrate= o-PLGC(Me)AG-o cRAD-PEG6-MMAE: Ligand = Cyclic(RADfC)
   Substrate= PEG6-o cRGD-PEG6-MMAE: Ligand = Cyclic(RGDfC)
   Substrate= PEG6-o cRAD-MMP-MMAE: Ligand = Cyclic(RADfC)
   Substrate= o-PLGC(Me)AG-o

FIGURE 4
A
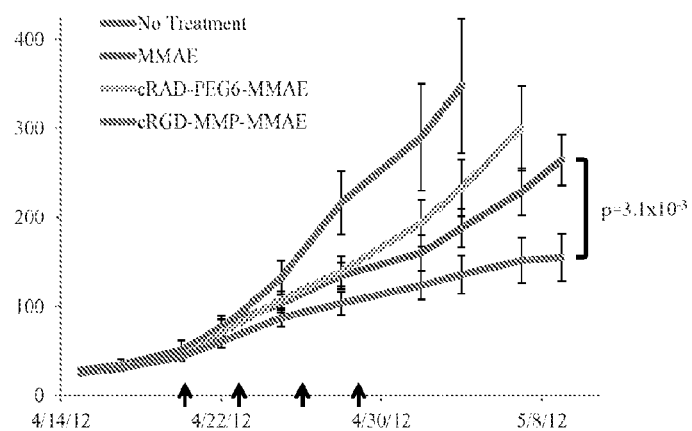
B
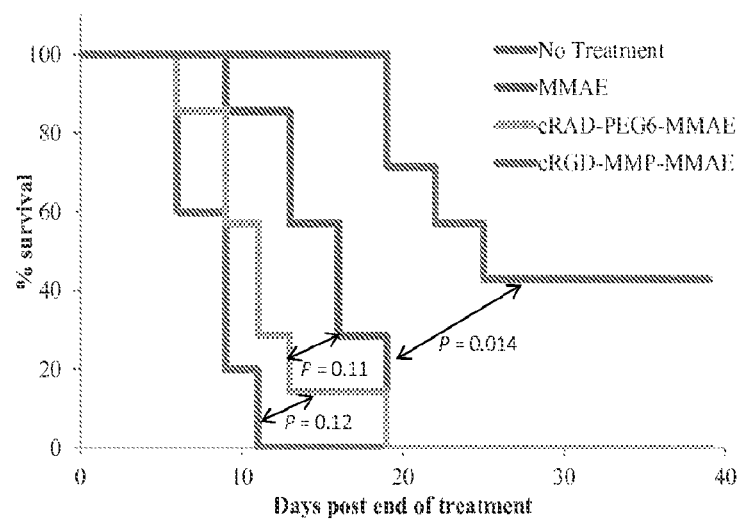

PRETARGETED ACTIVATABLE CELL PENETRATING PEPTIDE WITH INTRACELLULARLY RELEASABLE PRODRUG

STATEMENT OF FEDERALLY-SPONSORED RESEARCH

This invention was made with government support under W81XWH-09-1-0699 awarded by Army and under CA158448 awarded by National Institutes of Health. The government has certain rights in the invention.

BACKGROUND OF THE INVENTION

Introduction

Cell membranes delimit the outer boundaries of cells, and regulate transport into and out of the cell interior. Made primarily of lipids and proteins, cell membranes provide a hydrophilic surface enclosing a hydrophobic interior across which materials must pass before entering a cell. Although many small, lipophilic compounds are able to cross cell membranes passively, most compounds, particles and materials must rely on active mechanisms in order to gain entry into a living cell.

Transmembrane Transport

Regulation of transport into and out of a cell is vital for its continued viability. For example, cell membranes contain ion channels, pumps, and exchangers capable of facilitating the transmembrane passage of many important substances. However, transmembrane transport is selective: in addition to facilitating the entry of desired substances into a cell, and facilitating the exit of others, a major role of a cell membrane is to prevent uncontrolled entry of substances into the cell interior. This barrier function of the cell membrane makes difficult the delivery of markers, drugs, nucleic acids, and other exogenous material into cells.

Over the last decade, peptide sequences that can readily enter a cell have been identified. For example, the Tat protein of the human immunodeficiency virus 1 (HIV-1) is able to enter cells from the extracellular environment (e.g., Fawell et al. P.N.A.S. 91:664-668 (1994)). Such uptake is reviewed in, for example, Richard et al., J. Biol. Chem. 278(1):585-590 (2003).

Such molecules that are readily taken into cells may also be used to carry other molecules into cells along with them. Molecules that are capable of facilitating transport of substances into cells have been termed "membrane translocation signals" (MTS) as described in Tung et al., Advanced Drug Delivery Reviews 55:281-294 (2003). The most important MTS are rich in amino acids such as arginine with positively charged side chains. Molecules transported into cell by such cationic peptides may be termed "cargo" and may be reversibly or irreversibly linked to the cationic peptides. An example of a reversible linkage is found in Zhang et al., P.N.A.S. 95:9184-9189 (1994)).

MTS molecules are discussed in, for example, Wender et al., P.N.A.S. 97:1300313008 (2000); Hallbrink et al., Biochim. Biophys. Acta 1515:101-109 (2001); Derossi et al., Trends in Cell Biology 8:84-87 (1998); Rothbard et al., J Med. Chem. 45:3612-3618 (2002); Rothbard et al., Nature Medicine 6(11): 1253-1247 (2000); Wadia et al., Curr. Opinion Biotech. 13:52-56 (2002); Futaki et al; Bioconj. Chem. 12:1005-1011 (2001); Rothbard et al., U.S. Pat. No. 6,306,993; Frankel et al., U.S. Pat. No. 6,316,003; Rothbard et al., U.S. Pat. No. 6,495,663; Monahan et al., U.S. Pat. No. 6,630,351 and Jiang et al., WO 2005/042034.

Cancer Surgery

In cancer surgery, positive margins, defined as tumor cells present at the cut edge of the surgical specimen, have been associated with increased local recurrence and a poor prognosis (Haque R., et al., BMC Ear Nose Throat Disord. 16:2 (2006)). As in most solid tumors, salvage surgery (i.e., re-excision of the positive margin) or adjuvant chemotherapy and/or radiation not only cause extra trauma and expense but also often fail to remediate the poor outcome (Haque R., et al., BMC Ear Nose Throat Disord. 16:2 (2006); Singletary S. Am. J. Surg. 184:383-393 (2002); Meric F., et al., Cancer 97:926-933 (2003); Snijder R., et al., Annals of Thoracic Surg. 65 (1998); Nagtegaal I D, Quirke P., J. Clin. On. 26:303-312 (2008); Dotan Z, et al., J. Urol. 178:2308-2312 (2007); and Wieder J. A., J. Urol. 160:299-315 (1998)).

The reason for this observation is likely multifactorial and related in part to the difficulty in identifying the residual cancer during repeat surgery. Therefore, development of more sensitive imaging and diagnostic assays for more accurate detection of positive surgical margins during the primary operation would be one of the most effective means to minimize patient suffering and expense and to improve survival.

As the field of molecularly targeting fluorescent markers for early cancer detection and intraoperative margin evaluation progresses and more enzymatically activatable probes (Jiang T., et al. P.N.A.S. USA. 101:17867-17872 (2004); Aguilera T. A., et al., Integr. Biol. 1:371-381 (2009); Olson E. S., et al., Integr Biol (Camb). 1:382-393 (2009); Olson E. S., et al., PNAS USA. 107:4311-4316 (2010); Nguyen Q. T., PNAS USA. 107:4317-4322 (2010); Blum G., et al., Nat Chem Biol. 3:668-677 (2007); Gounaris E., et al., PLoS One. 3:e2916 (2008); Bremer C., et al., Invest Radiol. 40:321-327 (2005)) are becoming available for clinical use, methods such as those described herein personalized would be useful in a variety of treatment, diagnostic, prognostic applications.

As such, there remains a need in the art for additional treatment, diagnosis, prognosis and characterization, including development personalized assays, useful in both in vivo and ex vivo applications. Such methods would allow for the development of better and more personalized treatment regimens. The present invention meets these needs and provides methods for treatment, diagnosis, prognosis and characterization of tumors which can find use in a variety of personalized medicine applications.

All patents and publications, both supra and infra, are hereby incorporated by reference in their entirety.

SUMMARY OF THE INVENTION

In some embodiments, the present disclosure provides a molecule comprising the formula:

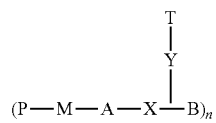

wherein the molecule comprises:
a pre-targeting moiety P;
a macromolecular carrier M;

a peptide A with a sequence comprising 5 to 9 consecutive acidic amino acids, wherein the amino acids are selected from: aspartates and glutamates;
a first cleavable linker X;
a second cleavable linker Y;
a compound T;
a peptide B with a sequence comprising 5 to 20 consecutive basic amino acids; and
n is an integer between 1 and 20.

In some embodiments of the molecule A has a sequence comprising 5 to 9 consecutive glutamates.

In some embodiments of the molecule B has a sequence comprising 5 to 12 consecutive arginines.

In some embodiments of the molecule X is selected from: DPRSFL, PPRSFL, or PLGC(Me)AG.

In some embodiments of the molecule X comprises 6-aminohexanoyl, 5-amino-3-oxapentanoyl, or a combination thereof.

In some embodiments of the molecule M is a macromolecular carrier selected from: a dendrimer, dextran, a PEG polymer, albumin, or lipid-coated perfluorocarbon droplet.

In some embodiments of the molecule M is a PEG polymer.

In some embodiments of the molecule P is cyclic RGD (cRGD).

In some embodiments of the molecule Y is Val-Cit-(p-amido)benzyloxycarbonyl.

In some embodiments of the molecule T is a therapeutic compound.

In some embodiments of the molecule T is monomethyl auristatin E (MMAE).

In some embodiments of the molecule the molecule additionally comprises an imaging agent C.

In some embodiments of the molecule C is selected from Cy5, Cy5.5, Cy7, Alexa 647, IRDYE 800CW, or a combination thereof.

In some embodiments, the present disclosure provides for a molecule comprising the formula:

(P-M-A-X—B—C)$_n$, wherein the molecule comprises:
a pre-targeting moiety P;
a macromolecular carrier M;
a peptide A with a sequence comprising 5 to 9 consecutive acidic amino acids, wherein the amino acids are selected from: aspartates and glutamates;
a first cleavable linker X;
a peptide B with a sequence comprising 5 to 20 consecutive basic amino acids;
an imaging agent C, and
n is an integer between 1 and 20.

In some embodiments of the molecule A has a sequence comprising 5 to 9 consecutive glutamates.

In some embodiments of the molecule B has a sequence comprising 5 to 12 consecutive arginines.

In some embodiments of the molecule X is selected from: DPRSFL, PPRSFL, or PLGC(Me)AG.

In some embodiments of the molecule X comprises 6-aminohexanoyl, 5-amino-3-oxapentanoyl, or a combination thereof.

In some embodiments of the molecule M is a macromolecular carrier selected from: a dendrimer, dextran, a PEG polymer, albumin, or lipid-coated perfluorocarbon droplet.

In some embodiments of the molecule M is a PEG polymer.

In some embodiments of the molecule P is cyclic RGD (cRGD).

In some embodiments of the molecule C is selected from Cy5, Cy5.5, Cy7, Alexa 647, IRDYE 800CW, or a combination thereof.

In some embodiments, the present disclosure provides a molecule comprising

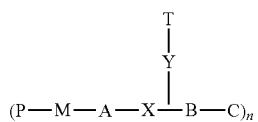

wherein the molecule comprises
a second cleavable linker Y; and
a compound T.

In some embodiments of the molecule Y is Val-Cit-(p-amido)benzyloxycarbonyl.

In some embodiments of the molecule T is a therapeutic compound.

In some embodiments of the molecule T is monomethyl auristatin E (MMAE).

In some embodiments, the present disclosure provides a molecule comprising the formula:

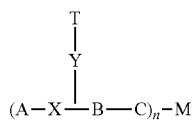

wherein the molecule comprises:
a macromolecular carrier M bound to A or B;
a peptide A with a sequence comprising 5 to 9 consecutive acidic amino acids, wherein the amino acids are selected from: aspartates and glutamates;
a first cleavable linker X;
a second cleavable linker Y;
a compound T;
a peptide B with a sequence comprising 5 to 20 consecutive basic amino acids
an imaging agent C; and
n is an integer between 1 and 20.

In some embodiments of the molecule A has a sequence comprising 5 to 9 consecutive glutamates.

In some embodiments of the molecule B has a sequence comprising 5 to 12 consecutive arginines.

In some embodiments of the molecule X is selected from: DPRSFL, PPRSFL, or PLGC(Me)AG.

In some embodiments of the molecule X comprises 6-aminohexanoyl, 5-amino-3-oxapentanoyl, or a combination thereof.

In some embodiments of the molecule M is a macromolecular carrier selected from: a dendrimer, dextran, a PEG polymer, albumin, or lipid-coated perfluorocarbon droplet.

In some embodiments of the molecule M is a PEG polymer.

In some embodiments of the molecule Y is Val-Cit-(p-amido)benzyloxycarbonyl.

In some embodiments of the molecule T is a therapeutic compound.

In some embodiments of the molecule T is monomethyl auristatin E (MMAE).

In some embodiments of the molecule C is selected from Cy5, Cy5.5, Cy7, Alexa 647, IRDYE 800CW, or a combination thereof.

In some embodiments, the present disclosure also provides methods of delivering a therapeutic agent to a cell, comprising administering to a subject a molecule according to any of the disclosed embodiments of the molecule.

In some embodiments, the cell is a cancer cell.

In some embodiments, upon binding of the molecule to a membrane receptor of the cancer cell, the therapeutic agent is delivered to the interior of the cell.

BRIEF DESCRIPTION OF THE DRAWINGS

FIG. 1 illustrates the synthesis of an exemplary pre-targeted ACPP.

FIG. 4 illustrates pre-targeted ACPP in chemotherapy by showing that cRGD ACPP MMAE out performs unconjugated drug or non-targeted uncleavable control peptide. A) Tumor growth curve obtained from MDA-MB-231 bilateral tumor bearing mice that were either intravenously injected with 6.5 nanomoles of MMAE (red line), cRAD-PEG6-MMAE (green line), cRGD-MMP-MMAE (dark blue) or no injection (no treatment, light blue). B) Kaplan-Meier survival plot on the same treatment groups shows that pre-targeted ACPP significantly (p=0.0014 compared to MMAE alone) increases the survival rate compared to other treatment groups.

DETAILED DESCRIPTION OF THE INVENTION

Introduction

Activatable cell penetrating peptides (ACPPs) are peptide based molecules in which a polycationic sequence, typically comprising 8-12 arginines, is connected via an enzyme cleavable linker to a polyanionic sequence, typically comprising a matching number of glutamates. ACPP is described in greater detail in US 2012/0134922, herein incorporated by reference.

Figure 12:
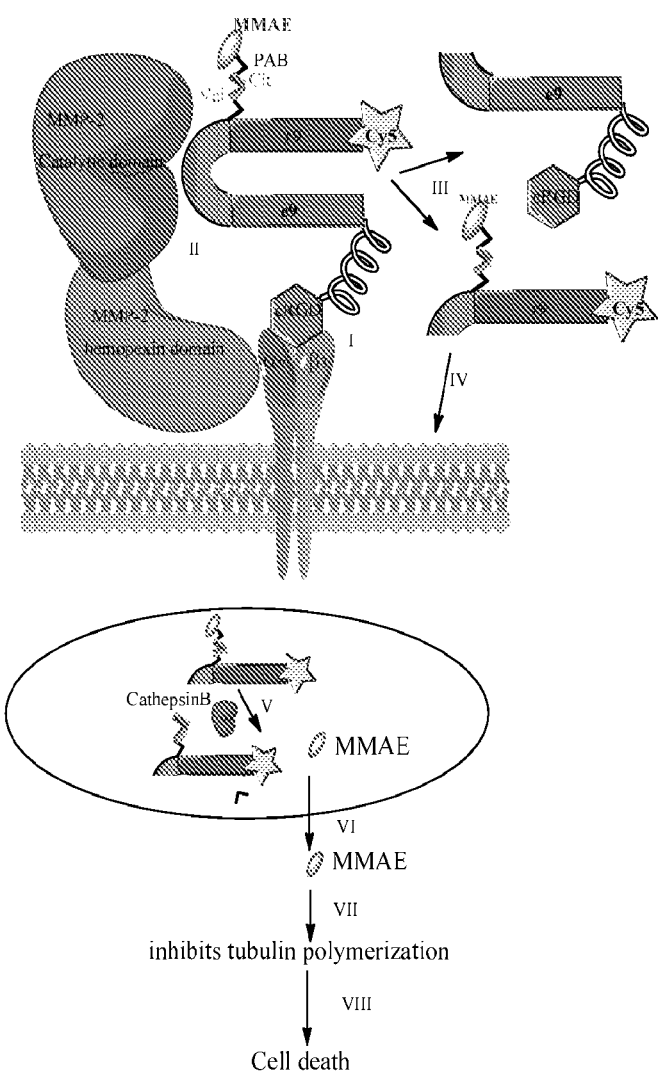
FIG. 12 illustrates a schematic representation of an embodiment of the present invention, which shows the presence of MMP-2 and $\alpha v\beta 3$ in close proximity, which enhances cleavage of ACPP. The released MMAE-r9-Cy5 fragment is taken up into endosomes and lysosomes, where the 2nd linker (zigzag line) is cleaved by enzymes such as cathepsin B to release active MMAE, which can diffuse across the organellar membranes into the cytosol where it binds extremely tightly to microtubules.

The ACPP described herein includes a first cleavable linker X that separates the acidic peptide domain from the basic peptide domain. The second cleavable linker Y is a cleavable linker linked to a compound, such as a therapeutic agent, that is preferably an intracellularly cleavable linker. The position of the second cleavable linker can be positioned anywhere along the basic peptide domain, the interface between the first cleavable marker and the basic peptide domain, or on the first cleavable linker. If the second cleavable linker is positioned on the first cleavable linker, it should be positioned such that following cleavage of the first cleavable linker, the second cleavable linker and its associated cargo remains associated with the basic peptide domain to allow delivery of the cargo into the cell, and does not interfere with the cleavage of the first cleavable linker (see, e.g. FIG. 12).

Disclosed is a new sub class of ACPP that accommodates 1) pretargeting agent/ligand, 2) prodrug attached by a linker cleavable after endocytosis, and 3) contrast or imaging agent. This allows ACPP to be used as a molecular dual targeted theranostic agent. The pre-targeted ACPP embodiments described herein synergistically enhance tumor contrast, reduce tumor growth, and enhance the overall survival rate in a patient in need thereof.

The present invention is also based in part on the discovery that ex vivo cleavage of ratiometric MTSs (ACPPs) by tumor extract correlates with in-vivo MTS (ACPP) fluorescence uptake and increased emission ratio in cancer, particularly carcinoma. In some embodiments, measuring the ability of individual tumors to cleave MTSs (ACPPs) and assessing the percentage of enzymatically positive tumors in a clinical population provides valuable data in that the ex vivo cleavage data can be correlated with MTS (ACPP) performance in vivo. In some embodiments, the ex vivo cleavage assay may be further developed into a personalized screening assay to determine eligibility to use MTSs (ACPPs) during a given patient procedure such as for example surgery. In some embodiments, the present invention provides methods for assessing the distribution of human surgical specimens with respect to their ability to cleave the MTSs (ACPPs) and the correlation of the MTS with clinical grade and outcome. Methods and compositions useful in such methods are provided herein.

CERTAIN DEFINITIONS

The following terms have the meanings ascribed to them unless specified otherwise.

The terms cell penetrating peptide (CPP), activatable cell penetrating peptide (ACPP), membrane translocating sequence (MTS) and protein transduction domain are used interchangeably. As used herein, the terms mean a peptide (polypeptide or protein) sequence that is able to translocate across the plasma membrane of a cell. In some embodiments, a CPP facilitates the translocation of an extracellular molecule across the plasma membrane of a cell. In some embodiments, the CPP translocates across the plasma membrane by direct penetration of the plasma membrane, endocytosis-mediated entry, or the formation of a transitory structure. In some embodiments the MTS is not transported across the membrane of a cell, but is employed in an ex vivo assay or application.

As used herein, the term "aptamer" refers to a DNA or RNA molecule that has been selected from random pools based on their ability to bind other molecules with high affinity specificity based on non-Watson and Crick interactions with the target molecule (see, e.g., Cox and Ellington, *Bioorg. Med. Chem.* 9:2525-2531 (2001); Lee et al., Nuc. Acids Res. 32:D95-D100 (2004)). In some embodiments, the aptamer binds nucleic acids, proteins, small organic compounds, vitamins, inorganic compounds, cells, and even entire organisms.

The terms "polypeptide," "peptide" and "protein" and derivatives thereof as used herein, are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds. As used herein, the terms "peptide" refers to a polymer of amino acid residues typically ranging in length from 2 to about 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 8, 9, 10, 11, or 12 residues to about 15, 20 or 25 residues. Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, *Chem. Biochem. Amino Acids and Proteins* 7: 267-357 (1983)), where the amide is replaced with a saturated amine (see, e.g., Skiles et al., U.S. Pat. No. 4,496,542, which is incorporated herein by reference, and Kaltenbronn et al., (1990) Pp. 969-970 in *Proc. 11th American Peptide Symposium*, ESCOM Science Publishers, The Netherlands, and the like)).

The term "amino acid" and derivatives thereof as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be either D amino acids or L amino acids. In peptide sequences throughout the specification, lower case letters indicate the D isomer of the amino acid (conversely, upper case letters indicate the L isomer of the amino acid).

Amino acids may be referred to herein by either their commonly known three letter symbols or by the one-letter symbols recommended by the IUPAC-IUB Biochemical Nomenclature Commission.

Nucleotides, likewise, may be referred to by their commonly accepted single-letter codes.

One of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

As used herein, a "linker" or "spacer" is any molecule capable of binding (e.g., covalently) portions an MTS molecule as disclosed herein together. Linkers include, but are not limited to, straight or branched chain carbon linkers, heterocyclic carbon linkers, peptide linkers, polyether linkers and short hydrophilic molecules. Exemplary linkers can include but are not limited to NH—CH$_2$—CH$_2$—O—CH$_2$—CO— and 5-amino-3-oxopentanoyl. For example, poly(ethylene glycol) linkers are available from Quanta Biodesign, Powell, Ohio. These linkers optionally have amide linkages, sulfhydryl linkages, or heterofunctional linkages.

As used herein, the term "label" refers to any molecule that facilitates the visualization and/or detection of a MTS molecule disclosed herein. In some embodiments, the label is a fluorescent moiety.

The term "carrier" or "macromolecular carrier" means an inert molecule that increases (a) plasma half-life and (b) solubility. In some embodiments, a carrier increases plasma half-life and solubility by reducing glomerular filtration. In some embodiments, a carrier increases tumor uptake due to enhanced permeability and retention (EPR) of tumor vasculature. Exemplary macromolecular carriers include but are not limited to dendrimers, dextrans, PEG polymers, albumins, or lipid-coated perfluorocarbon droplets.

The term "thrombin" means an enzyme (EC 3.4.21.5) that cleaves fibrinogen molecules into fibrin monomers. Thrombin, acting through its G-protein coupled receptor PAR-I, is a key player in a wide range of vascular and extravascular disease processes throughout the body, including cancer, cardiovascular diseases, acute kidney injury, and stroke. In certain instances, thrombin activity increases over the course of atherosclerotic plaque development. In some embodiments, thrombin activity is a biomarker for atherosclerotic plaque development.

The term "reactive oxygen species" or "ROS" includes peroxide compounds or compounds with peroxide activity. Examples include but are not limited to hydrogen peroxide. Hydrogen peroxide is represented by the formula $H_2O_2$. Hydrogen peroxide is commonly found endogenously in living organisms. $H_2O_2$ plays an active role in the regulation of various physiological processes; however, its overabundance results in oxidative stress that can lead to extensive cellular damage. Indeed, high levels of $H_2O_2$ have been implicated in many pathological conditions including inflammation, diabetes, cardiovascular diseases, neurodegenerative disorders and cancer.

The terms "individual," "patient," or "subject" are used interchangeably. As used herein, they mean any mammal (i.e., species of any orders, families, and genus within the taxonomic classification animalia: chordata: vertebrata: mammalia). In some embodiments, the mammal is a human. None of the terms require or are limited to situation characterized by the supervision (e.g., constant or intermittent) of a health care worker (e.g., a doctor, a registered nurse, a nurse practitioner, a physician's assistant, an orderly, or a hospice worker).

As used herein, the term "medical professional' means any health care worker. By way of non-limiting example, the health care worker may be a doctor, a registered nurse, a nurse practitioner, a physician's assistant, an orderly, or a hospice worker.

The terms "administer," "administering", "administration," and derivatives thereof as used herein, refer to the methods that may be used to enable delivery of agents or compositions to the desired site of biological action These methods include, but are not limited to parenteral injection (e.g., intravenous, subcutaneous, intraperitoneal, intramuscular, intravascular, intrathecal, intravitreal, infusion, or local) Administration techniques that are optionally employed with the agents and methods described herein, include e.g., as discussed in Goodman and Gilman, *The Pharmacological Basis of Therapeutics*, current edition, Pergamon, and Remington's, Pharmaceutical Sciences (current edition), Mack Publishing Co, Easton, Pa.

The term "pharmaceutically acceptable" and derivatives thereof as used herein, refers to a material that does not abrogate the biological activity or properties of the agents described herein, and is relatively nontoxic (i.e., the toxicity of the material significantly outweighs the benefit of the material) In some instances, a pharmaceutically acceptable material may be administered to an individual without causing significant undesirable biological effects or significantly interacting in a deleterious manner with any of the components of the composition in which it is contained.

The term "surgery" and derivatives thereof as used herein, refers to any methods for that may be used to manipulate, change, or cause an effect by a physical intervention These methods include, but are not limited to open surgery, endoscopic surgery, laparoscopic surgery, minimally invasive surgery, and robotic surgery.

The terms "neoplasm" or "neoplasia" and derivatives thereof as used herein, include any non-normal or non-standard cellular growth. Neoplasms can include tumors and cancers of any variety of stages, from benign to metastatic. Neoplasms can be primary or metastatic growths and can occur anywhere in a subject. Neoplasms can include neoplasms of the lung, skin, lymph, brain, nerves, muscle, breast, prostate, testis, pancreases, liver, kidneys, stomach, muscle, bone and blood. Neoplasms can be solid and non-solid tumors.

The terms "sample" or "samples" and derivatives thereof as used herein, include any samples obtained from a subject with can be employed with the methods described herein. Samples can include but are not limited to urine, blood, lymph, tears, mucus, saliva, biopsy or other sample tissue samples. Sample can be frozen, refrigerated, previously frozen, and/or stored for minutes, hours, days, weeks, months, years. Sampling techniques, handling and storage are well known and any such techniques for obtaining samples for use with the present invention are contemplated.

The following symbols, where used, are used with the indicated meanings Fl=fluorescein, aca=ahx=X=aminohexanoyl linker (—HN—$(CH_2)_5$CO-) aminohexanoyl, C=L-cysteine, E=L-glutamate, R=L-arginine, D=L-aspartate, K=L-lysine, A=L-alanine, r=D-arginine, c=D-cysteine, e=D-glutamate, P=L-proline, L=L-leucine, G=glycine, V=valine, I=isoleucine, M=methionine, F=phenylalanine, Y=tyrosine, W=tryptophan, H=histidine, Q=glutamine, N=asparagine, S=serine, T=threonine, o is 5-amino-3-oxapentanoyl linker, and C(me) is S-methylcysteine.

MTS Peptides

In some embodiments, a generic structure for peptides having features of the invention are selected from the following:

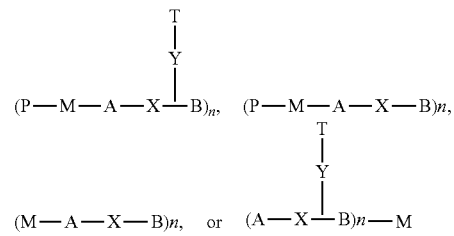

where P is a pre-targeting moiety; M is a macromolecular carrier; T is a compound for delivery to a target, including for example a therapeutic compound; peptide portion B includes between about 5 to about 20 basic amino acids; X is a cleavable linker portion, in some embodiments cleavable under physiological conditions; Y is a cleavable linker portion, in some embodiments cleavable under physiological conditions; and wherein peptide portion A includes between about 2 to about 20 acidic amino acids. In some embodiments of molecules having features of the invention, peptide portion B includes between about 5 to about 20, or between about 9 to about 16 basic amino acids, and may be a series of basic amino acids (e.g., arginines, histidines, lysines, or other basic amino acids). In some embodiments of molecules having features of the invention, peptide portion A includes between about 2 to about 20, or between about 5 to about 20 acidic amino acids, and may be series of acidic amino acids (e.g., glutamates and aspartates or other acidic amino acids). A schematic representation of a MTS molecule having features of the invention comprising a basic portion B, a linker portion X, and an acidic portion A is presented in FIG. 1A of WO 2005/042034. In embodiments, MTS molecules having features of the invention may be cyclic molecules, as schematically illustrated in FIG. 1B of WO 2005/04203. Thus, MTS molecules having features of the invention may be linear molecules, cyclic molecules, or may be linear molecules including a cyclic portion.

In some embodiments, A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X is a linker that is cleavable by a protease.

In some embodiments, A is a peptide with a sequence comprising 5 to 9 consecutive acidic amino acids, wherein the amino acids are selected from: aspartates and glutamates; B is a peptide with a sequence comprising 5 to 20 consecutive basic amino acids; X is a linker that is cleavable by thrombin; and M is a macromolecular carrier.

Regulation of transport into and out of a cell is important for its continued viability. For example, cell membranes contain ion channels, pumps, and exchangers capable of facilitating the transmembrane passage of many important substances. However, transmembrane transport is selective in addition to facilitating the entry of desired substances into a cell, and facilitating the exit of others, a major role of a cell membrane is to prevent uncontrolled entry of substances into the cell interior. This barrier function of the cell membrane makes difficult the delivery of markers, drugs, nucleic acids, and other exogenous material into cells.

As discussed above, molecules including a multiple basic amino acids, such as a series of basic amino acids, are often taken up by cells. However, the present inventors have discovered that molecules having structures including a basic portion B, a linker portion X and/or Y and an acidic portion A are not taken up by cells. An acidic portion A may include amino acids that are not acidic. Acidic portion A may comprise other moieties, such as negatively charged moieties. In some embodiments acidic portion A does not include an amino acid. In embodiments of MTS molecules having features of the present disclosure, an acidic portion A may be a negatively charged portion, in some embodiments having about 2 to about 20 negative charges at physiological pH. A basic portion B may include amino acids that are not basic. Basic portion B may comprise other moieties, such as positively charged moieties. In some embodiments basic portion B does not include an amino acid. In embodiments of MTS molecules having features of the invention, a basic portion B may be a positively charged portion, having between about 5 and about 20 positive charges at physiological pH. Including an acidic portion A is effective to inhibit or prevent the uptake of a portion B into cells. Such a block of uptake that would otherwise be effected by the basic amino acids of portion B may be termed a "veto" of the uptake by the acidic portion A. The present inventors have made the further surprising discovery that cleavage of linker X, allowing the separation of portion A from portion B is effective to allow the uptake of portion B into cells.

In a some embodiments, MTS molecules of the present disclosure include the following:

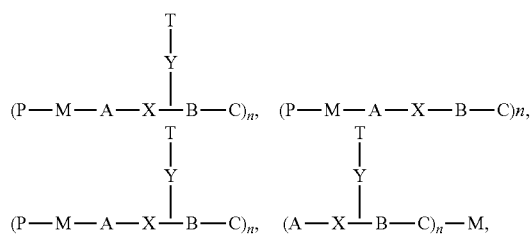

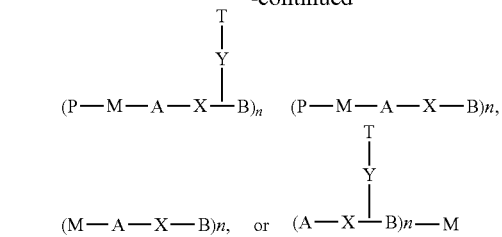

wherein P is a pre-targeting moiety; M is a macromolecular carrier, T is a compound for delivery to a target, including for example a therapeutic compound; A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound; and n is an integer between 1 and 20; and C is a detectable cargo moiety. An acidic portion A may include amino acids that are not acidic. In some embodiments, A-X-B is joined to T with linker Y. Acidic portion A may comprise other moieties, such as negatively charged moieties. In some embodiments, cleavage of linker X leads to B and T remaining joined together. In some embodiments, B and T remained joined together until cleavage of linker Y occurs. In embodiments of MTS molecules having features of the invention, an acidic portion A may be a negatively charged portion, having about 2 to about 20 negative charges at physiological pH that does not include an amino acid. A basic portion B may include amino acids that are not basic. Basic portion B may comprise other moieties, such as positively charged moieties. In some embodiments basic portion B does not include an amino acid. In embodiments of MTS molecules having features of the invention, a basic portion B may be a positively charged portion, having between about 5 and about 20 positive charges at physiological pH. In some embodiments, the amount of negative charge in portion A is approximately the same as the amount of positive charge in portion B.

A cargo moiety C (also referred to as a detectable moiety) and or compound T include, for example, a variety of detectable agents, including for example any detectable moiety for detection in an ex vivo assay, a contrast agent for diagnostic imaging, or a chemotherapeutic drug or radiation-sensitizer for therapy. B may be, for example, a peptide portion having between about 5 to about 20 basic amino acids, such as a series of basic amino acids (arginines are can be employed, as well as histidines, lysines or other basic amino acids). In some embodiments, X and/or Y is a cleavable linker that is cleavable under physiological conditions. A may be a peptide portion having between about 2 to about 20 about 2 to about 20 acidic amino acids, such as a series of acidic amino acids. In some embodiments of molecules having features of the invention, glutamates and aspartates are employed as acidic amino acids for peptide portion A.

A pre-targeting moiety P can include a variety of peptides for use in targeting the MTS molecules of the invention to a particular tissue, cell type and/or cell. A pre-targeting moiety P includes any moiety capable of binding a moiety on a target cell or in target cell location, including for example peptide moieties, antibodies, aptamers, chemical ligands, small molecule ligands, peptides, nucleotides/nucleic acids, peptide nucleic acids, locked nucleic acids and small molecule moieties as well as any derivatives thereof. In some embodiments, P includes any moiety capable of binding to cell and/or tissue involved in inflammation, diabetes, cardiovascular diseases, neurodegenerative disorders and cancer. In some embodiments, the receptor for which P is a legend can include any receptor differentially expressed on a neoplastic cell as compared to a non-neoplastic cell, including breast, prostate, liver, colon, lung, pancreas, stomach, brain, liver, kidney, bladder, blood or any other receptor known by those of skill in the art to be differentially expressed in cancer versus normal cells. In some embodiments, the receptor to which P is a ligand includes a receptor selected from but not limited to G-protein coupled receptors (GPCRs), androgen receptors (ARs), estrogen receptors (ERs), leptin receptors (LRs), growth hormone receptors (GHRs), transforming growth factor receptors (TGFs; including for example but not limited to TGFβ1, TGFβ2 and TGFβ3), epidermal growth factor receptors (EGFRs), HER2/neu receptors, breast cancer associated receptors (including for example but not limited to BRCA1 and BRCA2 receptors), ErbB receptors, ErbB2 receptors, epidermal growth factor receptors (EGFRs), insulin like growth factor receptors (ILGFRs), HGF/Met receptors, tyrosine kinase receptors, pattern recognition receptors (PRRs), Toll-like receptors (TLRs) pathogen-associated molecular patterns (PAMP), killer activated and killer inhibitor receptors (KARs and KIRs), complement receptors, Fc receptors, B-cell receptors, T-cell receptors, cytokine receptors, RAGE, BTLA, protease activate receptors (PARs), nuclear receptors (including for example but not limited to PPARs), mineralocorticoid receptors, platelet ADP receptors, APJ receptor, muscarinic receptors (including for example but not limited to muscarinic acteylcholine receptor M2, M3 muscarinic receptor), glucorticoid receptors, adrenergic receptors, scavenger receptors, calcium sensing receptor (CaR), angiotension II receptor, bile acid receptors, corticosteroid receptors, Protease-activated receptors (PARs), interleukin receptors (including for example, but not limited to interleukin 1 receptors), AMPA receptors, insulin receptors, glucose receptors, cannabinoid receptors, chemokine receptors, N-methyl-D-aspartate (NDMA) receptors, adenosine receptors, peripheral benzodiazepine receptors, sigma-1 receptor, Trk receptors (including for example but not limited to TrkB receptor), nuclear hormone receptors, nicotinic receptors, nicotinic acetylcholine receptors (including for example but not limited to α4β2 and IgG receptors) and integrins. In some embodiments, P is a ligand for capable of binding to αvβ3 or αvβ5. In some embodiments, P is a ligand capable of binding to αvβ3. In some embodiments, P is a cyclic ligand. In some embodiments, P is cyclic RGD (cRGD).

The present inventors have made the surprising discovery that including an acidic portion A is also effective to inhibit or prevent the uptake into cells of molecules combining a portion B and a portion C and/or compound T. The present inventors have made the further discovery that cleavage of linker X and/or Y, allowing the separation of portion A from portion B is effective to allow the uptake of portions B and C into cells. Thus, delivery of cargo C can be controlled and enhanced by molecules having features of the invention.

For example, when peptide portion A contains about 5 to about 9 consecutive glutamates or aspartates, and X and/or Y is a flexible linker of about 2 to about 100, or about 6 to about 30 atoms in length, the normal ability of a peptide portion B (e.g., a sequence of nine consecutive arginine residues) to cause uptake into cells is blocked. Cleavage of linker X allows the separation of portion A from portion B and portion C and/or compound T, alleviating the veto by portion A. Thus, when separated from A, the normal ability of portion B to affect the uptake of cargo C into cells is regained. Such cellular uptake typically occurs near the location of the cleavage event. Thus, design of cleavable linker X and/or Y such that either is cleaved at or near a target cell is effective to direct uptake of cargo C and/or therapeutic moiety T into target cells. Extracellular cleavage of X and/or Y allows separation of A from the rest of the molecule to allow uptake into cells.

A MTS molecule having features of the invention may be of any length. In embodiments of MTS molecules having features of the invention, a MTS molecule may be about 7 to about 40 amino acids in length, not including the length of a linker X and/or Y, a cargo portion C and/or a moiety T. In other embodiments, particularly where multiple non-acidic (in portion A) or non-basic (in portion B) amino acids are included in one or both of portions A and B, portions A and B of a MTS molecule may together be about 50, or about 60, or about 70 amino acids in length. A cyclic portion of an MTS may include about 12 to about 60 amino acids, not including the length of a linker X and a cargo portion C. For example, a linear MTS molecule having features of the invention may have a basic portion B having between about 5 to about 20 basic amino acids (in some embodiments between about 9 to about 16 basic amino acids) and an acidic portion A having between about 2 to about 20 acidic amino acids (e.g., between about 5 to about 20, between about 5 to about 9 acidic amino acids). In some embodiments, a MTS molecule having features of the invention may have a basic portion B having between about 9 to about 16 basic amino acids and between about 5 to about 9 acidic amino acids.

Portions A and B may include either L-amino acids or D-amino acids. In embodiments of the invention, D-amino acids are employed for the A and B portions in order to minimize immunogenicity and nonspecific cleavage by background peptidases or proteases. Cellular uptake of oligo-D-arginine sequences is known to be as good or better than that of oligo-L-arginines. The generic structures of the molecules described above can be effective where A is at the amino terminus and where A is at the carboxy terminus, i.e. either orientation of the peptide bonds is permissible. However, in embodiments where X and/or Y is a peptide cleavable by a protease, it may be beneficial to join the C-terminus of X and/or Y to the N-terminus of B, so that the new amino terminus created by cleavage of X and/or Y contributes an additional positive charge that adds to the positive charges already present in B.

In some embodiments, a MTS molecule disclosed herein has the formula according to one of the following:

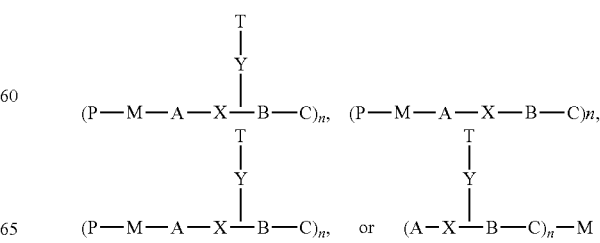

wherein C is a cargo moiety; T is a therapeutic moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X and/or Y is a linker that is cleavable by thrombin. In some embodiments, the acid amino acids are consecutive. In some embodiments, the acid amino acids are not consecutive.

In some embodiments, a MTS molecule disclosed herein has the formula according to one of the following:

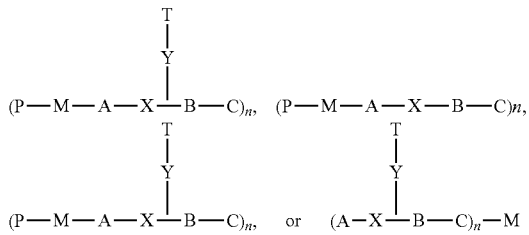

wherein C is a cargo moiety; T is a therapeutic moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X and/or Y is a linker that is cleavable by thrombin; M is a macromolecular carrier; and n is an integer between 1 and 20.

In some embodiments of molecules having features of the invention, peptide portion A includes between about 2 to about 20, or between about 5 to about 20 acidic amino acids, and may be series of acidic amino acids (e.g., glutamates and aspartates or other acidic amino acids). In some embodiments, A has a sequence comprising 5 to 9 consecutive glutamates. In some embodiments, portion A comprises 8 consecutive glutamates (i.e., EEEEEEEE or eeeeeeee).

An acidic portion A may include amino acids that are not acidic. Acidic portion A may comprise other moieties, such as negatively charged moieties. In embodiments of a MTS molecule disclosed herein, an acidic portion A may be a negatively charged portion, in some embodiments having about 2 to about 20 negative charges at physiological pH that does not include an amino acid. In some embodiments, the amount of negative charge in portion A is approximately the same as the amount of positive charge in portion B.

Portion A is either L-amino acids or D-amino acids. In embodiments of the invention, D-amino acids are can be employed in order to minimize immunogenicity and non-specific cleavage by background peptidases or proteases. Cellular uptake of oligo-D-arginine sequences is known to be as good as or better than that of oligo-L-arginines.

It will be understood that portion A may include non-standard amino acids, such as, for example, hydroxylysine, desmosine, isodesmosine, or other non-standard amino acids. Portion A may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion A may also include peptide mimetic moieties, including portions linked by non-peptide bonds and amino acids linked by or to non-amino acid portions.

The generic structures according to one of the following:

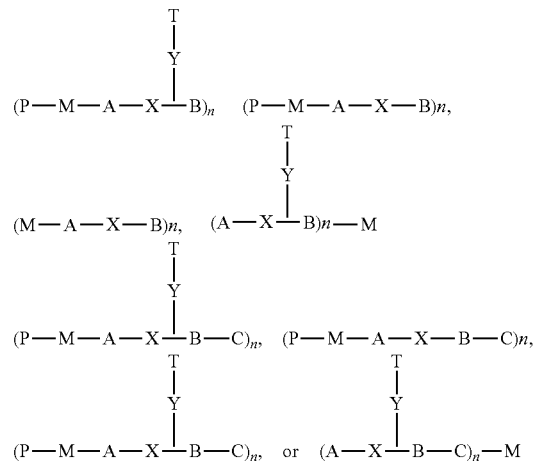

is effective where A is at the amino terminus or where A is at the carboxy terminus, i.e., either orientation of the peptide bonds is permissible.

In some embodiments, a MTS molecule disclosed herein has the formula according to one of the following:

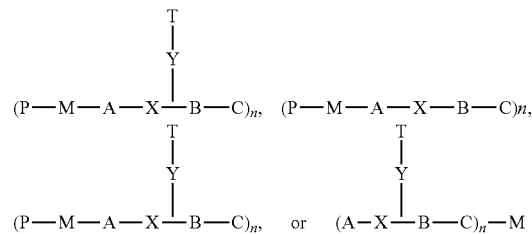

wherein C is a cargo moiety, A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X and/or Y is a linker that is cleavable by thrombin.

In some embodiments, a MTS molecule disclosed herein has the formula according to one of the following

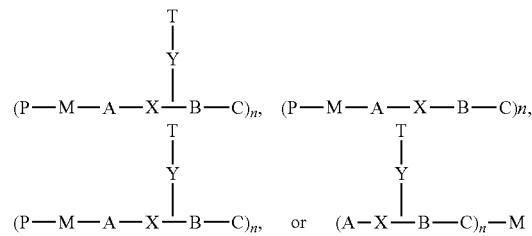

wherein C is a cargo moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X and/or Y is a linker that is cleavable by thrombin; M is a macromolecular carrier; and n is an integer between 1 and 20.

In some embodiments of molecules having features of the disclosure, peptide portion B includes between about 5 to about 20, or between about 9 to about 16 basic amino acids, and may be a series of basic amino acids (e.g., arginines, histidines, lysines, or other basic amino acids). In some embodiments, portion B comprises 9 consecutive arginines (i.e., RRRRRRRRR or rrrrrrrrr). In some embodiments, the basic amino acids are consecutive. In some embodiments, the basic amino acids are not consecutive.

A basic portion B may include amino acids that are not basic. Basic portion B may comprise other moieties, such as positively charged moieties. In embodiments, a basic portion B may be a positively charged portion, having between about 5 and about 20 positive charges at physiological pH that does not include an amino acid. In some embodiments, the amount of negative charge in portion A is approximately the same as the amount of positive charge in portion B.

Portion B is either L-amino acids or D-amino acids. In some embodiments of the invention, D-amino acids are employed in order to minimize immunogenicity and non-specific cleavage by background peptidases or proteases. Cellular uptake of oligo-D-arginine sequences is known to be as good as or better than that of oligo-L-arginines.

It will be understood that portion B may include non-standard amino acids, such as, for example, hydroxylysine, desmosine, isodesmosine, or other non-standard amino acids. Portion B may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. Portion B may also include peptide mimetic moieties, including portions linked by non-peptide bonds and amino acids linked by or to non-amino acid portions.

In embodiments where X and/or Y is a peptide cleavable by a protease, it may be beneficial to join the C-terminus of X and/or Y to the N-terminus of B, so that the new amino terminus created by cleavage of X and/or Y contributes an additional positive charge that adds to the positive charges already present in B.

Cargo portion C may be attached to B in any location or orientation. A cargo portion C need not be located at an opposite end of portion B than a linker X and/or Y. Any location of attachment of C to B is acceptable as long as that attachment remains after X and/or Y is cleaved. For example, a cargo portion C may be attached to or near to an end of portion B with linker X and/or Y attached to an opposite end of portion B. A cargo portion C may also be attached to or near to an end of portion B with linker X and/or Y attached to or near to the same end of portion B. In some embodiments of the invention, a linker X and/or Y may link to a cargo portion C which is linked to a basic portion B where a MTS molecule having features of the invention comprising a cargo portion C linked to multiple basic portions B, each of which basic portions B are linked to a linker portion X and/or Y, and via the linker to an acidic portion A.

A linker X and/or Y may be designed for cleavage in the presence of particular conditions or in a particular environment. In some embodiments, a linker X and/or Y is cleavable under physiological conditions. Cleavage of such a linker X and/or Y may, for example, be enhanced or may be affected by particular pathological signals or a particular environment related to cells in which cargo delivery is desired. The design of a linker X and/or Y for cleavage by specific conditions, such as by a specific enzyme, allows the targeting of cellular uptake to a specific location where such conditions obtain. Thus, one important way that MTS molecules having features of the invention provide specific detection of specific proteases presence is by the design of the linker portion X and/or Y to be cleaved by the protease. Thus, another important way that MTS molecules having features of the invention provide specific detection of hydrogen peroxide presence is by the design of the linker portion X and/or Y to be cleaved by hydrogen peroxide. The linker portion X and/or Y can be designed to be cleaved only by specific proteases or to be selective for specific proteases. After cleavage of a linker X and/or Y, the portions B-C of the molecule are then a simple conjugate of B and C, in some instances retaining a relatively small, inert stub remaining from a residual portion of linker X and/or Y.

A linker portion X and/or Y may be cleavable by conditions found in the extracellular environment, such as acidic conditions which may be found near cancerous cells and tissues or a reducing environment, as may be found near hypoxic or ischemic cells and tissues; by proteases or other enzymes found on the surface of cells or released near cells having a condition to be treated, such as diseased, apoptotic or necrotic cells and tissues; or by other conditions or factors. An acid-labile linker may be, for example, a cis-aconitic acid linker. A linker portion X and/or Y may also be cleaved extracellularly in an ex vivo reaction. Other examples of pH-sensitive linkages include acetals, ketals, activated amides such as amides of 2,3-dimethylmaleamic acid, vinyl ether, other activated ethers and esters such as enol or silyl ethers or esters, imines, iminiums, enamines, carbamates, hydrazones, and other linkages. A linker X may be an amino acid or a peptide. A linker portion X and/or Y may also be cleaved by hydrogen peroxide found in the extracellular environment, which can occur near and around cells during inflammation, diabetes, cardiovascular diseases, neurodegenerative disorders and cancer. A peptide linker may be of any suitable length, such as, for example, about 3 to about 30, or about 6 to about 24 atoms in sequence (e.g., a linear peptide about 1 to 10 or about 2 to 8 amino acids long). A cleavable peptide linker may include an amino acid sequence recognized and cleaved by a protease, so that proteolytic action of the protease cleaves the linker X and/or Y. A cleavable peptide linker may include an amino acid sequence recognized and cleaved by a hydrogen peroxide, so that hydrogen peroxide action cleaves the linker X and/or Y.

In some embodiments, X and/or Y is a cleavable linker. In some embodiments, a linker X and/or Y is designed for cleavage in the presence of particular conditions or in a particular environment In some embodiments, a linker X and/or Y is cleavable under physiological conditions Cleavage of such a linker X and/or Y may, for example, be enhanced or may be affected by particular pathological signals or a particular environment related to cells in which cargo delivery is desired The design of a linker X and/or Y for cleavage by specific conditions, such as by a specific enzyme (e.g., thrombin), allows the targeting of cellular uptake to a specific location where such conditions obtain Thus, one important way that MTS molecules provide specific targeting of cellular uptake to desired cells, tissues, or regions is by the design of the linker portion X and/or Y to be cleaved by conditions near such targeted cells, tissues, or regions. After cleavage of a linker X and/or Y, the portions B-C, B-C with T, or B with T of the molecule are then a simple conjugate of the recited parts, in some instances retaining a relatively small, inert stub remaining from a residual portion of linker X and/or Y.

In some embodiments, X and/or Y is cleavable by a protease associated with a disease, including but not limited to inflammation, diabetes, cardiovascular diseases, neurodegenerative disorders and cancer. In some embodiments, X and or Y is cleavable by a matrix metalloproteinase (including but not limited to MMP-2, MMP-9, MMP-7 and MMP-14), a hydrogen peroxidase, cathepsins (including but not limited to cathepsin B and cathepsin K), serine proteases (including but not limited to neutrophil serine proteases), mast cell proteases, elastases, gelatinases (including but not limited to MMP-2/gelatinase A and MMP-9/92-kDa gelatinase B), collagenases (including but not limited to MMP-1, MMP-3, MMP-8, and MMP-13), stromelysins (including but not limited to MMP-3, -7, -10, -11, and -12), tissue inhibitors of metalloproteinases (TIMPs; including but not limited to TIMP-1 and TIMP-2) cysteine proteases, threonine proteases, aspartic proteases, thrombin, plasmin, PSA, trypsin, uPA, TOP, caspase (including but not limited to caspase-3), β-amyloid proteases, calpains, and presenilinases. For a description of proteases, see, for example, Choi et al., *Theranostics*, 2(2): 156-178 (2012); incorporated herein by reference in its entirety.

In some embodiments, X and/or Y is DPRSFL, PPRSFL, PLGC(Me)AG, 6-aminohexanoyl, 5-amino-3-oxapentanoyl, Val-Cit-(p-amido)benzyloxycarbonyl (Val-Cit-PAB), benzyloxycarbonyl-valine-citrulline (Z-val-cit), or a combination thereof. In some embodiments, X is DPRSFL, PPRSFL, PLGC(Me)AG, SSKLQ, GPLGIAGQ, Glu-Pro-Cit-Gly-Hof-Tyr-Leu, PVGLIG, D-Ala-Phe-Lys, or a combination thereof. In some embodiments, X and/or Y is a p-amido-benzyl ether. In some embodiments, X is 6-aminohexanoyl, 5-amino-3-oxapentanoyl, or a combination thereof. In some embodiments, Y is Val-Cit-(p-amido)benzyloxycarbonyl (Val-Cit-PAB).

In some embodiments, X and/or Y is cleaved by thrombin. In some embodiments, X and/or Y is substantially specific for thrombin, MMPs or elastases. In some embodiments, X and/or Y is cleaved by or is substantially specific for MMPs (PLGLAG and PLGC(met)AG, elastases (RLQLK(acetyl) L, plasmin and/or thrombin. In some embodiments, X and/or Y is DPRSFL, PPRSFL or PLGC(Me)AG. In some embodiments, X and/or Y is 6-aminohexanoyl, 5-amino-3-oxapentanoyl, or a combination thereof. In some embodiments, X and/or Y is a p-amido-benzyl ether, such as for example Val-Cit-(p-amido)benzyloxycarbonyl (Val-Cit-PAB). In some embodiments, X is DPRSFL, PPRSFL or PLGC(Me) AG. In some embodiments, X is 6-aminohexanoyl, 5-amino-3-oxapentanoyl, or a combination thereof. In some embodiments, Y is Val-Cit-(p-amido)benzyloxycarbonyl (Val-Cit-PAB). In some embodiments, the MMP 2,9 cleavable or substantially specific sequence is PLGLAG and/or PLGC(met)AG. In some embodiments, the MMP cleavable or substantially specific sequences could include but are not limited to RS-(Cit)-G-(homoF)-YLY, PLGLEEA, CRPAHLRDSG, SLAYYTA, NISDLTAG, PPSSLRVT, SGESLSNLTA, RIGFLR elastase cleavable or substantially specific sequence is RLQLK(acetyl)L. In some embodiments, the plasmin cleavable or substantially specific sequence is RLQLKL. Thrombin selective substrates DPRSFL, PPRSFL, Norleucine-TPRSFL. In some embodiments, the chymase cleavable or substantially specific sequence GVAYISGA. Urokinase-type plasminogen activator (uPA) and tissue plasminogen activator (tPA) cleavable or substantially specific sequence is YGRAAA. In some embodiments, the uPA cleavable or substantially specific sequence is YGPRNR. In some embodiments, X and Y are different cleavable linkers such that specific properties of the linkers are employed for delivery of cargo and therapeutic compounds to particular cells and/or cellular environments. In some embodiments, linker X and/or Y can be any combination of linkers described herein.

In some embodiments, X and/or Y is cleaved by a peroxide, including but not limited to hydrogen peroxide. Examples of X linkers cleaved by hydrogen peroxide include but are not limited to ACPP1 and/or ACPP2. The representative structure for ACPP 1 is:

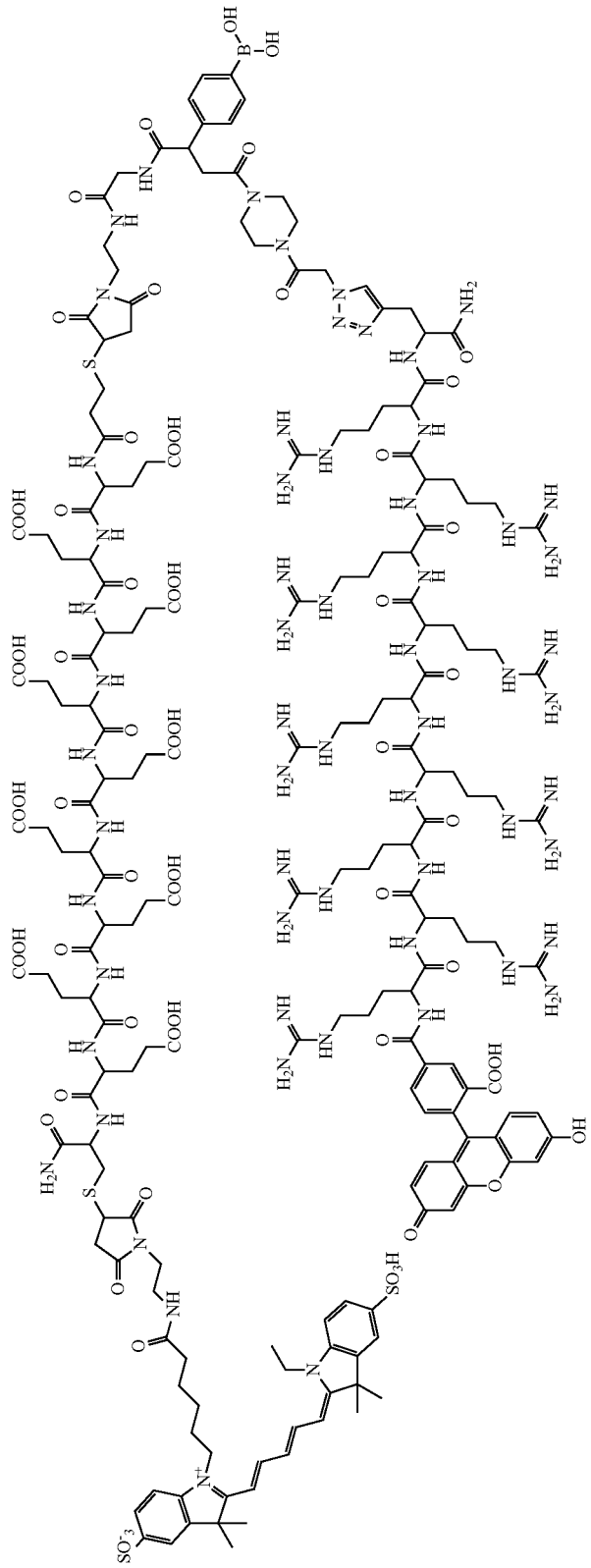

The representative structure for ACPP2 is:

ACPP2
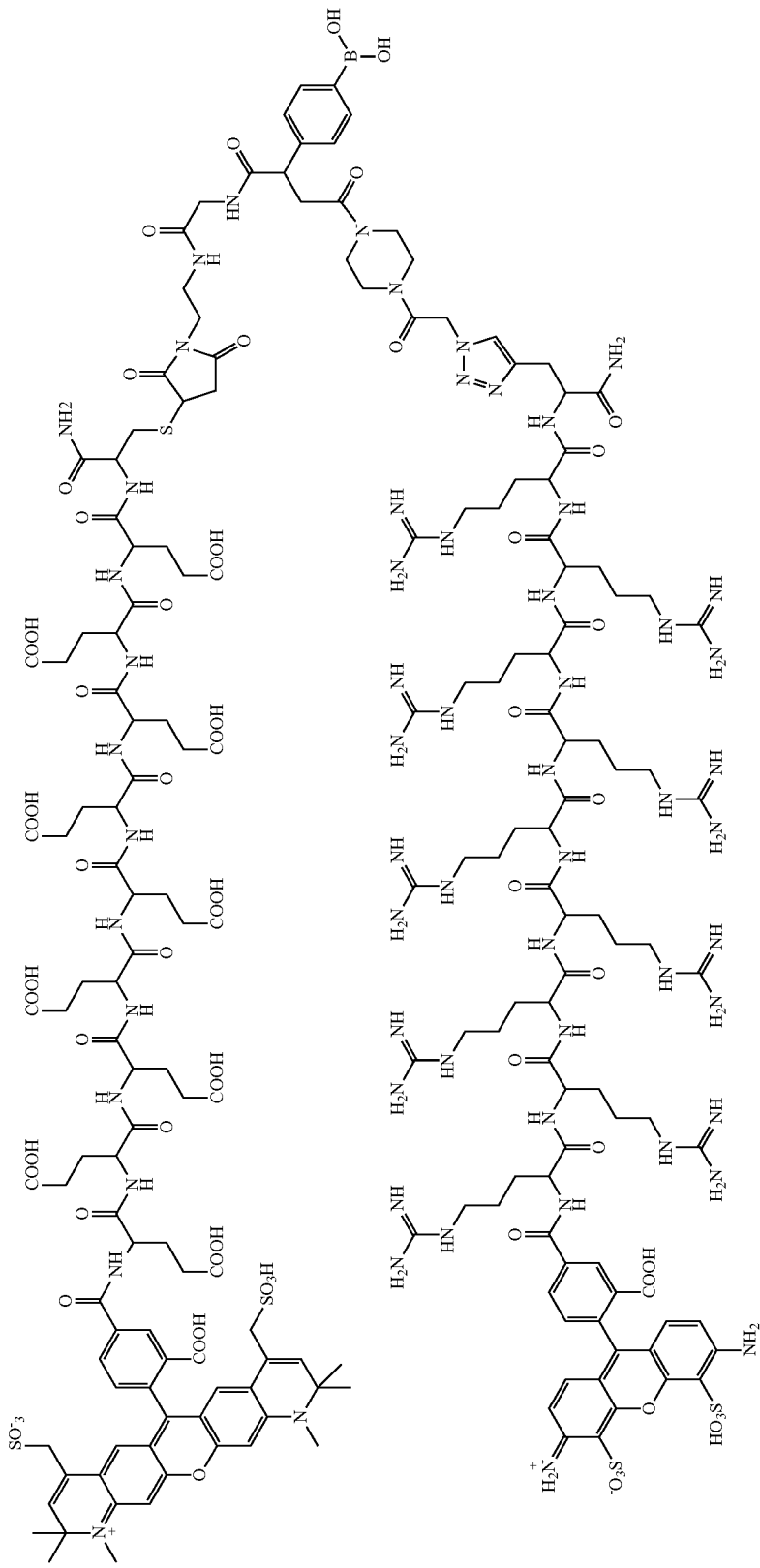

Other related structures cleavable by hydrogen peroxide are also contemplated by the present invention.

In some embodiments, a linker consisting of one or more amino acids is used to join peptide sequence A (i.e., the sequence designed to prevent uptake into cells) and peptide sequence B (i.e., the TS). Generally the peptide linker will have no specific biological activity other than to join the molecules or to preserve some minimum distance or other spatial relationship between them. However, the constituent amino acids of the linker may be selected to influence some property of the molecule such as the folding, net charge, or hydrophobicity.

In some embodiments, the linker is flexible. In some embodiments, the linker is rigid. In some embodiments, both linkers are flexible. In some embodiments, both linkers are rigid. In some embodiments, one linker is rigid and one linker is flexible.

In some embodiments, one or both linkers comprise a linear structure. In some embodiments, one or both linkers comprise a non-linear structure. In some embodiments, one or both linkers comprise a branched structure. In some embodiments, one or both linkers comprise a cyclic structure. In some embodiments, the linkers comprise the same structure. In some embodiments, the linkers comprise different structures.

In some embodiments, X and/or Y is about 5 to about 30 atoms in length. In some embodiments, X and/or Y is about 6 atoms in length. In some embodiments, X and/or Y is about 8 atoms in length. In some embodiments, X and/or Y is about 10 atoms in length. In some embodiments, X and/or Y is about 12 atoms in length. In some embodiments, X and/or Y is about 14 atoms in length. In some embodiments, X and/or Y is about 16 atoms in length. In some embodiments, X and/or Y is about 18 atoms in length. In some embodiments, X and/or Y is about 20 atoms in length. In some embodiments, X and/or Y is about 25 atoms in length. In some embodiments, X and/or Y is about 30 atoms in length.

In some embodiments, X and/or Y is cleaved by thrombin. In some embodiments, the linker is substantially specific for thrombin.

In some embodiments, the linker X and/or Y has a formula selected from: DPRSFL, or PPRSFL. In some embodiments, linker has a formula selected from: DPRSFL, or PPRSFL.

In some embodiments, the linker X and/or Y binds peptide portion A (i.e., the peptide sequence which prevents cellular uptake) to peptide portion B (i.e., the MTS sequence) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, X and/or Y comprises a peptide linkage. The peptide linkage comprises L-amino acids and/or D-amino acids. In embodiments of the invention, D-amino acids are employed in order to minimize immunogenicity and nonspecific cleavage by background peptidases or proteases. Cellular uptake of oligo-D-arginine sequences is known to be as good as or better than that of oligo-L-arginines.

It will be understood that a linker disclosed herein may include non-standard amino acids, such as, for example, hydroxylysine, desmosine, isodesmosine, or other non-standard amino acids. A linker disclosed herein may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A linker disclosed herein may also include peptide mimetic moieties, including portions linked by non-peptide bonds and amino acids linked by or to non-amino acid portions.

In some embodiments, a MTS molecule disclosed herein comprises a single type of linker. Use of a single mechanism to mediate uptake of both imaging and therapeutic cargoes is particularly valuable, because imaging with noninjurous tracer quantities can be used to test whether a subsequent therapeutic dose is likely to concentrate correctly in the target tissue.

In some embodiments, a MTS molecule disclosed herein comprises different types of linkers. Use of multiple mechanisms to mediate uptake of both imaging and therapeutic cargoes is particularly valuable, because imaging with noninjurous tracer quantities can be used to test whether a subsequent therapeutic dose is likely to concentrate correctly in the target tissue.

In some embodiments, a MTS molecule disclosed herein comprises a plurality of linkers. Where a MTS molecule disclosed herein includes multiple linkages X and/or Y, separation of portion A from the other portions of the molecule requires cleavage of all linkages X and/or Y. Cleavage of multiple linkers X and/or Y may be simultaneous or sequential Multiple linkages X and/or Y may include linkages X having different specificities, linkages Y have different specificities and/or linkages X and/or Y having different specificities so that separation of portion A from the other portions of the molecule requires that more than one condition or environment ("extracellular signals") be encountered by the molecule. Cleavage of multiple linkers X and/or Y thus serves as a detector of combinations of such extracellular signals. For example, a MTS molecule may include two linker portions Xa and Xb connecting basic portion B with acidic portion A. Both linkers Xa and Xb must be cleaved before acidic portion A is separated from basic portion B allowing entry of portion B and cargo moiety C or therapeutic moiety T (if any) to enter a cell. For example, a MTS molecule may include two linker portions Ya and Yb connecting basic portion B with acidic portion A. Both linkers Ya and Yb must be cleaved before acidic portion A is separated from basic portion B allowing entry of portion B and cargo moiety C or therapeutic moiety T (if any) to enter a cell. For example, a MTS molecule may include four linker portions Xa, Xb, Ya and Yb connecting basic portion B with acidic portion A. All four linkers Xa, Xb, Ya and Yb must be cleaved before acidic portion A is separated from basic portion B allowing entry of portion B and cargo moiety C or therapeutic moiety T (if any) to enter a cell. It will be understood that a linker region may link to either a basic portion B or a cargo moiety C or therapeutic moiety T independently of another linker that may be present, and that, where desired, more than two linker regions X may be included.

Combinations of two or more linkers X and/or Y may be used to further modulate the detection of multiple proteases with a single MTS molecule, as well as targeting and delivery of molecules to desired cells, tissue or regions. Combinations of extracellular signals are used to widen or narrow the specificity of the cleavage of linkers X and/or Y if desired. Where multiple linkers X and/or Y are linked in parallel, the specificity of cleavage is narrowed, since each linker X must be cleaved before portion. A may separate from the remainder of the molecule. Where multiple linkers X and/or Y are linked in series, the specificity of cleavage is broadened, since cleavage on any one linker X and/or Y allows separation of portion A from the remainder of the molecule. For example, in order to detect either a protease OR hypoxia (i.e., to cleave X and/or Y in the presence of either protease or hypoxia), a linker X and/or Y is designed to place the protease-sensitive and reduction-sensitive sites in tandem, so that cleavage of either would suffice to allow separation of the acidic portion. Alternatively, in order to detect the presence of both a protease and hypoxia (i.e., to cleave X and/or Y in the presence of both protease and hypoxia but not in the presence of only one alone), a linker X and/or Y is designed to place the protease sensitive site between at least one pair of cysteines that are disulfide-bonded to each other In that case, both protease cleavage and disulfide reduction are required in order to allow separation of portion A.

One important class of signals is the hydrolytic activity of matrix metalloproteinases (MMPs), which are very important in the invasive migration of metastatic tumor cells. MMPs are also believed to play major roles in inflammation and stroke. MMPs are reviewed in Visse et al., *Circ. Res.* 92:827-839 (2003). MMPs may be used to cleave a linker X and/or Y and so to allow separation of acidic portion A from portions B and C, allowing cellular uptake of cargo C and/or therapeutic compound T so that cellular uptake of C and/or T is triggered by action of MMPs. Such uptake is typically in the vicinity of the MMPs that trigger cleavage of X and/or Y. Thus, uptake of molecules having features of the invention are able to direct cellular uptake of cargo C and or therapeutic compound T to specific cells, tissues, or regions having active MMPs in the extracellular environment.

For example, a linker X and/or Y that includes the amino-acid sequence PLGLAG (SEQ ID NO: 1) may be cleaved by the metalloproteinase enzyme MMP-2 (a major MMP in cancer and inflammation). Cleavage of such a linker X and/or Y occurs between the central G and L residues, causing cell uptake to increase by 10 to 20-fold. A great deal is known about the substrate preferences of different MMPs, so that linkers X and/or Y may be designed that are able to bias X and/or Y to be preferentially sensitive to particular subclasses of MMPs, or to individual members of the large MMP family of proteinases. For example, in some embodiments, linkers X and/or Y designed to be cleaved by membrane-anchored MMPs are particularly employed because their activity remains localized to the outer surface of the expressing cell. In alternative embodiments, linkers X and/or Y designed to be cleaved by a soluble secreted MMP are employed where diffusion of cargo C and/or therapeutic compound T away from the exact location of cleavage may be desired, thereby increasing the spatial distribution of the cargo C and/or therapeutic compound T. Other linkers X and/or Y cleavable by other MMPs are discussed throughout the disclosure.

Hypoxia is an important pathological signal. For example, hypoxia is thought to cause cancer cells to become more resistant to radiation and chemotherapy, and also to initiate angiogenesis. A linker X and/or Y suitable for cleavage in or near tissues suffering from hypoxia enables targeting of portion B and C and/or T to cancer cells and cancerous tissues, infarct regions, and other hypoxic regions. For example, a linker X and/or Y that includes a disulfide bond is preferentially cleaved in hypoxic regions and so targets cargo delivery to cells in such a region. In a hypoxic environment in the presence of, for example, leaky or necrotic cells, free thiols and other reducing agents become available extracellularly, while the $O_2$ that normally keeps the extracellular environment oxidizing is by definition depleted. This shift in the redox balance should promote reduction and cleavage of a disulfide bond within a linker X and/or Y. In addition to disulfide linkages which take advantage of thiol-disulfide equilibria, linkages including quinones that fall apart when reduced to hydroquinones may be used in a linker X and/or Y designed to be cleaved in a hypoxic environment.

Necrosis often leads to release of enzymes or other cell contents that may be used to trigger cleavage of a linker X and/or Y. A linker X and/or Y designed for cleavage in regions of necrosis in the absence of hypoxia, for example, may be one that is cleaved by calpains or other proteases that may be released from necrotic cells. Such cleavage of linkers X by calpains would release the connected portions B-C and/or compound T from portion A allowing cargo C and/or therapeutic compound T to be taken up by diseased cells and by neighboring cells that had not yet become fully leaky.

Acidosis is also commonly observed in sites of damaged or hypoxic tissue, due to the Warburg shift from oxidative phosphorylation to anaerobic glycolysis and lactic acid production. Such local acidity could be sensed either by making an acid-labile linker X and/or Y (e.g., by including in X and/or Y an acetal or vinyl ether linkage). Alternatively, or in addition, acidosis may be used as a trigger of cargo C and/or therapeutic compound T uptake by replacing some of the arginines within B by histidines, which only become cationic below pH 7.

Molecules having features of the invention are suitable for carrying different cargoes C and/or compounds T, including different types of cargoes C and/or compounds T and different species of the same types of cargo C and/or compound T, for uptake into cells. For example, different types of cargo include marker cargoes (e.g., fluorescent or radioactive label moieties) and different types of compounds T include therapeutic cargoes (e.g., chemotherapeutic molecules such as methotrexate or doxorubicin), or other cargoes C and/or compounds T. Where destruction of aberrant or diseased cells is therapeutically required, a cargo C and/or a compound T include a therapeutic cargo such as a "cytotoxic agent," i.e. a substance that inhibits or prevents the function of cells and/or causes destruction of cells. In some embodiments, a single molecule having features of the invention includes more than one cargo portion C and/or compound T so that a basic portion B may be linked to multiple cargoes C and/or compounds T. Such multiple cargoes C and/or compounds T include marker cargoes, therapeutic cargoes, or other cargoes. Multiple cargoes C and compounds T may allow, for example, delivery of both a radioactive marker and an ultrasound or contrast agent, allowing imaging by different modalities. Alternatively, for example, delivery of a radioactive cargo C along with an anti-cancer agent compound T, providing enhanced anticancer activity, or delivery of a radioactive cargo with a fluorescent cargo, allowing multiple means of localizing and identifying cells which have taken up cargo C and/or compound T.

Delivery of cargo C and/or compound T such as a fluorescent molecule may be used to visualize cells having a certain condition or cells in a region exhibiting a particular condition. For example, thrombosis (clot formation) may be visualized by designing a linker X and/or Y to be cleaved by any of the many proteases in the blood clot formation cascade for delivery of a cargo including a fluorescent or other marker to the region. Similarly, complement activation may be visualized by designing a linker X and/or Y to be cleaved by any one or more of the proteases in the complement activation cascades for delivery of a fluorescent or other marker to the region. Thus, fluorescent molecules are one example of a marker that may be delivered to target cells and regions upon release of a portion A upon cleavage of a linker X and/or Y.

Delivery of compound T such as a therapeutic compound may be used to treat cells having a certain condition or cells in a region exhibiting a particular condition. For example, neoplasia cells may be targeted by designing a linker X and/or Y to be cleaved by any of the many proteases produced by tumor cells, including for example MMPs. Thus, therapeutic compounds for the treatment of neoplasia are one example of compounds that may be delivered to target cells and regions upon release of a portion A and/or B upon cleavage of a linker X and/or Y.

A molecule having features of the invention may include one or more linkers X and/or Y so that an acidic portion A may be linked to portions B and C by one or more linkages. Such linkages connecting to portion A may be to portion B, to portion C, or to both portions B and C. Where a molecule having features of the invention includes multiple linkages X and/or Y, separation of portion A from the other portions of the molecule requires cleavage of all linkages X and/or Y. Cleavage of multiple linkers X and/or Y may be simultaneous or sequential. Multiple linkages X and/or Y may include linkages X and/or Y having different specificities, so that separation of portion A from the other portions of the molecule requires that more than one condition or environment ("extracellular signals") be encountered by the molecule. Cleavage of multiple linkers X and/or Y thus serves as a detector of combinations of such extracellular signals. In some embodiments, MTS molecule having includes two linker portions Xa and Xb connecting basic portion B with acidic portion A. In some embodiments, a cyclic MTS molecule includes two linker regions Xa and Xb connecting basic portion B with acidic portion A. In some embodiments, both linkers Xa and Xb must be cleaved before acidic portion A is separated from basic portion B allowing entry of portion B and cargo portion C (if any) to enter a cell. In some embodiments, MTS molecule having includes two linker portions Ya and Yb connecting basic portion B with acidic portion A. In some embodiments, a cyclic MTS molecule includes two linker regions Ya and Yb connecting basic portion B with acidic portion A. In some embodiments, both linkers Ya and Yb must be cleaved before acidic portion A is separated from basic portion B allowing entry of portion B and cargo portion C (if any) to enter a cell. In some embodiments, MTS molecule having includes two linker portions X and Y connecting basic portion B with acidic portion A. In some embodiments, a cyclic MTS molecule includes two linker regions X and Y connecting basic portion B with acidic portion A. In some embodiments, both linkers X and Y must be cleaved before acidic portion A is separated from basic portion B allowing entry of portion B and cargo portion C (if any) to enter a cell. In some embodiments, MTS molecule having includes four linker portions Xa, Xb, Ya and Yb connecting basic portion B with acidic portion A. In some embodiments, a cyclic MTS molecule includes four linker regions Xa, Xb, Ya and Yb connecting basic portion B with acidic portion A. In some embodiments, linkers Xa, Xb, Ya and Yb must be cleaved before acidic portion A is separated from basic portion B allowing entry of portion B and cargo portion C (if any) to enter a cell. In some embodiments, MTS molecule having includes more than two portions X and X connecting basic portion B with acidic portion A. In some embodiments, a cyclic MTS molecule includes two linker regions X and Y connecting basic portion B with acidic portion A. In some embodiments, both linkers X and Y must be cleaved before acidic portion A is separated from basic portion B allowing entry of portion B and cargo portion C (if any) to enter a cell. It will be understood that a linker region may link to either a basic portion B or a cargo portion C and/or compound T independently of another linker that may be present, and that, where desired, more than two linker regions X and/or Y may be included.

Combinations of two or more linkers X and/or Y may be used to further modulate the targeting and delivery of molecules to desired cells, tissue or regions. Boolean combinations of extracellular signals can be detected to widen or narrow the specificity of the cleavage of linkers X and/or Y if desired. Where multiple linkers X and/or Y are linked in parallel, the specificity of cleavage is narrowed, since each linker X and/or Y must be cleaved before portion A may separate from the remainder of the molecule. Where multiple linkers X and/or Y are linked in series, the specificity of cleavage is broadened, since cleavage on any one linker X allows separation of portion A from the remainder of the molecule. For example, in order to detect either a protease OR hypoxia (i.e., to cleave X and/or Y in the presence of either protease or hypoxia), a linker X and/or Y is designed to place the protease-sensitive and reduction-sensitive sites in tandem, so that cleavage of either would suffice to allow separation of the acidic portion A. Alternatively, in order to detect the presence of both a protease AND hypoxia (i.e., to cleave X and/or Y in the presence of both protease and hypoxia but not in the presence of only one alone), a linker X and/or Y is designed to place the protease sensitive site between at least one pair of cysteines that are disulfide-bonded to each other. In that case, both protease cleavage and disulfide reduction are required in order to allow separation of portion A.

D amino acids may be used in MTS molecules having features of the invention. For example, some or all of the peptides of portions A and B may be D-amino acids in some embodiments of the invention. In an embodiment of the invention suitable for delivering a detectable marker to a target cell, a MTS having features of the invention includes a contrast agent as cargo C and/or compound T attached to a basic portion B comprising 8 to 10 D-arginines. Acidic portion A may include D-amino acids as well. Similarly, a drug may be delivered to a cell by such molecules having a basic portion B including 8 to 10 D-arginines and an acidic portion A including acidic D-amino acids.

It will be understood that a MTS molecule having features of the invention may include non-standard amino acids, such as, for example, hydroxylysine, desmosine, isodesmosine, or other non-standard amino acids. A MTS molecule having features of the invention may include modified amino acids, including post-translationally modified amino acids such as, for example, methylated amino acids (e.g., methyl histidine, methylated forms of lysine, etc.), acetylated amino acids, amidated amino acids, formylated amino acids, hydroxylated amino acids, phosphorylated amino acids, or other modified amino acids. A MTS molecule having features of the invention may also include peptide mimetic moieties, including portions linked by non-peptide bonds and amino acids linked by or to non-amino acid portions. For example, a MTS molecule having features of the invention may include peptoids, carbamates, vinyl polymers, or other molecules having non-peptide linkages but having an acidic portion cleavably linked to a basic portion having a cargo moiety.

The linker portion X and/or Y may be designed so that it is cleaved, for example, by proteolytic enzymes or reducing environment, as may be found near cancerous cells, or a hydrogen peroxide environment found near inflammatory diseases, neurodegenerative diseases, cardiovascular diseases, diabetes and cancer (neoplasia). Such an environment, or such enzymes or hydrogen peroxide, are typically not found near normal cells. In some embodiments, a cleavable linker X and/or Y is designed to be cleaved near diseased cells, including cancerous cells. In some embodiments, the cleavable linker is not cleaved near normal tissue. A capable of vetoing cellular uptake of a portion B, and of a portion B-C, and/or B-T blocking the entry of cargo and/or compound T into normal tissue.

In some embodiments, the linker portion X and/or Y may be cleaved, for example, by proteolytic enzymes, reducing environment or reactive oxygen species containing found near diseased cells, such as inflammatory diseased cells, neurodegenerative diseased cells, cardiovascular diseased cells, diabetic cells and cancerous cells to deliver a marker or a drug to cancerous cells. In some embodiments, a MTS molecule with a cleavable linker X and/or Y that is cleaved by proteolytic enzymes, by the reducing environment or by the reactive oxygen species containing environment near diseased cells is able to facilitate cargo entry into diseased tissue. Thus, the selective cleavage of the linker X and/or Y and the resulting separation of cargo C and/or compound T and basic portion B from acidic portion A allows the targeted uptake of cargo C and/or compound T into cells having selected features (e.g., enzymes), or located near to, a particular environment. Thus, molecules having features of the invention are able to selectively deliver cargo to target cells without doing so to normal or otherwise non-targeted cells.

In embodiments, a MTS molecule disclosed herein is a linear molecule. In embodiments, a MTS molecule disclosed herein is a cyclic molecule, as schematically illustrated in FIG. 1B of WO 2011/008996; incorporated herein by reference in its entirety. In embodiments, a MTS molecule disclosed herein comprises a cyclic portion and a linear portion.

A MTS disclosed herein may be of any length. In some embodiments, a MTS molecule disclosed herein is about 7 to about 40 amino acids in length, not including the length of a linker X and/or Y, a cargo moiety C and/or a compound T. In other embodiments, particularly where multiple non-acidic (in portion A) or non-basic (in portion B) amino acids are included in one or both of portions A and B, portions A and B of a MTS molecule disclosed herein may together be about 50, or about 60, or about 70 amino acids in length. A cyclic portion of a MTS molecule disclosed herein may include about 12 to about 60 amino acids, not including the length of a linker X and/or Y, a cargo moiety C, and/or a compound T. For example, a linear MTS molecule disclosed herein may have a basic portion B having between about 5 to about 20 basic amino acids (between about 9 to about 16 basic amino acids) and an acidic portion A having between about 2 to about 20 acidic amino acids (e.g., between about 5 to about 20, between about 5 to about 9 acidic amino acids). In some particular embodiments, a MTS molecule disclosed herein may have a basic portion B having between about 9 to about 16 basic amino acids and between about 5 to about 9 acidic amino acids. In some embodiments, A is consecutive glutamates (i.e., EEEEEEEE, E9, eeeeeeee, or e9), B is nine consecutive arginines (i.e., RRRRRRRRR, R9, rrrrrrrrr, or r9).

In some embodiments, the MTS is selected from: Suc-e9-XDPRSFL-r9-c(Cy5)-CONH2; Suc-e9-ODPRSFL-r9-c(Cy5)-CONH2; Suc-e9-Xdprsfl-r9-c(Cy5)-CONH2; cRGD-ACPP-MMAE; and (D-arg)9-Cy5 CPP-c(RGDfK)-(D-glu)9.

A MTS molecule disclosed herein may be of any length. In some embodiments, a MTS molecule disclosed herein is about 7 to about 40 amino acids in length, not including the length of a linker X and/or Y, a cargo moiety C and/or compound T. In other embodiments, particularly where multiple non-acidic (in portion A) or non-basic (in portion B) amino acids are included in one or both of portions A and B, portions A and B of a MTS molecule disclosed herein may together be about 50, or about 60, or about 70 amino acids in length. A cyclic portion of a MTS molecule disclosed herein may include about 12 to about 60 amino acids, not including the length of a linker X and/or Y, a cargo moiety and/or compound T.

For example, a linear MTS molecule disclosed herein may have a basic portion B having between about 5 to about 20 basic amino acids (in some embodiments between about 9 to about 16 basic amino acids) and an acidic portion A having between about 2 to about 20 acidic amino acids (e.g., between about 5 to about 20, between about 5 to about 9 acidic amino acids). In some embodiments, a MTS molecule disclosed herein may have a basic portion B having between about 9 to about 16 basic amino acids and between about 5 to about 9 acidic amino acids. In some embodiments, A is 9 consecutive glutamates (i.e., EEEEEEEE, E9, eeeeeeee, or e9), B is nine consecutive arginines (i.e., RRRRRRRRR, R9, rrrrrrrrr, or r9), and X and/or Y is PLGLAG. In some embodiments, A is 9 consecutive glutamates (i.e., EEEEEEEE, E9, eeeeeeee, or e9), B is nine consecutive arginines (i.e., RRRRRRRRR, R9, rrrrrrrrr, or r9), and X and/or Y is DPRSFL, PPRSFL, PLGC(Me)AG, 6-aminohexanoyl, 5-amino-3-oxapentanoyl, Val-Cit-(p-amido)benzyloxycarbonyl (Val-Cit-PAB) or a combination thereof. In some embodiments, A is 9 consecutive glutamates (i.e., EEEEEEEE, E9, eeeeeeee, or e9), B is nine consecutive arginines (i.e., RRRRRRRRR, R9, rrrrrrrrr, or r9), and X is PLGLAG, DPRSFL, PPRSFL, PLGC(Me)AG, or a combination thereof. In some embodiments, A is 9 consecutive glutamates (i.e., EEEEEEEE, E9, eeeeeeee, or e9), B is nine consecutive arginines (i.e., RRRRRRRRR, R9, rrrrrrrrr, or r9), and X is 6-aminohexanoyl, 5-amino-3-oxapentanoyl, or a combination thereof. In some embodiments, A is 9 consecutive glutamates (i.e., EEEEEEEE, E9, eeeeeeee, or e9), B is nine consecutive arginines (i.e., RRRRRRRRR, R9, rrrrrrrrr, or r9), and Y is Val-Cit-(p-amido)benzyloxycarbonyl (Val-Cit-PAB).

In some embodiments, the MTS molecule has a formula given below. It should be noted that in some instances the peptide sequence is given by the amino acid symbol and a number indicating the number of amino acids (for example, R9 translates to RRRRRRRRR or nine consecutive L-arginines; and r9 translates to nine consecutive D-arginines or rrrrrrrrr and E9 translates to EEEEEEEEE or nine consecutive L-glutamates; and e9 translates to nine consecutive D-glutamates or eeeeeeee):

cRGD-MMP-MMAE (Ligand=Cyclic(RGDfC); Substrate=o-PLGC(Me)AG-o; o=5-amino-3-oxopentanoyl)

cRAD-PEG6-MMAE (Ligand=Cyclic(RADfC); Substrate=PEG6-o; o=5-amino-3-oxopentanoyl)

cRGD-PEG6-MMAE (Ligand=Cyclic(RGDfC); Substrate=PEG6-o; o=5-amino-3-oxopentanoyl)

cRAD-MMP-MMAE (Ligand=Cyclic(RADfC); Substrate=o-PLGC(Me)AG-o; o=5-amino-3-oxopentanoyl)

Suc-eeeeeeeee-XDPRSFL-rrrrrrrrr-c(Cy5)-CONH2
Suc-eeeeeeeee-ODPRSFL-rrrrrrrrr-c(Cy5)-CONH2
Suc-eeeeeeeee-Xdprsfl-rrrrrrrrr-c(Cy5)-CONH2
cRGD-ACPP-MMAE
(rrrrrrrrr)-Cy5 CPP-c(RGDfK)-(eeeeeeeee)
EDDDDKA-aca-R9-aca-C(Fl)-CONH2
Fl-aca-CRRRRRRRRR-aca-EEEEEEEEEC-CONH2
Fl-aca-CEEEE-aca-RRRRRRRRRC-CONH2
H2N-EEEEEDDDDKA-aca-RRRRRRRRR-aca-C(Fl)-CONH2
H2N-EDDDDKA-aca-RRRRRRRRR-aca-C(Fl)-CONH2
H2N-EEEEEDDDDK ARRRRRRRRR-aca-C(Fl)-CONH2
H2N-EEDDDDKA-aca-rrrrrrrrr-aca-C(Fl)-CONH2
H2N-DDDDDDCA-aca-C(Fl)-CONH2
H2N-EEDDDDKAR-aca-RR-aca-RR-aca-RR-aca-C(Fl)-CONH2
H2N-eeeeee-aca-PLGLAG-rrrrrrrrr-aca-c(Fl)-CONH2
EDA-aca-R,-aca-C(Fl)-CONH2
EDDDDKA-aca-R6-aca-C(DOX)-CONH2
EEEDDDEEEDA-aca-R9-aca-Y(12SI)-CONH2
ededdAAeeeDDDDKA-aca-R,-aca-C(Fl)-CONH2
eddededDDDDKA-aca-Rs-AGA-R6-aca-C(DOX)-CONH2
Ggedgddeeeeeeddeed-aca-PLGLAG-aca-R8-AAA-Ri2-aca-C(Fl)-CONH2
eeddeeddKA-aca-R7-aca-C(Fl)-CONH2
eDDDDKA-aca-RGRGRRR-aca-C(Fl)-CONH2
eddddeeeeeee-aca-PLGLAGKA-aca-R10-aca-C(Fl)-CONH2
eeeeeeeeeeeeeee-aca-DDDDKA-aca-R20-aca-C(Fl)-CONH2
eeeeeeeeedddddd-aca-DDDDK A-aca-R, 7-aca-Y(' 2<iI)-CONH2
dddddddddddddddd-aca-PLGLAG-aca-R,4-aca-C(DOX)-CONH2
NH2-eeeeee-ahx-PLG
LAG-rrrrrrrrr-ahx-c(Fl)-CONH2, where "ahx" indicates aminohexanoic acid
EEEEEDDDDTCAXRRRRRRRRRRXC(Fl)
EEEEEDDDD CRRRRRC(Fl)
EDDDDTCXRRRRRC(Fl)
EEDDDDKAXRRRRXRC(Fl)
DDDDDD CRRRRRC(Fl)
EEDDDDKAXrrrrrrrrrXC(Fl)
eeeeeeXPLGLAGrrrrrrrrrXc(Fl)
UeeeeeeeeXPLGLAGrrrrrrrrrrXk(Fl)
eeeeeeeXPLGLAGrrrrrrrrrXc(Cy5)
UeeeeeeXPLGLAGrrrrrrrrrXc(Cy5)
UeeeeeeeeXPLGLAGlrrrrrrrrXk(Cy5)
11-kDa PEG]XeeeeeeeeeeXPLGLAGrrrrrrrrrXk(Cy5)
11-kDa PEG]XeeeeeeeeeeXLALGPGrrrrrrrrrXk(Cy5)
Fl-XrrrrrrrrrXPLGLAGeeeeeeeee-3Ala
Fl-XrrrrrrrrrXSGRSAeeeeeeeee-3Ala
eeeeeeXSGRSAXrrrrrrrrrXc(Cy5)
Fl-rrrrrrrrrc-SS-ceeeeeee
succinyl-e8-XPLGLAG-r9-Xk, where X denotes 6-aminohexanoyl
[11 kDa PEG]-X-e9-XPLGLAG-r9
[11-kDa PEG]-X-e9-XPLGLAG-r9-Xk(Cy5)
H2N-e6-XPLGLAG-r9-Xc(Cy5)-CONH2, where X=aminohexanoic acid
H2N-eeeeee-(ahx)-PLG LAG-rrrrrrrrr-(ahx)-c(Fluor)-CONH2
XeeeeeeeeeXPLGLAGrrrrrrrrrXk
eeeeeeeeeXLALGPG-rrrrrrrrrXk(Cy5)
mPEG(11 kd)-S—CH2-CONH-ahx-e9-ahx-PLGLAG-r9-ahx-k-CONH2 mPEG-S—CH2CONH-e9-ahx-PLGLAG-r9-K[DOTA(Gd)]-CONH2
(11 KDa-mPEG)-e9-XPLGLAG-r9-[DPK-99mTc(CO)3]
(70 KDa-dextran)-e9-XPLGLAG-r9-[DPK-99mTc(CO)3]
murine serum albumin)-e9-XPLGLAG-r9-[DPK-99mTc(CO)3],
(PAMAM generation 5 dendrimer)-e9-XPLGLAX-r9-[DPK-"mTc(CO)3]
(70 KDa dextran)-e9-XPLGLAX-r9-(DOTA-'11In)
(11-KDa-mPEG)-e9-XPLGLAG-r9-K(DOTA-Gd)
Suc9-(70 KDa dextran)-e9-XPLGLAG-r9-K(DOT A-Gd)
Suc9-(70 KDa dextran)-e9-XPLGLAX-r9-K(DOT A-Gd)
Suc9-(70 KDa dextran)-e9-XPLGLAG-r9-K(DOT A-Gd)
cyclic[succinoyl-PLGLAG-c(11 KDa-mPEG)-e9-XPLGLAG-r9-K]-k(Cy5)
Cy5-X-e6-XPLGLAG-r9-Xk(Cy5)
Cy7-X-e6-XPLGLAG-r9-Xk(Cy5)
11 KDa mPEG-e9-PLGLAG-r9
Ac-r9-k-NH2
mPEG(11 kd)-e9-XPLGLAG-r9-Xk-NH2
e9-XPLGLAG-r9-Xk-NH2

TABLE 1

| Cap | Macromolecule | Polyanion | P4 | P3 | P2 | P1 | P1' | P2' | P3'...Pn' | Polycation | Cargo | C-term |
|---|---|---|---|---|---|---|---|---|---|---|---|---|
| Suc9 | Dextran (70 KDa) | e9 | X | P | L | G | L | A | G | r9 | K[DOTA(Gd)] | NH2 |
| Suc | — | e9 | X | P | L | G | C(Me) | A | X | r9 | DPK | NH2 |
| Suc | — | e9 | X | P | ThienylAla | G | C(Me) | A | X | r9 | DPK | NH2 |
| Suc | — | e9 | X | P | F(4-Cl) | G | C(Me) | A | X | r9 | DPK | NH2 |
| Suc | — | e8 | X | P | L | G | L | A | G | r9 | c[Cy5] | NH2 |
| Suc | — | e8 | X | P | F(4-Cl) | G | C(Me) | M | X | r9 | c[Cy5] | NH2 |
| Suc | — | e8 | X | P | F(4-Cl) | G | C(Me) | Y | X | r9 | c[Cy5] | NH2 |
| Suc | — | e8 | X | P | F(4-Cl) | G | C(Me) | R | X | r9 | c[Cy5] | NH2 |
| Suc | — | e8 | X | P | F(4-Cl) | G | C(Me) | PhGly | X | r9 | c[Cy5] | NH2 |
| Suc | — | e8 | X | P | F(4-Cl) | G | C(Me) | C(Me) | X | r9 | c[Cy5] | NH2 |
| — | Albumin | e9 | X | P | L | G | L | A | X | r9 | DPK | NH2 |
| Suc | — | e8 | X | P | C(Me) | G | C(Me) | A | X | r9 | c[Cy5] | NH2 |
| Suc | — | e8 | X | P | ThienylAla | G | C(Me) | A | X | r9 | c[Cy5] | NH2 |
| Suc | — | e8 | X | P | F(4-Cl) | G | C(Me) | A | X | r9 | c[Cy5] | NH2 |
| Suc | — | e8 | X | P | K(Dnp) | G | C(Me) | A | X | r9 | c[Cy5] | NH2 |
| — | Albumin | e9 | X | P | L | G | L | A | X | r9 | DPK | NH2 |
| Suc | — | e8 | X | P | L | G | C(Me) | M | X | r9 | c[Cy5] | NH2 |
| Suc | — | e8 | X | P | L | G | C(Me) | Y | X | r9 | c[Cy5] | NH2 |
| Suc127 | PAMAM-Gen5 | e9 | X | P | L | G | L | A | X | r9 | DPK | NH2 |

TABLE 1-continued

| Cap | Macromolecule | Polyanion | P4 | P3 | P2 | P1 | P1' | P2' | P3'...Pn' | Polycation | Cargo | C-term |
|---|---|---|---|---|---|---|---|---|---|---|---|---|
| Suc | — | e8 | X | P | L | G | C(Me) | A | X | r9 | c[Cy5] | NH$_2$ |
| Suc9 | Dextran (70 KDa) | e9 | X | P | L | G | L | A | G | r9 | K[DOTA(Gd)] | NH$_2$ |
| Suc127 | PAMAM-Gen5 | e9 | X | P | L | G | L | A | X | r9 | k[Cy5] | NH$_2$ |
| — | — | — | — | — | — | — | — | — | — | r9 | Xe[Cy5] | NH$_2$ |
| Ac127 | PAMAM-Gen5 | e9 | X | P | L | G | L | A | X | r9 | k[Cy5] | NH$_2$ |
| Suc | — | e8 | X | P | L | G | L | F(4-NO2) | A | Xr9 | k[Cy5] | NH$_2$ |
| Suc127 | PAMAM-Gen5 | e9 | X | P | L | G | L | A | X | r9 | k[Cy5] | NH$_2$ |
| Suc63 | PAMAM-Gen4 | e9 | X | P | L | G | L | A | X | r9 | k[Cy5] | NH$_2$ |
| — | Albumin | e9 | X | P | L | G | L | A | G | r9 | DPK | NH$_2$ |
| Suc136 | Dextran (86 KDa) | e9 | X | P | L | G | L | A | X | r9 | k[Cy5] | NH$_2$ |
| Suc | — | e8 | X | P | L | G | L | A | X | r9 | k[Cy5] | NH$_2$ |
| Suc9 | Dextran (70 KDa) | e9 | X | P | L | G | L | A | X | r9 | K[DOTA(Gd)] | NH$_2$ |
| Suc9 | Dextran (70 KDa) | e9 | X | P | L | G | L | A | X | r9 | K[DOTA(Gd)] | NH$_2$ |
| Suc9 | Dextran (70 KDa) | e9 | X | P | L | G | L | A | G | r9 | k[Cy5] | NH$_2$ |
| Suc9 | Dextran (70 KDa) | e9 | X | P | L | G | L | A | G | r9 | DPK | NH$_2$ |
| Suc | — | e8 | X | p | l | g | l | a | g | r9 | k[Cy5] | NH$_2$ |
| — | Albumin | e9 | X | p | l | g | l | a | g | r9 | k[Cy5] | NH$_2$ |
| Suc9 | Dextran | e9 | X | p | l | g | l | a | g | r9 | k[Cy5] | NH$_2$ |
| Suc97 | Dextran (500 KDa) | e9 | X | P | L | G | L | A | G | r9 | k[Cy5] | NH$_2$ |
| — | Albumin | e9 | X | P | L | G | L | A | G | r9 | k[Cy5] | NH$_2$ |
| Suc9 | Dextran (70 KDa) | e9 | X | P | L | G | L | A | G | r9 | k[Cy5] | NH$_2$ |
| — | Albumin | e9 | X | P | L | G | L | A | G | r9 | k[Cy5] | NH$_2$ |
| Suc | — | e8 | X | P | L | G | L | A | X | r9 | k[Cy5] | NH$_2$ |
| Suc9 | Dextran (70 KDa) | e9 | X | P | L | G | L | A | G | r9 | k[Cy5] | NH$_2$ |
| — | Albumin | e9 | X | P | L | G | L | A | G | r9 | k[Cy5] | NH$_2$ |
| — | Albumin | e9 | X | P | L | G | L | A | G | r9 | k[Cy5] | NH$_2$ |
| — | Albumin | e9 | X | P | L | G | L | A | G | r9 | k[Cy5] | NH$_2$ |
| Suc9 | Dextran (70 KDa) | e9 | X | P | L | G | L | A | G | r9 | k[Cy5] | NH$_2$ |
| Suc | nonconj. Albumin | e8 | X | P | L | G | L | A | G | r9X | k[Cy5] | NH$_2$ |
| Suc | — | e8 | X | P | L | G | L | A | G | r9X | k[Cy5] | NH$_2$ |
| — | Albumin | e9 | X | P | L | G | L | A | G | r9 | k[Cy5] | NH$_2$ |
| — | mPEG (5 KDa) | e9 | x | p | l | g | l | a | g | r9X | k[Cy5] | NH$_2$ |
| — | mPEG (11 KDa) | e9 | X | P | L | G | L | A | G | r9 | K[DOTA(Gd)] | NH$_2$ |
| — | mPEG (11 KDa) | e10 | X | P | L | G | F(4-NO$_2$) | A | Q | Xr9 | k[Cy5] | NH$_2$ |
| — | mPEG (11 KDa) | e10 | X | P | L | G | C(Me) | W | A | Qr9 | k[Cy5] | NH$_2$ |
| — | mPEG (11 KDa) | e9 | X | P | L | G | C(Me) | W | A | Qr9 | k[Cy5] | NH$_2$ |

In some embodiments, cargo C and/or compound T may be a fluorescent molecule such as fluorescein. Fluorescent cargo moieties enable easy measurement by fluorescence microscopy or flow cytometry in unfixed cultured cells. However, oligoarginine sequences, such as make up portion B, have been demonstrated to import a very wide varieties of cargoes C and/or compounds T, ranging from small polar molecules to nanoparticles and vesicles (Tung & Weissleder, Advanced Drug Delivery Reviews 55: 281-294 (2003)). Thus, in embodiments of the invention, a cargo portion C and/or compound T is any suitable cargo moiety capable of being taken up by a cell while connected to a basic portion B.

For example, for in vivo imaging purposes, C and/or T may be labeled with a positron-emitting isotope (e.g. $^{18}$F) for positron emission tomography (PET), gamma-ray isotope (e.g. $^{99m}$Tc) for single photon emission computed tomography (SPECT), a paramagnetic molecule or nanoparticle (e.g. Gd$^{3+}$ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound. For therapeutic purposes, for example, suitable classes of cargo C and/or compound T include but are not limited to: a) chemotherapeutic agents such as doxorubicin, mitomycin, paclitaxel, nitrogen mustards, etoposide, camptothecin, 5-fluorouracil, etc.; b) radiation sensitizing agents such as porphyrins for photodynamic therapy, or $^{10}$B clusters or $^{157}$Gd for neutron capture therapy; or c) peptides or proteins that modulate apoptosis, the cell cycle, or other crucial signaling cascades. Existing chemotherapeutic drugs may be used, although they may not be ideal, because they have already been selected for some ability to enter cells on their own. In some embodiments of the molecules of the invention, cargoes that are unable to enter or leave cells without the help of the polybasic portion B may be employed.

In some embodiments, cargo portion C and/or compound T include a fluorescent moiety, such as a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. No. 4,452,720; U.S. Pat. No. 5,227,487 and U.S. Pat. No. 5,543,295. In some embodiments, cargo C and/or compound T includes detection agents.

In some embodiments, a cargo portion C and/or a compound T may include a fluorescein dye. Typical fluorescein dyes include, but are not limited to, 5-carboxyfluorescein, fluorescein-5-isothiocyanate and 6-carboxyfluorescein; examples of other fluorescein dyes can be found, for example, in U.S. Pat. No. 6,008,379; U.S. Pat. No. 5,750,409; U.S. Pat. No. 5,066,580 and U.S. Pat. No. 4,439,356. In some embodiments, a cargo portion C and/or compound T includes a rhodamine dye, such as, for example, tetramethylrhodamine-6-isothiocyanate, 5-carboxytetramethyrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®), and other rhodamine dyes. Other rhodamine dyes can be found, for example, in U.S. Pat. No. 6,080,852, U.S. Pat. No. 6,025,505, U.S. Pat. No. 5,936,087, U.S. Pat. No. 5,750,409. In some embodiments, a cargo portion C and/or compound T includes a cyanine dye, such as, for example, Cy3, Cy3B, Cy3.5, Cy5, Cy5.5, Cy 7, Alexa 647, IRDye-700DX and IRDYE 800CW.

Some of the above compounds or their derivatives will produce phosphorescence in addition to fluorescence, or will only phosphoresce. Some phosphorescent compounds include porphyrins, phthalocyanines, polyaromatic compounds such as pyrenes, anthracenes and acenaphthenes, and so forth, and may be, or may be included in, a cargo portion C. In some embodiments, a cargo portion C and/or compound includes a fluorescence quencher, such as, for example, a (4-dimethylamino-phenylazo)benzoic acid (DABCYL) group.

In some embodiments, a cargo moiety and/or compound T is all or part of a molecular beacon. In some embodiments a cargo moiety C and/or compound T is combined with a quencher moiety Q to form all or part of a molecular beacon. In some embodiments a cargo moiety C is combined with a quencher moiety Q (in some embodiments Q includes compound T) to form all or part of a molecular beacon. One or both of the complementary regions may be part of the cargo moiety. Where only one of the complementary regions (e.g., the fluorescent moiety) is part of the cargo moiety, and where the quencher moiety is part of the linker X and/or Y or the acidic portion A, then cleavage of the linker X and/or Y will allow fluorescence of the fluorescent portion and detection of the cleavage. Upon cellular uptake, the fluorescent portion of a molecular beacon will allow detection of the cell. For example, a quencher Q may be attached to an acidic portion A to form a MTS molecule having features of the MTS molecules of the present disclosure where cargo is fluorescent and is quenched by Q. The quenching of the cargo moiety by Q is relieved upon cleavage of X and/or Y, allowing fluorescent marking of a cell taking up portion B with cargo C and/or compound T. The combination of fluorescence quenching and selective uptake should increase contrast between tissues able to cleave X and/or Y compared to those that cannot cleave X and/or Y.

A pair of compounds may be connected to form a molecular beacon or FRET pair, having complementary regions with a fluorophore and a fluorescent quencher associated together so that the fluorescence of the fluorophore is quenched by the quencher. Such pairs can be useful as detection agents and any fluorescent pairs known or described herein can be employed with the present invention. One or both of the complementary regions may be part of the cargo portion C and/or compound T. Where only one of the complementary regions (e.g., the fluorescent moiety) is part of the cargo portion C and/or compound T, and where the quencher moiety is part of the linker X and/or Y or the acidic portion A, then cleavage of the linker X and/or Y will allow fluorescence of the fluorescent portion and detection of the cleavage. Upon cellular uptake, the fluorescent portion of a molecular beacon will allow detection of the cell. For example, a quencher Q may be attached to an acidic portion A to form a MTS molecule having features of the molecules as described in this disclosure where cargo C and/or compound T is fluorescent and is quenched by Q. The quenching of C and/or T by Q is relieved upon cleavage of X and/or Y, allowing fluorescent marking of a cell taking up portion B comprising C and/or T. The combination of fluorescence quenching and selective uptake should increase contrast between tissues able to cleave X and/or Y compared to those that cannot cleave X and/or Y.

In some embodiments, C, T and/or Q comprise all or part of a donor:acceptor FRET pair or a BRET (bioluminescence resonance energy transfer) pair. Donors can include any appropriate molecules listed herein or known in the art and as such include but are not limited to FITC; Cy3; EGFP; cyan fluorescent protein (CFP); EGFP; 6-FAM; fluorescein, IAEDANS, EDANS and BODIPY FL. Acceptors can include any appropriate molecules listed herein or known in the art and as such include but are not limited to TRITC; Cy5; Cy3; YFP; 6-FAM; LC Red 640; Alexa Fluor 546; fluorescein; tetramethylrhodamine; Dabcyl (acceptor); BODIPY FL; QSY 7, QSY 9, QSY 21 and BBQ-650 dyes. Exemplary FRET pairs can include but are not limited to CFP:YFP; 6-FAM:Cy5; Cy5:Cy7; Cy5:IRdye800CW; FITC:TRITC; Cy3:Cy5; EGFP:Cy3; EGFP:YFP; 6-FAM: LC Red 640 or Alexa Fluor 546; fluorescein:tetramethylrhodamine; IAEDANS:fluorescein; EDANS:Dabcyl; fluorescein:fluorescein; BODIPY FL:BODIPY FL; and fluorescein:QSY 7 and QSY 9 dyes.

In some embodiments, the cargo moiety C, compound T and/or quencher moiety Q are a fluorescent moiety including but not limited to a fluorescent protein, peptide, or fluorescent dye molecule. Common classes of fluorescent dyes include, but are not limited to, xanthenes such as rhodamines, rhodols and fluoresceins, and their derivatives; bimanes; coumarins and their derivatives such as umbelliferone and aminomethyl coumarins; aromatic amines such as dansyl; squarate dyes; benzofurans; fluorescent cyanines; carbazoles; dicyanomethylene pyranes, polymethine, oxabenzanthrane, xanthene, pyrylium, carbostyl, perylene, acridone, quinacridone, rubrene, anthracene, coronene, phenanthrecene, pyrene, butadiene, stilbene, lanthanide metal chelate complexes, rare-earth metal chelate complexes, and derivatives of such dyes. Fluorescent dyes are discussed, for example, in U.S. Pat. No. 4,452,720; U.S. Pat. No. 5,227,487; and U.S. Pat. No. 5,543,295.

In some embodiments, a cargo moiety C and/or quencher moiety Q are fluorescein dyes. Typical fluorescein dyes include, but are not limited to, 5-carboxyfluorescein, fluorescein-5-isothiocyanate and 6-carboxyfluorescein; examples of other fluorescein dyes can be found, for example, in U.S. Pat. No. 6,008,379, U.S. Pat. No. 5,750,409, U.S. Pat. No. 5,066,580, and U.S. Pat. No. 4,439,356. A cargo moiety C may include a rhodamine dye, such as, for example, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®), and other rhodamine dyes. Other rhodamine dyes can be found, for example, in U.S. Pat. No. 6,080,852; U.S. Pat. No. 6,025,505; U.S. Pat. No. 5,936,087; U.S. Pat. No. 5,750,409. In some embodiments, a cargo moiety C and/or a compound T includes a cyanine dye, such as, for example, Cy3, Cy3B, Cy3.5, Cy5, Cy5.5, Cy 7.

In some embodiments, cargo moiety C, compound T and/or quencher moiety Q are fluorophores. Fluorophores are commercially available and any known and/or commercially available fluorophore can be employed as the cargo moiety C and/or compound T detectable entity for the present invention. In some embodiments, the fluorophore exhibits green fluorescence (such as for example 494 nm/519 nm), orange fluorescence (such as for example 554 nm/570 nm), red fluorescence (such as for example 590 nm/617 nm), or far red fluorescence (such as for example 651 nm/672 nm) excitation/emission spectra. In some embodiments, the fluorophore is a fluorophore with excitation and emission spectra in the range of about 350 nm to about 775 nm. In some embodiments the excitation and emission spectra are about 346 nm/446 nm, about 494 nm/519 nm, about 554 nm/570 nm, about 555 nm/572 nm, about 590 nm/617 nm, about 651 nm/672 nm, about 679 nm/702 nm or about 749 nm/775 nm. In some embodiments, the fluorophore can include but is not limited to AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In some embodiments, the fluorophore can include but is not limited to Cy dyes, including Cy2, Cy3, Cy3B, Cy3.5, Cy5, Cy5.5 and Cy7 (available from GE Life Sciences or Lumiprobes). In some embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from Thermo Scientific (USA)). In some embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CRl lO (5-Carboxyrhodamine 110); 6-CRl lO (6-Carboxyrhodamine 110); 5-CR6G (5-Carboxyrhodamine 6G); 6-CR6G (6-Carboxyrhodamine 6G); 5(6)-Carboxyrhodamine 6G cadaverine; 5(6)-Carboxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carboxytetramethylrhodamine); 5-TAMRA cadaverine; 6-TAMRA cadaverine; 5-TAMRA ethylenediamme; 6-TAMRA ethylenediamme; 5-TMR C6 malemide; 6-TMR C6 malemide; TR C2 malemide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

Some of the above compounds or their derivatives will produce phosphorescence in addition to fluorescence, or will only phosphoresce. Some phosphorescent compounds include porphyrins, phthalocyanines, polyaromatic compounds such as pyrenes, anthracenes and acenaphthenes, and so forth, and in some embodiments are included in a compound T and/or a cargo moiety. In some embodiments, a cargo moiety and/or compound T include a fluorescence quencher, such as, for example, a (4-dimethylamino-phenylazo)benzoic acid (DABCYL) group.

In some embodiments, a cargo moiety and/or compound T is a fluorescent label. In some embodiments, a cargo moiety C, compound T and/or quencher moiety Q is indocarbocyanine dye, Cy5, Cy5.5, Cy7, IR800CW, or a combination thereof. In some embodiments, a cargo moiety is a MRI contrast agent. In some embodiments, a cargo moiety is Gd complex of [4,7,10-tris(carboxymethyl)-1,4,7,10-tetraazacyclododec-1-yl]acetyl.

In some embodiments, compound T and/or cargo C may include a chemotherapeutic moiety, such as a chemical compound useful in the treatment of cancer, or other therapeutic moiety, such as an agent useful in the treatment of ischemic tissue, or of necrotic tissue, or other therapeutic agent.

Multiple membrane translocation signals (MTS) have been identified. For example, the Tat protein of the human immunodeficiency virus 1 (HIV-1) is able to enter cells from the extracellular environment. A domain from Antennapedia homeobox protein is also able to enter cells.

Molecules comprising a MTS may also be used to carry other molecules into cells along with them. The most important MTS are rich in amino acids such as arginine with positively charged side chains. Molecules transported into cell by such cationic peptides may be termed "cargo" or compound T and may be reversibly or irreversibly linked to the cationic peptides.

The uptake facilitated by molecules comprising a MTS can occur with specificity by including appropriate X and/or Y linkers as well as pre-targeting P moieties, enhancing uptake into most or all cells. It is desirable to have the ability to target the delivery of cargo to a type of cell, or to a tissue, or to a location or region within the body of an animal. Accordingly, we have identified a need for a MTS molecule with increased in vivo circulation.

In some embodiments, a MTS molecule disclosed herein has the formula according to one of the following:

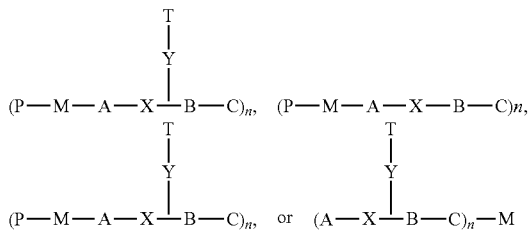

wherein C is a cargo moiety; T is a therapeutic compound; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X and/or Y is a linker that is cleavable by thrombin.

In some embodiments, a MTS molecule disclosed herein has the formula according to one of the following:

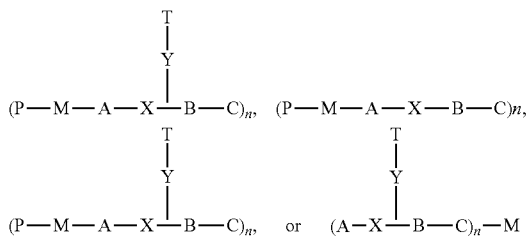

wherein C is a cargo moiety; T is a therapeutic moiety; A is a peptide with a sequence comprising 5 to 9 consecutive acidic amino acids, wherein the amino acids are selected from: aspartates and glutamates; B is a peptide with a sequence comprising 5 to 20 consecutive basic amino acids; and X and/or Y is a linker that is cleavable by thrombin.

In some embodiments, a MTS molecule disclosed herein has a formula according to one of the following:

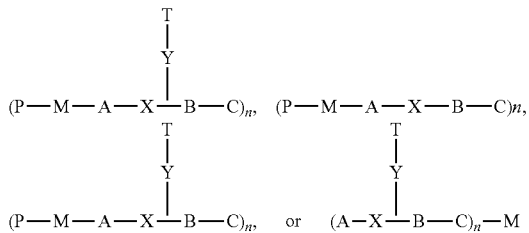

wherein C is a cargo moiety; T is a therapeutic compound; A is a peptide with a sequence comprising 5 to 9 consecutive acidic amino acids, wherein the amino acids are selected from: aspartates and glutamates; B is a peptide with a sequence comprising 5 to 20 consecutive basic amino acids; X and/or Y is a linker that is cleavable by thrombin; M is a macromolecular carrier; and n is an integer between 1 and 20.

Delivery of cargo C and/or compound T such as a fluorescent molecule may be used to visualize cells having a certain condition or cells in a region exhibiting a particular condition For example, thrombosis (clot formation) may be visualized by designing a linker X and/or Y to be cleaved by thrombin. Thus, fluorescent molecules are one example of a marker that may be delivered to target cells and regions upon release of a portion A upon cleavage of a linker X and/or Y.

In some embodiments, the cargo moiety and or compound T is selected from an imaging agent, a therapeutic agent, a lipid, a detection agent or a combination thereof.

In some embodiments, the cargo portion comprises at least two cargo moieties. In some embodiments, C comprises a marker cargo and a therapeutic cargo. Multiple cargo moieties can allow, for example, delivery of both a radioactive marker and an ultrasound or contrast agent, allowing imaging by different modalities. Alternatively, for example, delivery of radioactive cargo along with an anti-cancer agent, providing enhanced anticancer activity, or delivery of a radioactive cargo with a fluorescent cargo, allowing multiple means of localizing and identifying cells which have taken up cargo. Alternatively, delivery of a fluorescent or radioactive compound with a therapeutic compound can allow, for example, for identification of cells to which a therapeutic compound has been delivered.

In some embodiments, the compound T comprises at least two T moieties. In some embodiments, T comprises a marker cargo and a therapeutic compound. Multiple therapeutic moieties can allow, for example, delivery of both a radioactive marker and an ultrasound or contrast agent, allowing imaging by different modalities. Alternatively, for example, delivery of radioactive compound along with an anti-cancer agent, providing enhanced anticancer activity, or delivery of a radioactive cargo with a fluorescent cargo, allowing multiple means of localizing and identifying cells which have taken up compound. Alternatively, delivery of a fluorescent or radioactive compound with a therapeutic compound can allow, for example, for identification of cells to which a therapeutic compound has been delivered.

The cargo moiety is attached to B in any location or orientation. The cargo moiety need not be located at an opposite end of portion B than a linker X and/or Y. Any location of attachment of the cargo moiety to B is acceptable as long as that attachment remains after X is cleaved. For example, the cargo moiety may be attached to or near to an end of portion B with linker X and/or Y is attached to an opposite end of portion B. The cargo moiety may also be attached to or near to an end of portion B with linker X attached to or near to the same end of portion B.

In some embodiments, a cargo moiety C and/or compound T is a fluorescent molecule such as fluorescein. Fluorescent cargo moieties enable easy measurement by fluorescence microscopy or flow cytometry in unfixed cultured cells. In some embodiments, T is a therapeutic moiety capable of use in treating a variety of diseases, including inflammation, diabetes, cardiovascular diseases, neurodegenerative disorders and cancer.

In some embodiments, a cargo moiety and/or compound T is labeled with a positron-emitting isotope (e.g., 18F) for positron emission tomography (PET), gamma-ray isotope (e.g., 99mTc) for single photon emission computed tomography (SPECT), a paramagnetic molecule or nanoparticle (e.g., Gd3+ chelate or coated magnetite nanoparticle) for magnetic resonance imaging (MRI), a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, cargo C and/or compound T includes a radioactive moiety, for example a radioactive isotope such as $^{211}$At, $^{131}$I, $^{125}$I, $^{90}$Y, $^{186}$Re, $^{188}$Re, $^{153}$Sm, $^{212}$Bi, $^{32}$P, $^{64}$Cu and $^{89}$Zr. In some embodiments, a cargo moiety is a radioactive moiety, for example a radioactive isotope such as $^{211}$At, $^{131}$I, $^{125}$I, $^{90}$Y, $^{186}$Re, $^{188}$Re, $^{148}$Sm, $^{133}$Ba, $^{212}$Bi, $^{12}$P, $^{3}$H, $^{14}$C, $^{32}$P, $^{35}$S, $^{87}$Rb, $^{90}$Sr, $^{115}$In, $^{123}$Te, $^{130}$Te, $^{131}$I, $^{137}$Cs, $^{138}$La, $^{144}$Nd, $^{147}$Sm, $^{148}$Sm, $^{176}$Lu, $^{187}$Re, $^{186}$Os, $^{222}$Rn, $^{226}$Ra, Barium-133, Cadmium-109, Cobalt-57, Cobalt-60, Europium-152, Manganese-54, Sodium-22, Zinc-65, Technetium-99m, Strontium-90, Thallium-204, Carbon-14, Tritium (Hydrogen-3), radioactive isotopes of Lu, Cu and Zr as well as others known to those of skill in the art.

In some embodiments, a cargo moiety and/or a therapeutic moiety are a therapeutic agent, such as a chemical compound useful in the treatment of cancer, ischemic tissue, or necrotic tissue.

For therapeutic purposes, for example, suitable classes of cargo moiety (C) and/or therapeutic moiety (T) include but are not limited to a) chemotherapeutic agents, b) radiation sensitizing agents, or c) peptides or proteins that modulate apoptosis, the cell cycle, or other crucial signaling cascades.

In some embodiments, a cargo moiety (C) or a therapeutic moiety (T) is an agent that treats a cardiovascular disorder. In some embodiments, the cargo moiety is a niacin, a fibrate, a statin, an Apo-Al mimetic peptide, an apoA-I transcriptional up-regulator, an ACAT inhibitor, a CETP modulator, or a combination thereof, a Glycoprotein (GP) IIb/IIIa receptor antagonist, a P2Y 12 receptor antagonist, a Lp-PLA2-inhibitor, a leukotriene inhibitor, a MIF antagonist, or a combination thereof In some embodiments the cargo moiety is atorvastatin, cerivastatin, fluvastatin, lovastatin, mevastatin, pitavastatin, pravastatin, rosuvastatin, simvastatin, simvastatin and ezetimibe, lovastatin and niacin, extended-release, atorvastatin and amlodipine besylate, simvastatin and niacin, extended-release, bezafibrate, ciprofibrate, clofibrate, gemfibrozil, fenofibrate, DF4 (Ac-D-W-F-K-A-F-Y-D-K-V-A-E-K-F-K-E-A-F-NH2), DF5, RVX-208 (Resverlogix), avasimibe, pactimibe sulfate (CS-505), CI-1011 (2,6-diisopropylphenyl[(2,4,6-triisopropylphenyl) acetyl]sulfamate), CI-976 (2,2-dimethyl-N-(2,4,6-trimethoxyphenyl)dodecanamide), VULM 1457 (1-(2,6-diisopropyl-phenyl)-3-[4-(4'-mtrophenylthio)phenyl]urea), CI-976 (2,2-dimethyl-N-(2,4,6-trimethoxyphenyl)dodecanamide), E-5324 (n-butyl-N'-(2-(3-(5-ethyl-4-phenyl-1H-imidazol-1-yl)propoxy)-6-methylphenyl)urea), HL-004 (N-(2,6-diisopropylphenyl)tetradecylthioacetamide), KY-455 (N-(4,6-dimethyl-1-pentylindolin-7-yl)-2,2-dimethylpropanamide), FY-087 (N-[2-[N'-pentyl-(6,6-dimethyl-2,4-heptadiynyl)amino]ethyl]-(2-methyl-1-naphthyl-thio)acetamide), MCC-147 (Mitsubishi Pharma), F 1251 1 ((S)-2',3',5'-trimethyl-4'-hydroxy-alpha-dodecylthioacetanihde), SMP-500 (Sumitomo Pharmaceuticals), CL 277082 (2,4-difluoro-phenyl-N[[4-(2,2-dimethylpropyl)phenyl]methyl]-Neptyl)urea), F-1394 ((1s,2s)-2[3-(2,2-dimethylpropyl)-3-nonylureido]aminocyclohexane-1-yl 3-[N-(2,2,5,5-tetramethyl-1,3-dioxane-4-carbonyl)amino]propionate), CP-113818 (N-(2,4-bis(methylthio)-6-methylpyridin-3-yl)-2-(hexylthio)decanoic acid amide), YM-750, torcetrapib, anacetrapid, JTT-705 (Japan Tobacco/Roche), abciximab, eptifibatide, tirofiban, roxifiban, variabihn, XV 459 (N(3)-(2-(3-(4-formamidinophenyl)isoxazolm-5-yl)acetyl)-N(2)-(1-butyloxycarbonyl)-2,3-diaminopropionate), SR 121566A (3-[N-{4-[4-(aminoiminomethyl)phenyl]-1,3-thiazol-2-yl J-N-(I-carboxymethylpiperid-4-yl)aminol propionic acid, trihydrochloride), FK419 ((S)-2-acetylamino-3-[(R)-[1-[3-(piperidin-4-yl)propionyl]piperidin-3-ylcarbonyl]amino] propionic acid trihydrate), clopidogrel, prasugrel, cangrelor, AZD6140 (AstraZeneca); MRS 2395 (2,2-Dimethyl-propionic acid 3-(2-chloro-6-methylaminopurin-9-y])-2-(2,2-dimethyl-propionyloxymethyl)-propyl ester); BX 667 (Berlex Biosciences); BX 048 (Berlex Biosciences); darapladib (SB 480848); SB-435495 (GlaxoSmithKline); SB-222657 (GlaxoSmithKline); SB-253514 (GlaxoSmithKline); A-81834 (3-(3-(1,1-dimethylethylthio-5-(quinoline-2-yl-methoxy)-1-(4-chloromethylphenyl)indole-2-yl)-2,2-dimethylpropionaldehyde oxime-O-2-acetic acid; AME103 (Amira); AME803 (Amira); atreleuton; BAY-x-1005 ((R)-(+)-alpha-cyclopentyl-4-(2-quinolinylmethoxy)-Benzeneacetic acid); CJ-13610 (4-(3-(4-(2-Methyl-imidazol-1-yl)-phenylsulfanyl)-phenyl)-tetrahydro-pyran-4-carboxylic acid amide); DG-031 (DeCode); DG-051 (DeCode); MK886 (1-[(4-chlorophenyl)methyl]3-[(1,1-dimethylethyl) thio]-α,α-dimethyl-5-(1-methylethyl)-1H-indole-2-propanoic acid, sodium salt); MK591 (3-(1-4[(4-chlorophenyl) methyl]-3-[(t-butylthio)-5-((2-quinoly)methoxy)-1H-indole-2]-, dimethylpropanoic acid); RP64966 ([4-[5-(3-Phenyl-propyl)thiophen-2-yl]butoxy]acetic acid); SA6541 ((R)—S-[[4-(dimethylamino)phenyl]methyl]-N-(3-mercapto-2methyl-1-oxopropyl-L-cysteine); SC-56938 (ethyl-1-[2-[4-(phenylmethyl)phenoxy]ethyl]-4-piperidine-carboxylate); VIA-2291 (Via Pharmaceuticals); WY-47,288 (2-[(1-naphthalenyloxy)methyl]quinoline); zileuton; ZD-2138 (6-((3-fluoro-5-(tetrahydro-4-methoxy-2H-pyran-4yl)phenoxy)methyl)-]-methyl-2(1H)-quinolinone); or combinations thereof.

In some embodiments, a cargo moiety (C) or a therapeutic moiety (T) is a drug. In some embodiments, the drug is an agent that modulates death (e.g., via apoptosis or necrosis) of a cell. In some embodiments, the drug is a cytotoxic agent. In some embodiments, the drug is monomethyl auristatin E (MMAE), monomethyl auristatin F (MMAF), maytansine, methotrexate (RHEUMATREX®, Amethopterin); cyclophosphamide (CYTOXAN®); thalidomide (THALIDOMID®); paclitaxel; pemetrexed; pentostatin; pipobroman; pixantrone; plicamycin; procarbazine; proteasome inhibitors (e.g., bortezomib); raltitrexed; rebeccamycin; rubitecan; SN-38; salinosporamide A; satraplatin; streptozotocin; swainsonine; tariquidar, taxane; tegafur-uracil; temozolomide; testolactone; thioTEPA; tioguanine; topotecan; trabectedin; tretinoin; triplatin tetranitrate; tris(2-chloroethyl)amine; troxacitabine; uracil mustard; valrubicin; vinblastine; vincristine; vinorelbine; vorinostat; zosuquidar, or a combination thereof. In some embodiments, the drug is a pro-apoptotic agent. In some embodiments, the drug is an anti-apoptotic agent. In some embodiments, the drug is selected from: minocycline; SB-203580 (4-(4-Fluorophenyl)-2-(4-methylsulfinyl phenyl)-5-(4-pyridyl)1H-imidazole); PD 169316 (4-(4-Fluorophenyl)-2-(4-nitrophenyl)-5-(4-pyridyl)-1H-imidazole); SB 202190 (4-(4-Fluorophenyl)-2-(4-hydroxyphenyl)-5-(4-pyridyl)1H-imidazole); RWJ 67657 (4-[4-(4-fluorophenyl)-1-(3-phenylpropyl)-5-(4-pyridinyl)-1H-imidazol-2-yl]-3-butyn-1-ol); SB 220025 (5-(2-Amino-4-pyrimidinyl)-4-(4-fluorophenyl)-1-(4-piperidinyl)imidazole); D-JNKI-I ((D)-hJIP175-157-DPro-DPro-(D)-HIV-TAT57-48); AM-111 (Auris); SP600125 (anthra[1,9-cd]pyrazol-6(2H)-one); JNK Inhibitor I ((L)-HIV-T AT48-57-PP-JBD20); JNK Inhibitor III ((L)-HIV-T AT47-57-gaba-c-Junδ33-57); AS601245 (1,3-benzothiazol-2-yl (2-[[2-(3-pyridinyl)ethyl]amino]-4 pyrimidinyl)acetonitrile); JNK Inhibitor VI (H2N-RPKRPT-TLNLF-NH2); JNK Inhibitor VIII (N-(4-Amino-5-cyano-6-ethoxypyridin-2-yl)-2-(2,5-dimethoxyphenyl)acetamide); JNK Inhibitor IX (N-(3-Cyano-4,5,6,7-tetrahydro-1-benzothien-2-yl)-1-naphthamide); dicumarol (3,3'-Methylenebis (4-hydroxycoumarin)); SC-236 (4-[5-(4-chlorophenyl)-3-

(trifluoromethyl)-1H-pyrazol-1-yl]benzene-sulfonamide); CEP-1347 (Cephalon); CEP-11004 (Cephalon); an artificial protein comprising at least a portion of a Bcl-2 polypeptide; a recombinant FNK; V5 (also known as Bax inhibitor peptide V5); Bax channel blocker ((±)-1-(3,6-Dibromocarbazol-9-yl)-3-piperazin-1-yl-propan-2-ol); Bax inhibiting peptide P5 (also known as Bax inhibitor peptide P5); Kp7-6; FAIM(S) (Fas apoptosis inhibitory molecule-short); FAIM (L) (Fas apoptosis inhibitory molecule-long); Fas:Fc; FAP-I; NOK2; F2051; Fl 926; F2928; ZB4; Fas M3 mAb; EGF; 740 Y-P; SC 3036 (KKHTDDGYMPMSPGVA); PI 3-kinase Activator (Santa Cruz Biotechnology, Inc.); Pam3Cys ((S)-(2,3-bis(palmitoyloxy)-(2RS)-propyl)-N-palmitoyl-(R)-Cys-(S)-Ser(S)-Lys4-OH, trihydrochloride); Act1 (NF-kB activator 1); an anti-IkB antibody; Acetyl-11-keto-b-Boswellic Acid; Andrographolide; Caffeic Acid Phenethyl Ester (CAPE); Gliotoxin; Isohelenin; NEMO-Binding Domain Binding Peptide (DRQIKIWFQNRRMKWKK-TALDWSWLQTE); NF-kB Activation Inhibitor (6-Amino-4-(4-phenoxyphenylethylamino)quinazoline); NF-kB Activation Inhibitor II (4-Methyl-N1-(3-phenylpropyl)benzene-1,2-diamine); NF-kB Activation Inhibitor III (3-Chloro-4-nitro-N-(5-nitro-2-thiazolyl)-benzamide); NF-kB Activation Inhibitor IV ((E)-2-Fluoro-4'-methoxystilbene); NF-kB Activation Inhibitor V (5-Hydroxy-(2,6-diisopropylphenyl)-1H-isoindole-1,3-dione); NF-kB SN50 (AAVALLPAVL-LALLAPVQRKRQKLMP); Oridonin; Parthenolide; PPM-18 (2-Benzoylamino-1,4-naphthoquinone); RoI 06-9920; Sulfasalazine; TIRAP Inhibitor Peptide (RQIKIWFNRRM-KWKKLQLRDAAPGGAIVS); Withaferin A; Wogonin; BAY 1 1-7082 ((E)3-[(4-Methylphenyl)sulfonyl]-2-propenenitrile); BAY 1 1-7085 ((E)3-[(4-t-Butylphenyl)sulfonyl]-2-propenenitrile); (E)-Capsaicin; Aurothiomalate (ATM or AuTM); Evodiamine; Hypoestoxide; IKK Inhibitor m (BMS-345541); IKK Inhibitor VII; IKK Inhibitor X; IKK Inhibitor II; IKK-2 Inhibitor IV; IKK-2 Inhibitor V; IKK-2 Inhibitor VI; IKK-2 Inhibitor (SC-514); IkB Kinase Inhibitor Peptide; IKK-3 Inhibitor IX; ARRY-797 (Array BioPharma); SB-220025 (5-(2-Amino-4-pyrimidinyl)-4-(4-fluorophenyl)-1-(4-piperidinyl)imidazole); SB-239063 (trans-4-[4-(4-Fluorophenyl)-5-(2-methoxy-4-pyrimidinyl)-1H-imidazol-1-yl]cyclohexanol); SB-202190 (4-(4-Fluorophenyl)-2-(4-hydroxyphenyl)-5-(4-pyridyl)1H-imidazole); JX-401 (-[2-Methoxy-4-(methylthio)benzoyl]-4-(phenylmethyl)piperidine); PD-169316 (4-(4-Fluorophenyl)-2-(4-nitrophenyl)-5-(4-pyridyl)-1H-imidazole); SKF-86002 (6-(4-Fluorophenyl)-2,3-dihydro-5-(4-pyridinyl)imidazo[2,1-b]thiazole dihydrochloride); SB-200646 (N-(I-Methyl-1H-indol-5-yl)-N'-3-pyridinylurea); CMPD-I (2'-Fluoro-N-(4-hydroxyphenyl)-[1,1'-biphenyl]-4-butanamide); EO-1428 ((2-Methylphenyl)-[4-[(2-amino-4-bromophenyl)amino]-2-chlorophenyl]methanone); SB-253080 (4-[5-(4-Fluorophenyl)-2-[4-(methylsulfonyl) phenyl]-1H-imidazol-4-yl]pyridine); SD-169 (1H-Indole-5-carboxamide); SB-203580 (4-(4-Fluorophenyl)-2-(4-methylsulfinyl phenyl)-5-(4-pyridyl)1H-imidazole); TZP-101 (Tranzyme Pharma); TZP-102 (Tranzyme Pharma); GHRP-6 (growth hormone-releasing peptide-6); GHRP-2 (growth hormone-releasing peptide-2); EX-1314 (Elixir Pharmaceuticals); MK-677 (Merck); L-692,429 (Butanamide, 3-amino-3-methyl-N-(2,3,4,5-tetrahydro-2-oxo-1-((2'-(1H-tetrazol-5-yl)(1,1'-biphenyl)-4-yl)methyl)-1H-1-benzazepin-3-yl)-, (R)—); EPI 572 (Aib-DTrp-DgTrp-CHO); diltiazem; metabolites of diltiazem; BRE (Brain and Reproductive organ-Expressed protein); verapamil; nimodipine; diltiazem; omega-conotoxin; GVIA; amlodipine; felodipine; lacidipine; mibefradil; NPPB (5-Nitro-2-(3-phenylpropylamino)benzoic Acid); flunarizine; erythropoietin; piperine; hemin; brazilin; z-V AD-FMK (Benzyloxycarbonyl-Val-Ala-Asp(OMe)-fluoromethylketone); z-LEHD-FMK (benzyloxycarbonyl-Leu-Glu(OMe)-His-Asp(OMe)-fluoromethylketone); B-D-FMK (boc-aspartyl(Ome)-fluoromethylketone); Ac-LEHD-CHO (N-acetyl-Leu-Glu-His-Asp-CHO); Ac-IETD-CHO (N-acetyl-Ile-Glu-Thr-Asp-CHO); z-IETD-FMK (benzyloxycarbonyl-Ile-Glu(OMe)-Thr-Asp(OMe)-fluoromethyl ketone); FAM-LEHD-FMK (benzyloxycarbonyl Leu-Glu-His-Asp-fluoromethyl ketone); FAM-LETD-FMK (benzyloxycarbonyl Leu-Glu-Thr-Asp-fluoromethyl ketone); Q-VD-OPH (Quinoline-Val-Asp-CH2-O-Ph); XIAP; cIAP-1; cIAP-2; ML-IAP; ILP-2; NAIP; Survivin; Bruce; IAPL-3; fortilin; leupeptine; PD-150606 (3-(4-Iodophenyl)-2-mercapto-(Z)-2-propenoic acid); MDL-28170 (Z-Val-Phe-CHO); calpeptin; acetyl-calpastatin; MG 132 (N-t(phenylmethoxy)carbonyl]-L-leucyl-N-[(IS)-1-formyl-3-methylbutyl]-L-leucinamide); MYO-DUR; BN 82270 (Ipsen); BN 2204 (Ipsen); AHLi-11 (Quark Pharmaceuticals), an mdm2 protein, pifithrin-α (1-(4-Methylphenyl)-2-(4,5,6,7-tetrahydro-2-imino-3(2H)-benzothiazolyl)ethanone); trans-stilbene; cis-stilbene; resveratrol; piceatannol; rhapontin; deoxyrhapontin; butein; chalcon; isoliquirtigen; butein; 4,2',4'-trihydroxychalcone; 3,4,2',4',6'-pentahydroxychalcone; flavone; morin; fisetin; luteolin; quercetin; kaempferol; apigenin; gossypetin; myricetin; 6-hydroxyapigenin; 5-hydroxyflavone; 5,7,3',4',5'-pentahydroxyflavone; 3,7,3',4',5'-pentahydroxyflavone; 3,6,3',4'-tetrahydroxyflavone; 7,3',4',5'-tetrahydroxyflavone; 3,6,2',4'-tetrahydroxyflavone; 7,4'-dihydroxyflavone; 7,8,3',4'-tetrahydroxyflavone; 3,6,2',3'-tetrahydroxyflavone; 4'-hydroxyflavone; 5-hydroxyflavone; 5,4'-dihydroxyflavone; 5,7-dihydroxyflavone; daidzein; genistein; naringenin; flavanone; 3,5,7,3',4'-pentahydroxyflavanone; pelargonidin chloride; cyanidin chloride; delphinidin chloride; (−)-epicatechin (Hydroxy Sites: 3,5,7,3',4'); (−)-catechin (Hydroxy Sites: 3,5,7,3',4'); (−)-gallocatechin (Hydroxy Sites: 3,5,7,3',4',5') (+)-catechin (Hydroxy Sites: 3,5,7,3',4'); (+)-epicatechin (Hydroxy Sites: 3,5,7,3',4'); Hinokitiol (b-Thujaplicin; 2-hydroxy-4-isopropyl-2,4,6-cycloheptatrien-1-one); L-(+)-Ergothioneine ((S)-a-Carboxy-2,3-dihydro-N,N,N-trimethyl-2-thioxo-1H-imidazole4-ethanaminium inner salt); Caffeic Acid Phenyl Ester; MCI-186 (3-Methyl-1-phenyl-2-pyrazolin-5-one); HBED (N,N'-Di-(2-hydroxybenzyl)ethylenediamine-N,N'-diacetic acid*$H_2O$); Ambroxol (trans-4-(2-Amino-3,5-dibromobenzylamino)cyclohexane-HCl; and U-83836E ((−)-2-((4-(2,6-di-1-Pyrrolidinyl-4-pyrimidinyl)-1-piperazinyl)methyl)-3,4-dihydro-2,5,7,8-tetramethyl-2H-1-benzopyran-6-ol*2HCl); β-1'-5-methyl-nicotinamide-2'-deoxyribose; β-D-r-5-methyl-nico-tinamide-2'-deoxyribofuranoside; β-1'-4,5-dimethyl-nicotinamide-2'-de-oxyribose; β-D-1'-4,5-dimethyl-nicotinamide-2'-deoxyribofuranoside; 1-Naphthyl PPI (1-(1,1-Dimethylethyl)-3-(1-naphthalenyl)-1H-pyrazolo[3,4-d]pyrimidin-4-amine); Lavendustin A (5-[[(2,5-Dihydroxyphenyl)methyl][(2-hydroxyphenyl)methyl]amino]-2-hydroxybenzoic acid); MNS (3,4-Methylenedioxy-b-nitrostyrene), PPI (1-(1,1-Dimethylethyl)-1-(4-methylphenyl)-1H-pyrazolo[3,4-d]pyrimidin-4-amine), PP2 (3-(4-chlorophenyl) 1-(1,1-dimethylethyl)-1H-pyrazolo[3,4-d]pymidin-4-amine, KX-004 (Kinex), KX-005 (Kinex), KX-136 (Kinex), KX-174 (Kinex), KX-141 (Kinex), KX2-328 (Kinex), KX-306 (Kinex), KX-329 (Kinex), KX2-391 (Kinex), KX2-377 (Kinex), ZD4190 (Astra Zeneca, N-(4-bromo-2-fluorophenyl)-6-methoxy-7-(2-(1H-1,2,3-triazol-1-yl)ethoxy)quinazolin-4-amine), AP22408 (Ariad Pharmaceuticals), AP23236 (Ariad Pharmaceuticals), AP23451

(Ariad Pharmaceuticals), AP23464 (Ariad Pharmaceuticals), AZD0530 (Astra Zeneca), AZM475271 (M475271, Astra Zeneca), Dasatmib (N-(2-chloro-6-methylphenyl)-2-(6-(4-(2-hydroxyethyl)-piperazin-1-yl)-2-methylpyrimidin-4-ylamino) thiazole-5-carboxamide), GN963 (trans-4-(6,7-dimethoxyquinoxalim-2ylamino)cyclohexanol sulfate); Bosutimb (4-((2,4-dichloro-5-methoxyphenyl)amino)-6-methoxy-7-(3-(4-methyl-1-piperazinyl)propoxy)-3-quinolinecarbonitrile), or combinations thereof. In some embodiments, C and/or T is monomethyl auristatin E (MMAE) or monomethyl auristatin F (MMAF).

In some embodiments, a MTS molecule as disclosed herein further comprises a lipid, L. In some embodiments, the MTS comprises a lipid L, A is a peptide with a sequence comprising 5 to 9 consecutive acidic amino acids, wherein the amino acids are selected from aspartates and glutamates, B is a peptide with a sequence comprising 5 to 20 consecutive basic amino acids, X and/or Y is a linker, and n is an integer between 1 and 20, and wherein L is bound to an MTS as disclosed herein by a bond with a B.

In some embodiments, the lipid entraps a hydrophobic molecule. In some embodiments, the lipid entraps at least one agent selected from the group consisting of a therapeutic moiety or an imaging moiety.

In some embodiments, the lipid is PEGylated. In some embodiments, the lipid is PEG(2K)-phosphatidylethanolamine.

Disclosed herein, in certain embodiments, is a MTS molecule with increased in vivo circulation. In some embodiments, a MTS molecule disclosed herein has the formula according to one of the following:

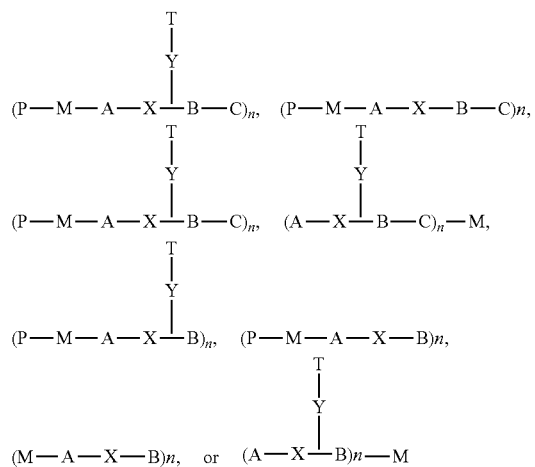

wherein C is a cargo moiety; T is a compound; A is a peptide with a sequence comprising 5 to 9 consecutive acidic amino acids, wherein the amino acids are selected from aspartates and glutamates, B is a peptide with a sequence comprising 5 to 20 consecutive basic amino acids; X and/or Y is a linker, M is a macromolecular carrier; and n is an integer between 1 and 20.

The term "macromolecular carrier" indicates an inert molecule that increases (a) plasma half-life and (b) solubility. In some embodiments, a macromolecular carrier decreases uptake of a MTS molecule into cartilage. In some embodiments, a macromolecular carrier decreases uptake of a MTS molecule into joints. In some embodiments, a macromolecular carrier decreases uptake of a MTS molecule into the liver. In some embodiments, a macromolecular carrier decreases uptake of a MTS molecule into kidneys.

In some embodiments, a macromolecular carrier M increases plasma half-life and solubility by reducing glomerular filtration. In some embodiments, a macromolecular carrier increases tumor uptake due to enhanced permeability and retention (EPR) of tumor vasculature.

In some embodiments, M is bound to A. In some embodiments, M is bound to A at the n-terminal poly glutamate. In some embodiments, M is bound to A (or, the n-terminal poly glutamate) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond.

In some embodiments, M is bound to B. In some embodiments, M is bound to B at the c-terminal polyarginine. In some embodiments, M is bound to B (or, the c-terminal polyarginine) by a covalent linkage. In some embodiments, the covalent linkage comprises an ether bond, thioether bond, amine bond, amide bond, carbon-carbon bond, carbon-nitrogen bond, carbon-oxygen bond, or carbon-sulfur bond. In some embodiments, M is bound to A.

In some embodiments, M is selected from a protein, a synthetic or natural polymer, or a dendrimer. In some embodiments, M is a dendrimer, dextran (including for example but not limited to branched glucan/branched glucose molecules composed of chains of varying lengths ranging from 3 to 2000 kDa with molecular weights ranging from 3 kDa to 2,000 kDa, for example but not limited to 20 kDa, 40 kDa, 60 kDa and 100 kDa), a PEG polymer (e.g., PEG 5 kDa, PEG 10 kDa, PEG 12 kDa, PEG 15 kDa, PEG 20 kDa, PEG 40 kDa, PEG 50 kDa or PEG 100 kDa), albumin or fragments thereof, lipid-coated perfluorocarbon droplet or a combination thereof. In some embodiments, M is a PEG polymer.

In some embodiments, the size of the macromolecular carrier is between 50 kDa and 70 kDa. In some embodiments, small amounts of negative charge keep peptides out of the liver while not causing synovial uptake.

In some embodiments, the MTS molecule is conjugated to albumin. In certain instances, albumin is excluded from the glomerular filtrate under normal physiological conditions. In some embodiments, the MTS molecule comprises a reactive group such as maleimide that can form a covalent conjugate with albumin. A MTS molecule comprising albumin results in enhanced accumulation of cleaved MTS molecules in tumors in a cleavage dependent manner. In some embodiments, albumin conjugates have good pharmacokinetic properties but are difficult to work with synthetically.

In some embodiments, the MTS molecule is conjugated to a PEG polymer. In some embodiments, the MTS molecule is conjugated to a PEG 5 kDa polymer. In some embodiments, the MTS molecule is conjugated to a PEG 12 kDa polymer. In some embodiments, 5 kDa PEG conjugates behaved similarly to free peptides. In some embodiments, 12 kDa PEG conjugates had a longer half-life as compared to free peptides. See Example 5 for a detailed analysis of the effects of using a PEG polymer.

In some embodiments, the MTS molecule is conjugated to a dextran. In some embodiments, the MTS molecule is conjugated to a 70 kDa dextran. In some embodiments, dextran conjugates, being a mixture of molecular weights, are difficult to synthesize and purify reproducibly.

In some embodiments, the MTS molecule is conjugated to streptavidin.

In some embodiments, the MTS molecule is conjugated to a fifth generation PAMAM dendrimer.

In some embodiments, a macromolecular carrier is capped. In some embodiments, capping a carrier improves the pharmacokinetics and reduces cytotoxicity of a macromolecular carrier by adding hydrophilicity. In some embodiments, the cap is selected from: Acetyl, succinyl, 3-hydroxypropionyl, 2-sulfobenzoyl, glycidyl, PEG-2, PEG-4, PEG-8 and PEG-12.

In some embodiments, the macromolecular carrier comprises a dendrimer. As used herein, "dendrimer" means a poly-functional (or, poly-branched) molecule. In some embodiments, a dendrimer is a structure in which a central molecule branches repetitively and repetitiously. In some embodiments, the dendrimer is a nanoparticle. In some embodiments, the dendrimer comprises a reactive group such as maleimide that can form a covalent conjugate with albumin. In some embodiments, a dendrimer is conjugated to a MTS molecule via a maleimide linker at the C-terminal end of the MTS molecule. In some embodiments, when the MTS molecule comprises a dendrimer, the cargo and/or compound T is attached directly to D.

In some embodiments, conjugating a MTS molecule to a dendrimer increases plasma half-life as compared to an unconjugated (or, free) MTS molecule. In some embodiments, a MTS molecule conjugated to a dendrimer results in a decrease in acute toxicity as compared to unconjugated MTS molecules. In some embodiments, a MTS molecule conjugated to a dendrimer reduces uptake by synovium, cartilage and kidney as compared to unconjugated MTS molecules.

In some embodiments, a MTS molecule conjugated to a dendrimeric nanoparticle is used to target tumor associated macrophages. In some embodiments, a MTS molecule conjugated to a dendrimeric nanoparticle, wherein the nanoparticle further comprises Ricin A, is used to poison subcutaneous macrophages.

MTS molecules having features of disclosed herein may be synthesized by standard synthetic techniques, such as, for example, solid phase synthesis including solid phase peptide synthesis. (An example of peptide synthesis using Fmoc is given as Example 1 in WO 2005/042034). For example, conventional solid phase methods for synthesizing peptides may start with N-alpha-protected amino acid anhydrides that are prepared in crystallized form or prepared freshly in solution, and are used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1 to 2 reaction cycles are used for the first twelve residue additions, and 2 to 3 reaction cycles for the remaining residues.

After completing the growing peptide chains, the protected peptide resin is treated with a strong acid such as liquid hydrofluoric acid or trifluoroacetic acid to deblock and release the peptides from the support. For preparing an amidated peptide, the resin support used in the synthesis is selected to supply a C-terminal amide, after peptide cleavage from the resin. After removal of the strong acid, the peptide may be extracted into 1M acetic acid solution and lyophilized. The peptide can be isolated by an initial separation by gel filtration, to remove peptide dimers and higher molecular weight polymers, and also to remove undesired salts The partially purified peptide may be further purified by preparative HPLC chromatography, and the purity and identity of the peptide confirmed by amino acid composition analysis, mass spectrometry and by analytical HPLC (e.g., in two different solvent systems).

The invention also provides polynucleotides encoding MTS molecules described herein. The term "polynucleotide" refers to a polymeric form of nucleotides of at least 10 bases in length. The nucleotides can be ribonucleotides, deoxynucleotides, or modified forms of either type of nucleotide. The term includes single and double stranded forms of DNA. The term therefore includes, for example, a recombinant DNA which is incorporated into a vector, e.g., an expression vector; into an autonomously replicating plasmid or virus; or into the genomic DNA of a prokaryote or eukaryote, or which exists as a separate molecule (e.g., a cDNA) independent of other sequences.

These polynucleotides include DNA, cDNA, and RNA sequences which encode MTS molecules having features of the invention, or portions thereof. Peptide portions may be produced by recombinant means, including synthesis by polynucleotides encoding the desired amino acid sequence. Such polynucleotides may also include promoter and other sequences, and may be incorporated into a vector for transfection (which may be stable or transient) in a host cell.

The construction of expression vectors and the expression of genes in transfected cells involves the use of molecular cloning techniques that are well known in the art. See, for example, Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc., most recent Supplement). Nucleic acids used to transfect cells with sequences coding for expression of the polypeptide of interest generally will be in the form of an expression vector including expression control sequences operatively linked to a nucleotide sequence coding for expression of the polypeptide. As used herein, "operatively linked" refers to a juxtaposition wherein the components so described are in a relationship permitting them to function in their intended manner. A control sequence operatively linked to a coding sequence is ligated such that expression of the coding sequence is achieved under conditions compatible with the control sequences. "Control sequence" refers to polynucleotide sequences which are necessary to effect the expression of coding and non-coding sequences to which they are ligated. Control sequences generally include promoter, ribosomal binding site, and transcription termination sequence. The term "control sequences" is intended to include, at a minimum, components whose presence can influence expression, and can also include additional components whose presence is advantageous, for example, leader sequences and fusion partner sequences. As used herein, the term "nucleotide sequence coding for expression of a polypeptide refers to a sequence that, upon transcription and translation of mRNA, produces the polypeptide. This can include sequences containing, e.g., introns. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons.

Any suitable method is used to construct expression vectors containing the fluorescent indicator coding sequence and appropriate transcriptional/translational control signals. Any methods which are well known to those skilled in the art can be used to construct expression vectors containing the fluorescent indicator coding sequence and appropriate transcriptional/translational control signals. These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989). Transformation of a host cell with recombinant DNA may be carried out by conventional techniques as are well known to those skilled in the art.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the fusion polypeptide of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukagotic Viral Vectors*, Cold Spring Harbor Laboratory, Gluzman ed., 1982). Techniques for the isolation and purification of polypeptides of the invention expressed in prokaryotes or eukaryotes may be by any conventional means such as, for example, preparative chromatographic separations and immunological separations such as those involving the use of monoclonal or polyclonal antibodies or antigen.

It will be understood that the compounds of the present invention can be formulated in pharmaceutically and or diagnostically useful compositions. Such pharmaceutical and diagnostically useful compositions may be prepared according to well known methods. For example, MTS compounds having features of the invention, and having a cargo portion C that is, for example, a therapeutic moiety or a detection moiety, may be combined in admixture with a pharmaceutically acceptable carrier vehicle or a diagnostic buffering agent. Suitable vehicles and agents and their formulation, inclusive of other human proteins, e.g. human serum albumin are described, for example, in *Remington's Pharmaceutical Sciences* by E. W. Martin and, the techniques described in Maniatis, et al., Molecular Cloning A Laboratory Manual, Cold Spring Harbor Laboratory, N.Y., 1989-2013, which are hereby incorporated by reference. Such compositions will contain an effective amount of the compounds hereof together with a suitable amount of vehicle in order to prepare pharmaceutically acceptable compositions suitable for effective administration. Dosages and dosing regimens may be determined for the indications and compounds by methods known in the art, including determining (e.g., in experimental animals) the effective dose which causes half of those treated to respond to the treatment ($ED_{50}$) by providing a range of doses to experimental animals or subjects and noting the responses.

Methods of Use

The MTS molecules find use in a variety of ex vivo applications as described herein and such MTS molecules have been thoroughly described (see, WO 2005/042034, WO/2006/125134, WO2011008992 and WO2011008996; all of which are incorporated herein by reference in their entireties). As such, according to disclosure contained herein, this invention pertains to methods and compositions that find use in treatment, diagnostic, prognostic (e.g., patient prognosis) and characterization (e.g., histologic grade/stage) of neoplasia and neoplasma samples based on the ability of a tumor sample to cleave a MTS molecule of the present invention.

Methods of use and compositions comprising MTS molecules are disclosed. Molecules having features of the invention include peptide portions linked by a cleavable linker portion which may be a peptide. The inventors have found that these MTS molecules can find use in treatment, diagnostic, detection, screening, prognosis (e.g., patient prognosis) and characterization (e.g., histologic grade/stage) assays.

According to the present invention, such methods are based in part on cleavage of the MTS molecule and detection of that cleavage event. The presence of one or more proteases in a sample from a subject can be detected ex vivo based on cleavage of the peptide. Such cleavage is detected by detecting a change in a detectable label (detectable moiety) that is part of the MTS peptide. In some embodiments, the MTS molecule contains a detectable moieties which provide for an indication of a cleavage event. In some embodiments, cleavage could be detected by size changes in the length of the peptide (e.g., gel electrophoresis, size exclusion, column chromatography, immunoflourescence, etc.) or other biochemical and physical changes that occur to the MTS molecule. In some embodiments, the MTS molecule comprises a label which facilitates cleavage detection. In some embodiments, cleavage could be detected using a FRET-based pair (a reporter dye and an acceptor dye that are involved in fluorescence resonance energy transfer known as FRET), where a change in fluorescence is indicative of a cleavage event. See, for examples, Examples 1-3. Methods for detecting and monitoring cleavage of proteins are well known and any such methods could be employed in detecting cleavage of the MTS molecules of the invention.

In some embodiments, the invention provides an ex vivo method for detecting the presence of one or more protease activities in a neoplasia sample comprising a) combining ex vivo said sample from a subject with a molecule of the structure according to one of the following:

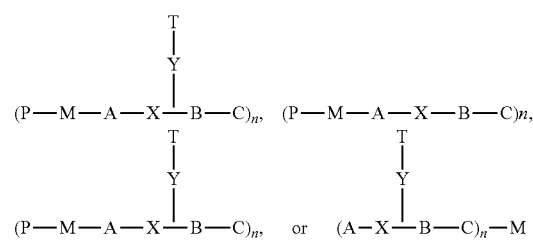

wherein cleavage of said molecule is indicative of the presence of protease activity and wherein P is a pre-targeting moiety; M is a macromolecular carrier, A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound; and n is an integer between 1 and 20; and C is a detectable moiety and b) detecting cleavage of said molecule by detecting a change in said detectable moiety C, wherein said change in C is indicative of cleavage and said cleavage is indicative of the presence of one or more protease activities in said neoplasia. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, the screening is small scale, involving screening of 1, 5, 10, 20 or 30 samples. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, one protease activity can be detected. In some embodiments, 2, 3, 4, 5, 6, 7, 8, 9 or 10 protease activities can be detected. In some embodiments, one or more protease activities can be detected. In some embodiments, said portion A has between about 5 to about 9 acidic amino acid residues, and said portion B has between about 9 to about 16 basic amino acid residues.

In some embodiments, the invention provides an ex vivo method of screening for the presence of one or more protease activities in a neoplasia sample comprising combining ex vivo said neoplasia sample from a subject with a molecule of the structure according to one of the following:

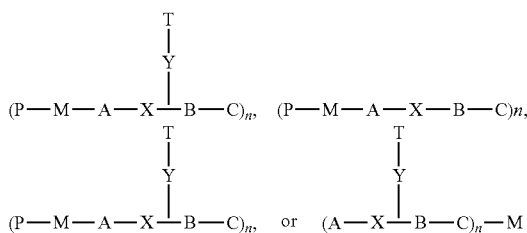

wherein cleavage of said molecule is indicative of the presence of protease activity and wherein P is a pre-targeting moiety; M is a macromolecular carrier, A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound; and n is an integer between 1 and 20; and C is a detectable moiety; and b) detecting cleavage of said molecule by detecting a change in said detectable moiety C, wherein said change in C is indicative of cleavage and said cleavage is indicative of the presence of one or more protease activities in said neoplasia. In some embodiments the MTS molecules can be used in screening assays to determine how many proteases and/or which proteases are expressed by a sample. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, the screening is small scale, involving screening of 1, 5, 10, 20 or 30 samples. In some embodiments, screening is large scale, and involves screening of 100, 500, 1000, 10000, 100 000, 500000 or more samples. In some embodiments, samples are screened for 1, 2, 3, 4, 5, 6, 7, 8, 9, 10 or more protease activities using MTS molecules of the invention. In some embodiments, screening information can be employed to develop data bases and incorporated with other bioinformatic information in order to develop hydrogen peroxide profiles of samples. In some embodiments, said portion A has between about 5 to about 9 acidic amino acid residues, and said portion B has between about 9 to about 16 basic amino acid residues.

In some embodiments, the invention provides an ex vivo method of determining the protease profile of a neoplasia sample, comprising a) combining said sample from a subject with a molecule of the structure according to one of the following:

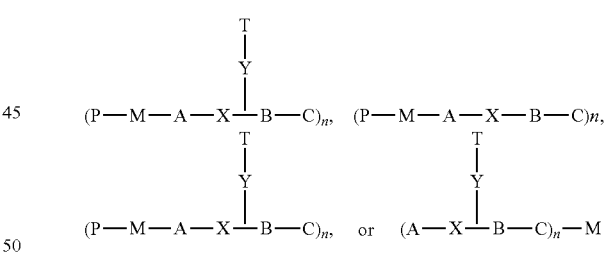

wherein cleavage of said molecule is indicative of the presence of protease activity and wherein P is a pre-targeting moiety; M is a macromolecular carrier, A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound; and n is an integer between 1 and 20; and C is a detectable moiety; and b) detecting cleavage of said molecule by detecting a change in said detectable moiety C, wherein said change in C is indicative of cleavage and said cleavage is indicative of the presence of one or more protease activities in said neoplasia. In some embodiments the MTS molecules can be used in screening assays to determine how many proteases and/or which proteases are expressed by a sample. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, the MTS molecules are employed to develop a protease profile for one or more neoplasia samples. Hydrogen peroxide profiles can be employed to develop databases and can be incorporated with other information, including for example bioinformatic information, in order to develop hydrogen peroxide profiles of disease samples and for hydrogen peroxide profiles for patients with diseases. Diseases contemplated by the methods of the present invention include inflammatory diseases, neurodegenerative diseases, cardiovascular diseases, diabetes and neoplasia. In some embodiments, said portion A has between about 5 to about 9 acidic amino acid residues, and said portion B has between about 9 to about 16 basic amino acid residues.

In some embodiments, the invention provides an ex vivo method of determining a treatment regimen based on the protease profile of a neoplasia sample, comprising a) combining ex vivo said neoplasia sample from a subject with a molecule of the structure according to one of the following:

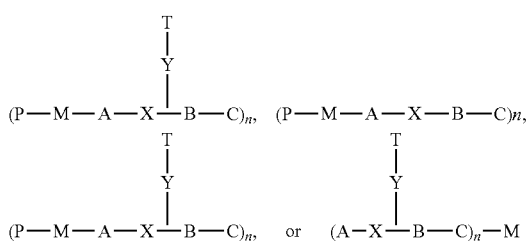

wherein cleavage of said molecule is indicative of the presence of protease activity and wherein P is a pre-targeting moiety; M is a macromolecular carrier, A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound; and n is an integer between 1 and 20; and C is a detectable moiety; and b) detecting cleavage of said molecule by detecting a change in detectable moiety C, wherein said change in C is indicative of cleavage and said cleavage is indicative of the presence of one or more protease activities and wherein the presence and/or absence of one or more protease activities allows for determining a medical treatment regimen. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, the MTS molecules are employed to determine a treatment regimen. Matrix metalloproteinase (MMP), hydrogen peroxide or other cleavage information and/or profiles can be employed to develop databases and can be incorporated with other information, for example bioinformatic information, in order to develop cleavage profiles of samples. In some embodiments, such information can be combined with information regarding treatment and surgical options know to those of skill in the medical arts in order to determine and develop personalize treatment regimens for individual subjects. In some embodiments, the medical regimen is a surgical regimen. After detecting the presence or absence of one or more proteases based on MTS molecule cleavage, a determination of the usefulness of an MTS molecule in surgical procedures can be determined. Detection of cleavage of the MTS molecule would be indicative of the presence of one or more proteases and such information would allow for a determination of usefulness of the peptide in a surgical procedure in order to detect tumor borders and assist with surgical removal as previously described (See, e.g., see, WO 2005/042034, WO/2006/125134, WO2011008992 and WO2011008996). Non-detection of cleavage of the MTS molecule would be indicative of the absence of a protease and the non-usefulness of the peptide in a surgical procedure. In some embodiments, said portion A has between about 5 to about 9 acidic amino acid residues, and said portion B has between about 9 to about 16 basic amino acid residues.

In some embodiments, the invention provides an ex vivo method of characterizing a neoplasia based on the protease profile of said neoplasia, comprising a) combining a sample of said neoplasia from a subject with a molecule of the structure according to one of the following:

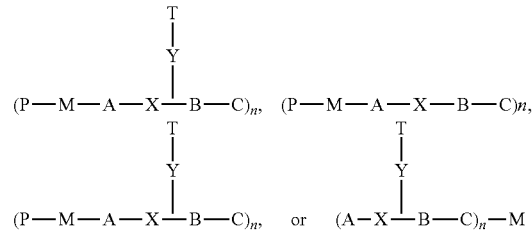

wherein cleavage of said molecule is indicative of the presence of protease activity and wherein P is a pre-targeting moiety; M is a macromolecular carrier, A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound; and n is an integer between 1 and 20; and C is a detectable moiety; and b) detecting cleavage of said molecule by detecting a change in detectable moiety C, wherein said change in C is indicative of cleavage and said cleavage is indicative of the presence of one or more protease activities and wherein the presence and/or absence of one or more protease activities allows for determining a medical treatment regimen. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments, the neoplasia is characterized based on histology, stage, grade, location, type, or any of a variety of characteristics known to those skilled in the medical arts. In some embodiments, the protease profile is correlated with histology, stage, grade, location, type, or any of a variety of characteristics known to those skilled in the medical arts in order to characterize the neoplasia. In some embodiments, the presence of the protease activity is indicative of neoplasia. In some embodiments, the presence of the protease activity is indicative of metastasis. In some embodiments, said portion A has between about 5 to about 9 acidic amino acid residues, and said portion B has between about 9 to about 16 basic amino acid residues.

In some embodiments, the present invention provides a diagnostic composition for use in the methods of any of the preceding claims comprising: a molecule of the structure according to one of the following:

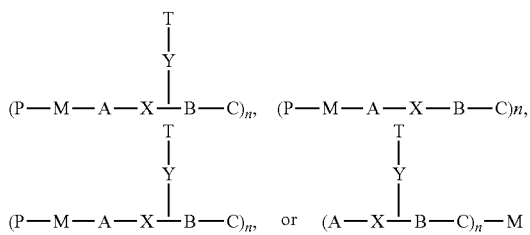

wherein cleavage of said molecule is indicative of the presence of protease activity and wherein P is a pre-targeting moiety; M is a macromolecular carrier, A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B and is cleavable under physiological conditions; Y is a second cleavable linker of about 2 to about 100 atoms, or about 3 to about 30 atoms, joining A-X-B with T and is cleavable under physiological conditions; T is a compound for delivery to a target, including for example a therapeutic compound; and n is an integer between 1 and 20; and C is a detectable moiety; and b) detecting cleavage of said molecule by detecting a change in detectable moiety C, wherein said change in C is indicative of cleavage and said cleavage is indicative of the presence of one or more protease activities and wherein the presence and/or absence of one or more protease activities allows for determining a medical treatment regimen. In some embodiments, X is a cleavable linker of 2 or more atoms, 10 or more, 50 or more atoms, 100 or more atoms, 200 or more atoms, 300 or more atoms, 400 or more atoms or 500 or more atoms. In some embodiments, X is a cleavable linker cleavable by a matrix metalloproteinase (MMP) or a reactive oxygen species. In some embodiments, Y is a cleavable linker of 2 or more atoms, 10 or more, 50 or more atoms, 100 or more atoms, 200 or more atoms, 300 or more atoms, 400 or more atoms or 500 or more atoms. In some embodiments, Y is a cleavable linker cleavable by a matrix metalloproteinase (MMP) or a reactive oxygen species. In some embodiments of the diagnostic composition, said portion A has between about 5 to about 9 acidic amino acid residues, and said portion B has between about 9 to about 16 basic amino acid residues.

In some embodiments, the present invention provides an array comprising: a plurality of molecules of the structure according to one or more of the following:

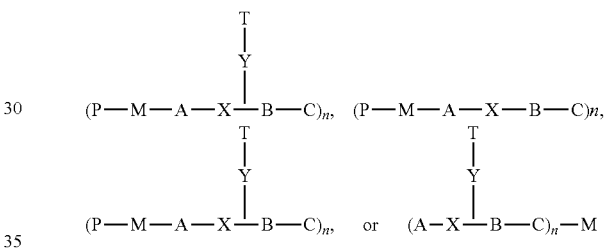

wherein cleavage of said molecule is indicative of the presence of protease activity and wherein P is a pre-targeting moiety; M is a macromolecular carrier, A is peptide portion with a sequence comprising about 2 to about 20 acidic amino acids, which when linked with portion B is effective to inhibit or prevent cellular uptake of portion B; B is a peptide portion of about 5 to about 20 basic amino acid residues, which is suitable for cellular uptake; X is a first cleavable linker of about 2 to about 100 atoms, or about 3 to about 30 atoms, joining A with B; Y is a second cleavable linker of about 2 to about 100 atoms, or about 3 to about 30 atoms, joining A-X-B with T; T is a compound for delivery to a target, including for example a therapeutic compound; and n is an integer between 1 and 20; and C is a detectable moiety. In some embodiments of the array, said portion A has between about 5 to about 9 acidic amino acid residues, and said portion B has between about 9 to about 16 basic amino acid residues. In some embodiments, the array comprises a plurality of molecules of one or more of said structures and wherein the cleavable linker X comprises a plurality of cleavable linkers X. In some embodiments, the array comprises a plurality of molecules of one or more of said structures and wherein the cleavable linker Y comprises a plurality of cleavable linkers Y. In some embodiments of the array, the plurality of cleavable linkers X and/or Y linking a portion A to a portion B are cleavable by a single protease. In some embodiments of the array, the plurality of cleavable linkers X and/or Y linking a portion A to a portion B are cleavable by more than one protease. In some embodiments, an array of the invention would contain a plurality of one species (one type) of MTS molecules. In some embodiments, an array of the invention would contain a plurality of one species (one type) of MTS molecules and multiple samples could be screened for one protease activity type. In some embodiments, an array of the invention would contain a plurality of a plurality of species (multiple types) of MTS molecules. In some embodiments, an array of the invention would contain a plurality of a plurality of species (multiple types) of MTS molecules and one or more samples could be screened for one or more protease activity types. An array can include but is not limited to any substrate to which the MTS molecules can be bound, and can include for examples solid substrates, micro-arrays and microchips. Methods for making arrays are well known and can even be supplied by commercial suppliers. Arrays can be manually processed and/or automated or a combination thereof. Such arrays can be employed in low-throughput as well as high-throughput applications and can analyze one or more samples, one or more proteases or any combination thereof.

In some embodiments of the above described methods, ratiometric analysis can be employed to determine the level of enzyme activity and/or to assess the percentage of enzymatically positive tumors in a population. Such ratiometric analyses can be based on the ratio of cleaved to non-cleaved MTS molecules. In some embodiments, ratiometric analysis can be employed to correlate ex vivo cleavage with in vivo cleavage activities.

In some embodiments, the protease information can be correlated with histology, grade, type, characterization, etc. in order to better characterize neoplasias and to provide personalized prognosis and treatment regimens. Such information can be provided to those of skill in the medical arts and be employed to develop personalized medical treatment regimens for individuals.

EXAMPLES

The methods system herein described are further illustrated in the following examples, which are provided by way of illustration and are not intended to be limiting.

Example 1: Pre-Targeted ACPP in Tumor Imaging

Figure 2:
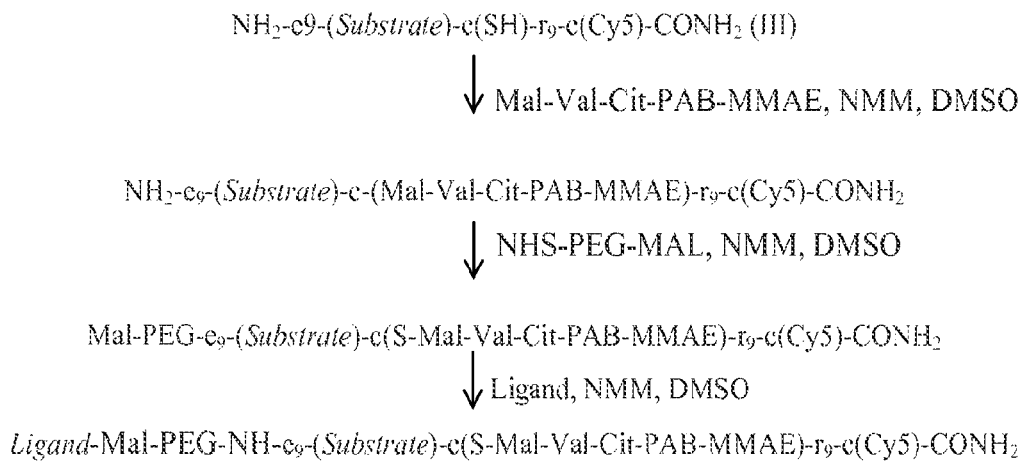
FIG. 2 illustrates the synthesis of an exemplary pre-targeted ACPP comprising MMAE as a therapeutic agent.
Figure 3:
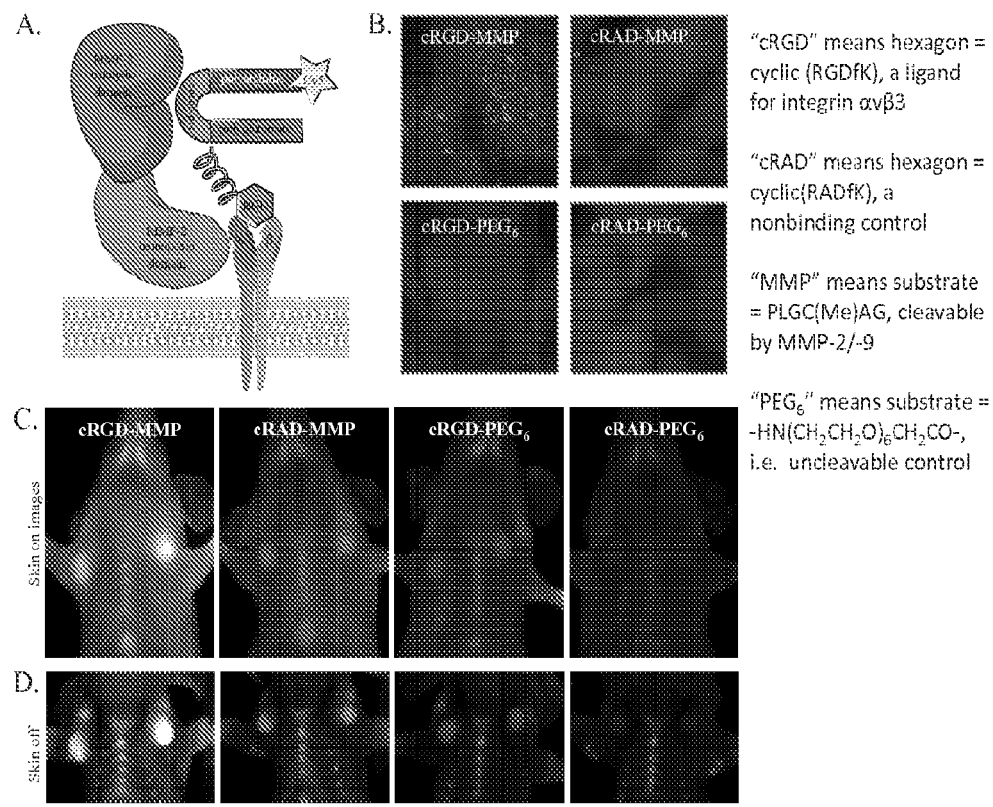
FIG. 3 illustrates pre-targeted ACPP in tumor imaging. A) Schematic depiction shows the RGD (shown as hexagon) containing ACPP getting activated by MMP-2 that is co-expressed with $\alpha v\beta 3$ integrin receptor. B) Confocal imaging of RGD-pretargeted ACPP (top left panel) and the respective control molecules (top right and bottom panels) treated U87MG glioblastoma cells verify the possible synergy between MMP and $\alpha v\beta 3$ in enhancing activation of ACPP. C), D) fluorescence in vivo imaging of mice that were previously injected with pre-targeted cleavable ACPP (cRGD-MMP), untargeted cleavable ACPP(cRAD-MMP), pre-targeted uncleavable ACPP (cRGD-PEG6), untargeted uncleavable ACPP (cRAD-PEG6) show excellent tumor contrast only when probe retains both MMP cleavability and pretargeting. Arrow mark indicates tumor region.
Figure 5:
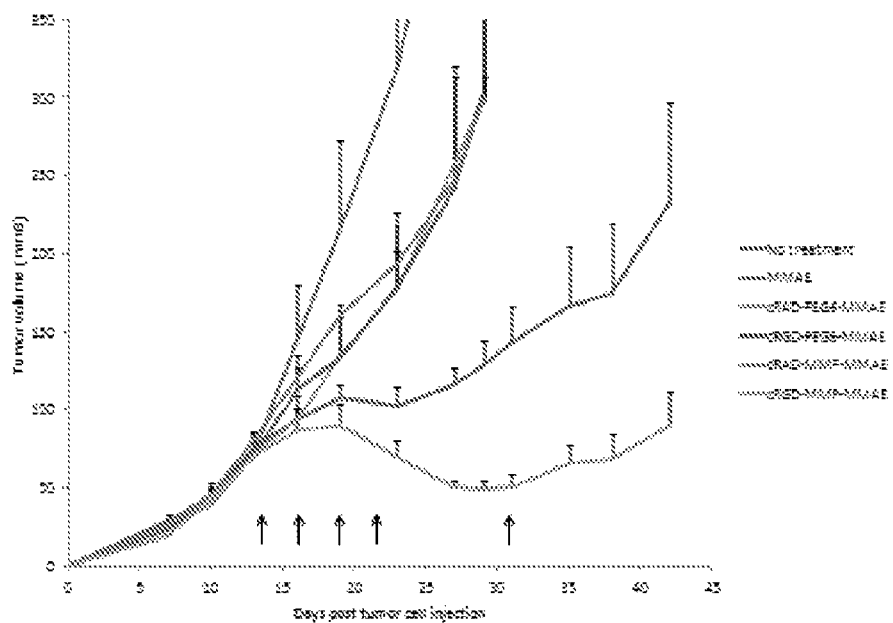
FIG. 5 illustrates tumor growth curves a 7 nM dose. Animals were given 7 nM (0.2 mg/kg) dose on days 13, 16, 19, and 22. All treatment groups are n=4 with two tumors per mouse, with the exception of cRAD-PEG6-MMAE.
Figure 6:
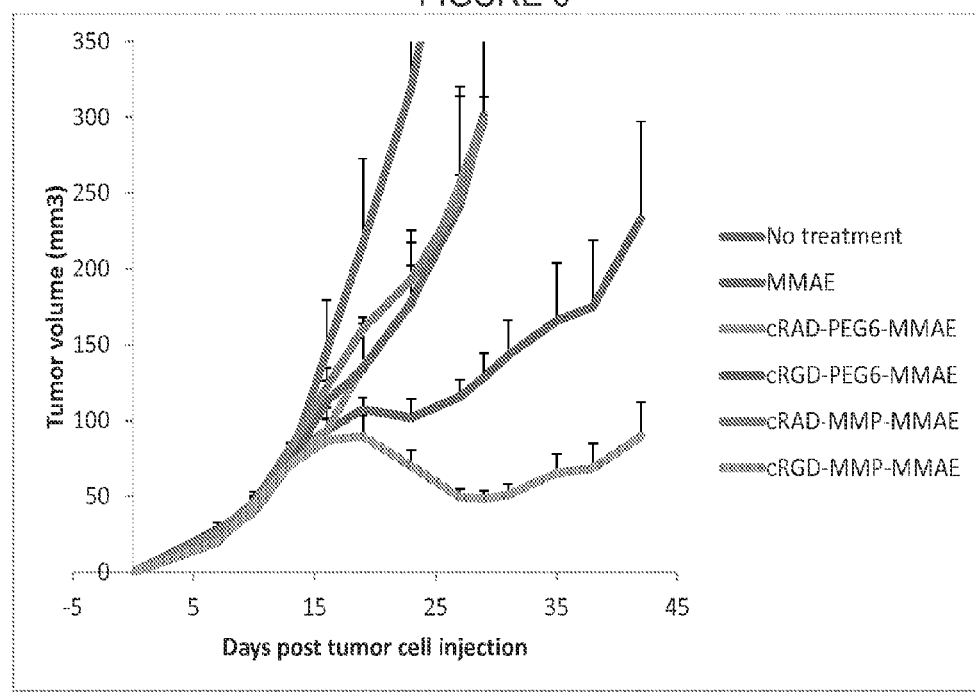
FIG. 6 illustrates tumor growth curves with a 7 nM dose and a final treatment at day 31.

Cyclic RGD [cyclic(RGDfK) or cyclic(RGDfC)], a popular ligand for $\alpha v\beta 3$, was chosen as the pre-targeting moiety and was attached to the (D-glu)$_9$ portion of a Cy5-labeled MMP-2 cleavable ACPP so that protease attack at a cleavable substrate would separate (D-arg)$_9$-Cy5 CPP from c(RGDfK)-(D-glu)$_9$ (FIG. 3A). The MMP 2/9-cleavable substrate in ACPPs was chosen to be oPLGC(Me)AG/-o, where o denotes 5-amino-3-oxopentanoyl, a short hydrophilic spacer. Dissociation of the latter from the $\alpha v\beta 3$ allows the integrin-MMP complex to rebind fresh substrate for continued catalytic amplification. Conjugation of c(RGDfK) to the ACPP had no impact on either the cleavage kinetics by pure MMP-2 or the affinity for $\alpha v\beta 3$ in vitro. However, U87MG glioblastoma cells took up the dual targeted peptide to a significantly greater extent than control peptides that crippled each of the targeting mechanisms separately (FIG. 3B). In these controls, the cleavable linker PLGC(Me)AG was replaced by uncleavable PEG6 or the c(RGDfK) was replaced by c(RADfK). When both these modifications were combined, almost no fluorescence uptake was detectable. Dual targeting was tested in vivo in orthotopic xenografts of MDA-MB-231 mammary tumors, imaged 6 hr after intravenous administration of the Cy5 labeled peptides. Tumor contrast was obtained with all of the probes except for the double negative control (FIG. 3C, D). The dually targeted probe had 4 fold higher tumor fluorescence, 2-3 fold higher tumor:normal tissue contrast and 2-3 fold higher standardized uptake value (SUV) than the control peptides with either ACPP cleavage or integrin binding crippled. Cryosections showed that dual targeting improved the ability of the peptide to penetrate to the tumor core.

Example 2: Pre-Targeted ACPP in Chemotherapy

Figure 7:
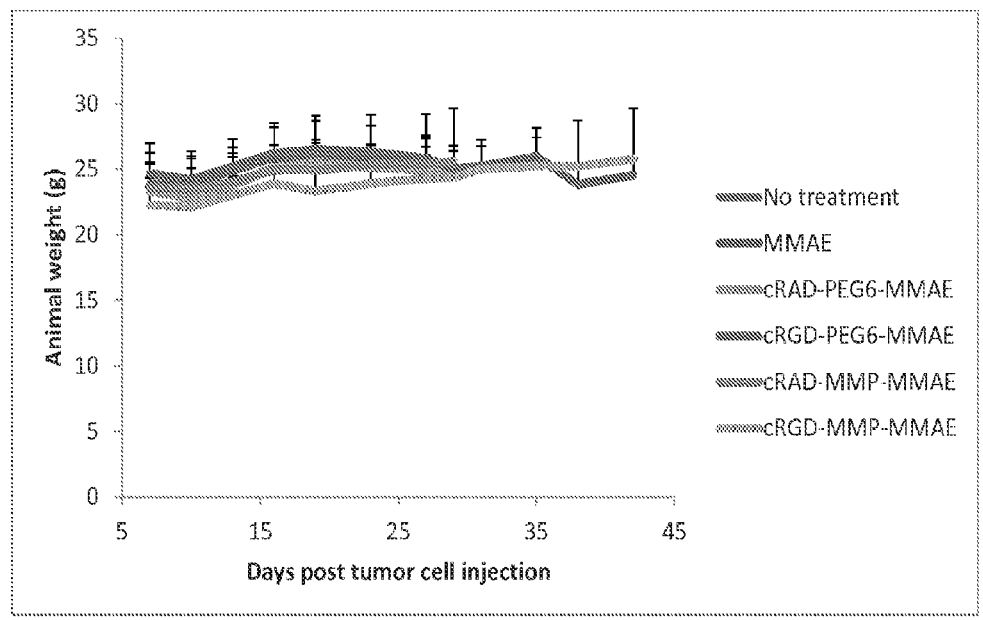
FIG. 7 illustrates animal weights with a 7 nM dose.
Figure 8:
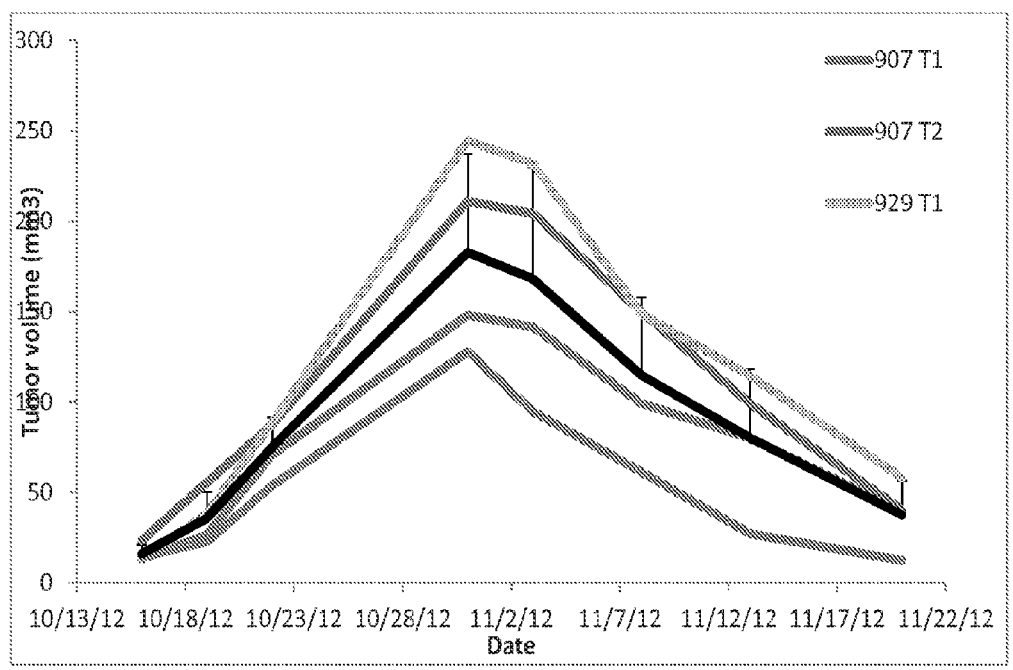
FIG. 8 illustrates tumor growth curves, 20 nM dose of cRGD-MMP-MMAE.
Figure 9:
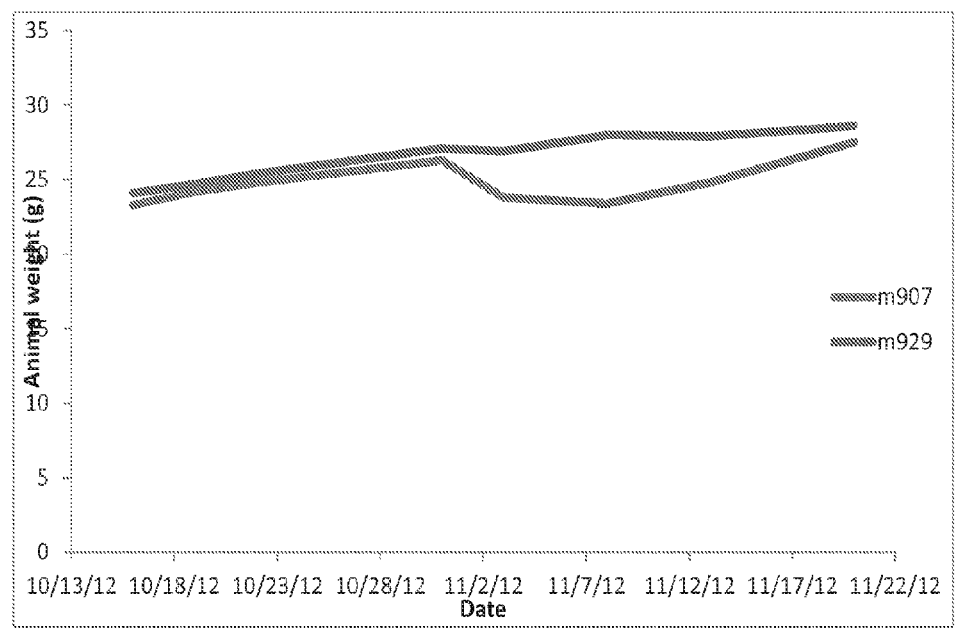
FIG. 9 illustrates animal weights, 20 nM dose of cRGD-MMP-MMAE.
Figure 10:
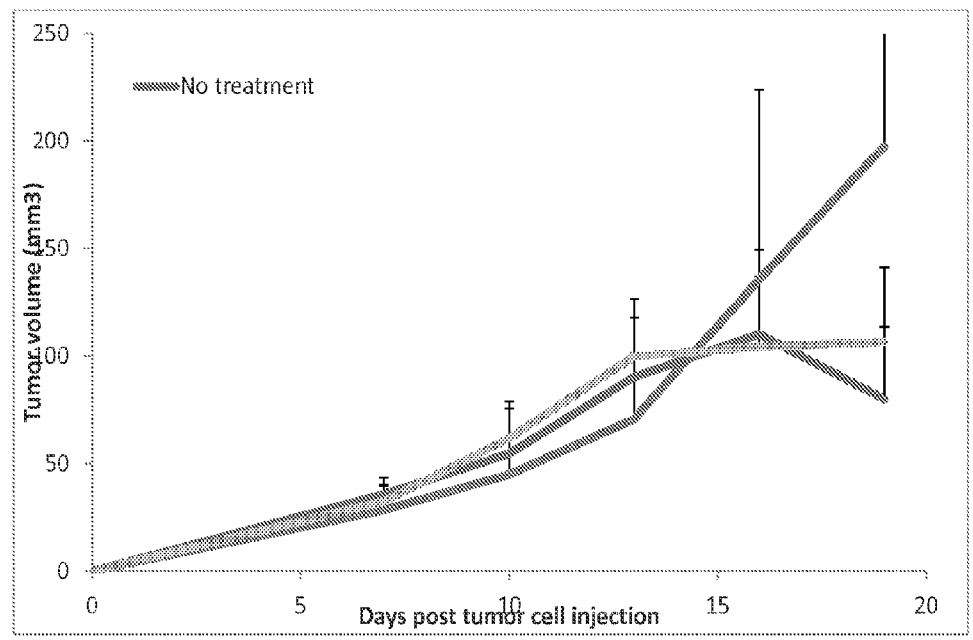
FIG. 10 illustrates tumor growth curves, 40 nM dose of cRGD-MMP-MMAE days 13 and 16 post TCI.
Figure 11:
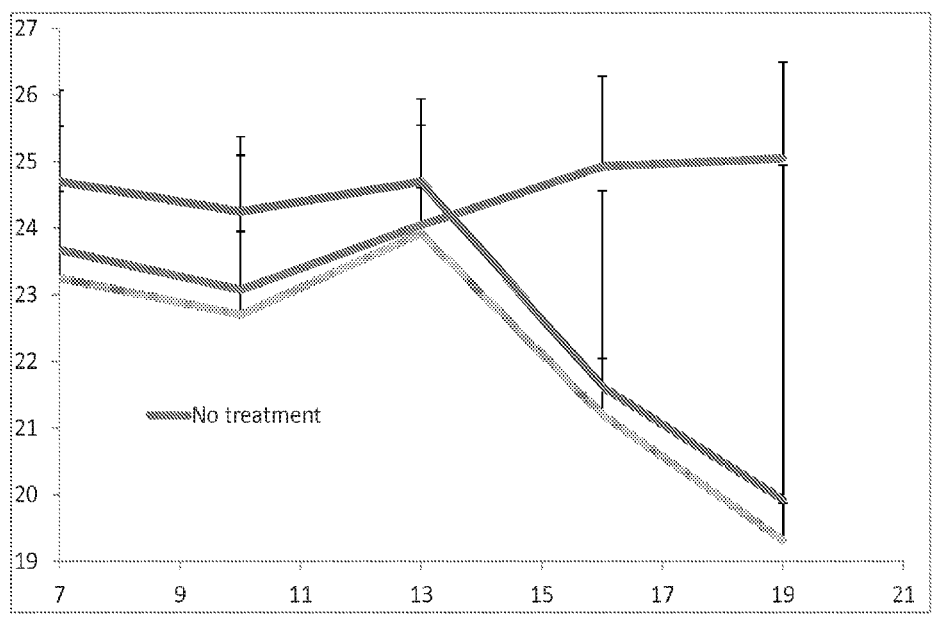
FIG. 11 illustrates animal weights, 40 nM dose of cRGD-MMP-MMAE.

Monomethyl auristatin E (MMAE), a potent chemotherapeutic inhibitor of tubulin polymerization, was conjugated to an ACPP via a peptide linker, Val-Cit-(p-amido)benzyloxycarbonyl, which is cleavable by cathepsin B, an endolysosomal protease. Mice harboring MDA-MB-231 orthotopic xenografts were dosed with cRGD-ACPP-MMAE at 0.2 mg/kg equivalents MMAE (6.5 nanomoles peptide) every three days for a total of four doses and tumor volumes were measured at regular intervals. The dual negative peptide drug conjugate (c(RADfC) and PEG6) performed worse than free MMAE, whereas the dual targeted peptide drug conjugate (c(RGDfC) and PLGC(Me)AG) demonstrated a significant (p=3.1×10-3) reduction in average tumor volume compared to MMAE (FIG. 4A). When the dose was increased to 0.32 mg/kg equivalents of MMAE, the dual targeted peptide caused 4 out of 8 tumors to regress completely, compared to 2 out of 8 for equimolar free MMAE. The ACPPs caused no weight loss or gross toxicity. Tumor growth curves are demonstrated in FIGS. 5-6, 8, and 10. Animal weights are illustrated in FIGS. 7, 9, and 11.

The targeting mechanism involves several steps, a) binding of cRGD ligand to $\alpha v\beta 3$ receptor, b) proteolysis of ACPP by MMP-2, c) dissociation of MMAE-r9-Cy5 from cRGD-e9, d) uptake of MMAE-r9-Cy5 into cell through endocytosis, e) Cathepsin B induced cleavage of amide bond between Cit and PAB and subsequent release of MMAE, f) diffusion of MMAE across endosomal or lysosomal membrane into cytosol, g) MMAE interference with microtubules, and h) subsequent cell death.

Example 3: Pre-Targeted ACPP in Dual Targeted Imaging and Chemotherapy

The Integrin $\alpha v\beta 3$ is known to bind to the hemopexin domain of MMP-27 and is upregulated in many tumors and their vasculature. Cyclic(RGDfK), a popular ligand for $\alpha v\beta 3$, was chosen as the pre-targeting moiety and was attached to the (D-glu)$_9$ portion of a Cy5-labeled MMP-2 cleavable ACPP so that protease attack would separate (D-arg)$_9$-Cy5 CPP from c(RGDfK)-(D-glu)$_9$. Dissociation of the latter from the $\alpha v\beta 3$ would allow the integrin-MMP complex to rebind fresh substrate for continued catalytic amplification. Dual targeting was tested in vivo in orthotopic xenografts of MDA-MB-231 mammary tumors. These experiments suggest that pretargeting with $\alpha v\beta 3$ increases the sensitivity to MMP-2, which adds catalytic amplification beyond simple 1:1 binding to the integrin.

The targeting mechanism involves several steps, a) binding of cRGD ligand to $\alpha v\beta 3$ receptor, b) proteolysis of ACPP by MMP-2, c) dissociation of MMAE-r9-Cy5 from cRGD-e9, d) uptake of MMAE-r9-Cy5 into cell through endocytosis, e) Cathepsin B induced cleavage of amide bond between Cit and PAB and subsequent release of MMAE, f) diffusion of MMAE across endosomal or lysosomal membrane into cytosol, g) MMAE interference with microtubules, and h) subsequent cell death.

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A molecule having the formula:

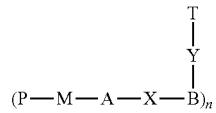

wherein:
P is cyclic RGD (cRGD);
M is a PEG polymer;
A is 9 consecutive glutamates;
X is selected from DPRSFL and PPRSFL;
Y is Val-Cit-(p-amido)benzyloxycarbonyl;
T is monomethyl auristatin E (MMAE);
B is 9 consecutive arginines; and
n is 1.

2. The molecule of claim 1, wherein the molecule further comprises an imaging agent C, wherein C is Cy5.

3. The molecule of claim 1, wherein X is DPRSFL.

4. The molecule of claim 1, wherein X is PPRSFL.

5. A composition comprising the molecule of claim 1 and a pharmaceutically acceptable carrier vehicle.

6. A composition comprising the molecule of claim 1 and a diagnostic buffering agent.

* * * * *